United States Patent [19]
Williamson

[11] Patent Number: 5,470,696
[45] Date of Patent: Nov. 28, 1995

[54] PHOTOGRAPHIC COLOR COUPLERS AND PHOTOGRAPHIC MATERIALS CONTAINING THEM

[75] Inventor: Hugh M. Williamson, Hanwell, United Kingdom

[73] Assignee: Eastman Kodak Company, Rochester, N.Y.

[21] Appl. No.: 70,305

[22] PCT Filed: Oct. 2, 1992

[86] PCT No.: PCT/EP92/02293

§ 371 Date: Jun. 1, 1993

§ 102(e) Date: Jun. 1, 1993

[87] PCT Pub. No.: WO93/07534

PCT Pub. Date: Apr. 15, 1993

[30] Foreign Application Priority Data

Oct. 30, 1991 [GB] United Kingdom ............ 9121059

[51] Int. Cl.$^6$ .................. G03C 7/32; G03C 7/38
[52] U.S. Cl. ............ 430/543; 430/386; 430/387; 430/388; 430/389; 430/558
[58] Field of Search ................. 430/543, 386, 430/387, 388, 389, 558

[56] References Cited

U.S. PATENT DOCUMENTS

| | | | |
|---|---|---|---|
| 4,404,273 | 9/1983 | Forte et al. | 430/377 |
| 4,661,437 | 4/1987 | Tschopp | 430/390 |
| 5,047,314 | 9/1991 | Sakai et al. | 430/505 |
| 5,206,129 | 4/1993 | Sato et al. | 430/558 |

FOREIGN PATENT DOCUMENTS

| | | |
|---|---|---|
| 0276319 | 8/1988 | European Pat. Off. . |
| 0431374 | 11/1990 | European Pat. Off. . |
| 190348 | 7/1992 | Japan . |
| 9214189 | 8/1992 | WIPO . |

OTHER PUBLICATIONS

"Preparation and Reactions of 1,2–dicyano–1, 2–disulfonylethylenes" by E. L. Martin, Journal of the American Chemical Society, Aug. 20, 1963 at p. 2449.

Primary Examiner—Lee C. Wright
Attorney, Agent, or Firm—Arthur E. Kluegel

[57] ABSTRACT

A photographic element comprising a support, at least one photosensitive silver halide layer and associated therewith a color coupler of the general formula (1) or (2):

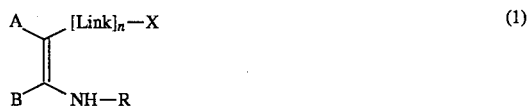

(1)

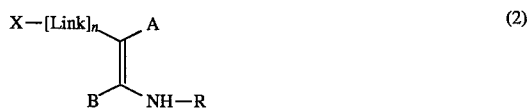

(2)

wherein A and B represent the same or different electron-withdrawing group,

X is H or a group which splits off on coupling with oxidized color developer,

R is an alkyl, cycloalkyl, aryl or heterocyclic which may be substituted, —COR$^1$, —CSR$^1$, SOR$^1$, SO$_2$R$^1$, —NHCOR$^1$, —CONHR$^1$, —COOR$^1$, —COSR$^1$, —NHSO$_2$R$^1$ wherein R$^1$ is an alkyl, cycloalkyl, or aryl group any of which are optionally substituted,
and wherein two or more of A, B, R, and X optionally form part of a ring, Link is a linking group and n is 0, 1 or 2.

17 Claims, 1 Drawing Sheet

PHOTOGRAPHIC COLOR COUPLERS AND PHOTOGRAPHIC MATERIALS CONTAINING THEM

This invention relates to photographic colour couplers and in particular to a class of couplers.

Colour couplers are known to belong to a number of classes, for example magenta dye-forming couplers can be pyrazolones, pyrazolotriazoles and pyrazolobenzimidazoles while yellow dye-forming couplers can be acetanilides. European Patent Specification 0 431 374 A describes β,γ-unsaturated nitriles as cyan colour couplers of the general formula:

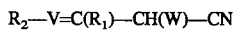

$R_2$—V=C($R_1$)—CH(W)—CN wherein W is hydrogen or an atom or group capable of being released when the compound is subjected to a coupling reaction with oxidised product of an aromatic primary amine derivative and is attached to a carbon atom having an sp$^3$ electronic configuration, $R_1$ is a substituent, V is nitrogen or —C($R_3$)= , if V represents nitrogen, $R_2$ represents a substituent, if V represents —C($R_3$)= , $R_2$ and $R_3$ each represent a substituent, provided that at least one of $R_2$ and $R_3$ represent an electron attractive substituent, and provided that if $R_2$ or $R_3$ represents an aliphatic group or an aromatic group, the other does not represent an acyl group, and $R_1$ and $R_2$ may bond together to form a ring.

The couplers of the above general formula are said to have less subsidiary absorption in the blue region of the spectrum. In support of this contention one drawing (FIG. 1) and a table of data are provided wherein the dye formed from Coupler 53 is compared to that from Comparative Compound (1)—a phenolic coupler.

The compounds of the present invention are not cyan couplers and are distinct from those of European Specification 0 431 374A because, inter alia, the coupling position is a carbon atom having an sp$^2$ electronic configuration and the compounds are α,β-unsaturated. No examples of them appear in EP 0 431 374A, nor is any method of making them disclosed.

"Preparation and Reactions of 1,2-dicyano-1,2-disulfonylethylenes" by E L Martin, Journal of the American Chemical Society, Aug. 20, 1963 at page 2449, describes compounds of the formula:

RNH—C(CN)=C(CN)—SO$_2$R.

The method of preparation means that only compounds having the —SO$_2$R can be prepared. In addition there is no disclosure of ballasted compounds.

The present invention provides a new class of couplers capable of forming dyes having good spectral characteristics such as maximum wavelength ($\lambda_{max}$) and half-band width, little unwanted absorption of blue light and good fastness properties. Both magenta and yellow dye formation has been observed.

According to the present invention there are provided photographic elements comprising a support, at least one photosensitive silver halide layer and in or adjacent said silver halide layer a colour coupler of the general formulae:

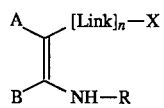

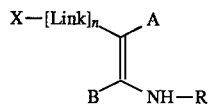

wherein A and B represent the same or different electron-withdrawing group,

X is H or a group which splits off on coupling with oxidised colour developer,

R is an alkyl, cycloalkyl, aryl or heterocyclic group any of which may be substituted, —COR$^1$, —CSR$^1$, SOR$^1$, SO$_2$R$^1$, —NHCOR$^1$, —CONHR$^1$, —COOR$^1$, —COSR$^1$, —NHSO$_2$R$^1$ wherein R$^1$ is an alkyl, cycloalkyl, or aryl group any of which are optionally substituted, and wherein two or more of A, B, R, and X optionally form part of a ring, Link is a linking group and n is 0, 1 or 2.

In one embodiment A and B together complete an electron-withdrawing heterocycle which may be substituted. In another embodiment R and X together complete a heterocyclic ring which is optionally substituted.

It is noted that formulae (1) and (2) represent geometric isomers (cis and trans versions) of the same compound.

Figure 1:
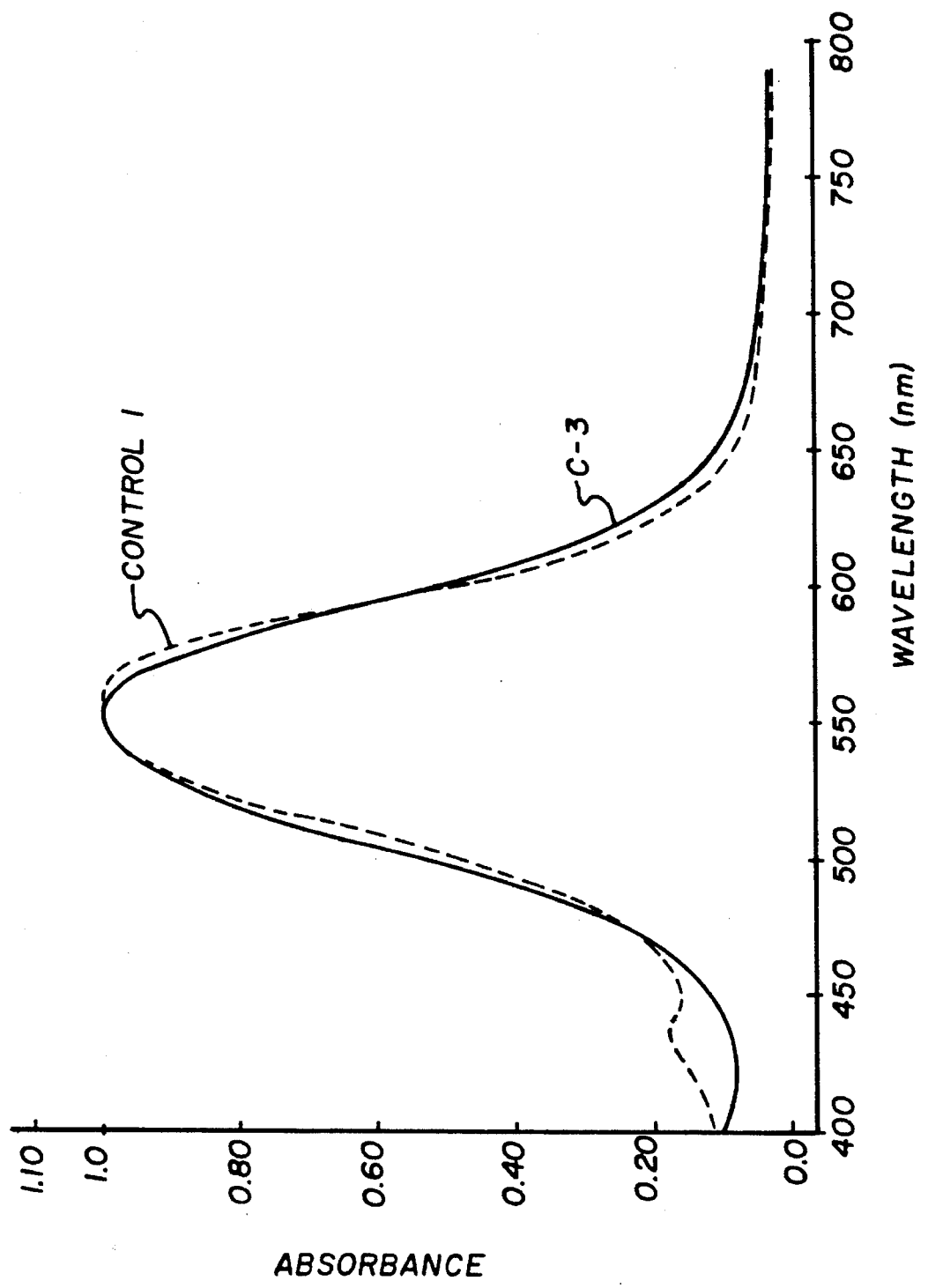
FIG. 1 is a plot of absorbents vs wavelength for the dyes obtained from coupler C-3 and control 1 (dotted line).

The advantages of the present invention include the provision of couplers of good activity capable of forming dyes having good spectral characteristics such as maximum wavelength ($\lambda_{max}$) and half-band width, little unwanted absorption of blue light, good fastness properties, $\lambda_{max}$ selectable under the influence of coupler solvents, and easy bleaching giving retouchability.

In one embodiment of the present invention the couplers contain a ballasting group of such size and configuration to render the coupler non-diffusible in the photographic material.

A and B may each individually represent an electron attractive group wherein the value of the Hammett substituent constant σ$_p$ (SIGMA$_p$ as defined by Hansch et al, J. Med. Chem., 1973, 16, 1207; and ibid. 1977, 20, 304) is 0.03 or greater, preferably 0.35 or greater and more preferably 0.5 or above.

A substituent or atom wherein the value of the σ$_p$ (SIGMA$_p$) is 0.03 or above includes a fluorine atom, a chlorine atom, a bromine atom, an iodine atom, a substituted alkyl group (e.g. trichloromethyl, trifluormethyl, chloromethyl and perfluorobutyl), a nitrile group, an acyl group (e.g. formyl, acetyl and benzoyl), a carboxyl group, a substituted or unsubstituted carbamoyl group (e.g. methylcarbamoyl) an aromatic group substituted by another electron attractive group (e.g. pentachlorophenyl, pentafluorophenyl), a heterocyclic group (e.g. 2-thienyl, 2-benzoxazolyl, 2-benzthiazolyl, 1-tetrazolyl and 1-phenyl-2-benzimidazolyl), a nitro group, an azo group (e.g. phenylazo), an amino group substituted by another electron attractive group (e.g. ditrifluoromethylamino), an alkoxy group substituted by another electron attractive group (e.g. trifluoromethoxy), an alkylsulphonyloxy group (e.g. methanesulphonyloxy), an acyloxy group (e.g. acetyloxy, benzoyloxy), an arylsulphonyloxy group (e.g. benzenesulphonyloxy), a phosphoryl group (e.g. dimethoxyphosphoryl and diphenylphosphoryl), a thioalkyl group substituted by another electron attractive group (e.g. trifluoromethyl), a sulphamoyl group, a sulphonamide group, a sulphonyl group (e.g. methanesulphonyl, benzenesulphonyl), a thiocyanate group and a sulphoxide group.

Examples of electron-withdrawing groups which A and B may represent are hydrogen, halogen, —CN, —$NO_2$, —$OR^4$, —$SR^4$, —$SO_2R^1$, —$OSO_2R^1$, —$SOR^1$, —NHCOR^1$, —$CONHR^1$, —$OCONHR^1$, —NHCO—$OR^1$, —$SO_2NH$—$R^1$, —$NHSO_2R^1$, —$NHSO_2NHR^1$, —NHNH—$SO_2$—$R^1$, —COOH, —$COOR^1$, —O—$COR^1$, —$COR^1$, —$CSR^1$, —$CONHNHR^1$, —$CF_3$, —$NH_2$, —$NHR^1$, —$NHR^1R^{1'}$, silyloxy, aryl, aralkyl, alkyl, cycloalkyl, ureido, imido, or a heterocycle, wherein $R^1$ is as defined above, $R^{1'}$ has the same definition as $R^1$ and may be the same or different to $R^1$, and $R^4$ is an alkyl, cycloalkyl, aryl or heterocyclic group any of which are optionally substituted, and wherein the nature of the groups $R^1$, $R^{1'}$, and $R^4$ and the substituents thereon are such that the group is electron-withdrawing.

The groups A and B may be also be any of the above groups joined by way of a group that will extend the conjugated path from A or B to the —NH—R group while leaving the whole group electron-withdrawing. Such a group may have the formula:

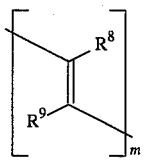

wherein $R^8$ and $R^9$ are each hydrogen, halogen, or an alkyl or aryl group that may be substituted.

or $R^8$ and $R^9$ may complete a carbocyclic or heterocyclic ring, and m is 1 or 2.

The ballast group may be located as part of A, B, X or R. Preferably the ballast group is part of R.

A preferred class of groups R have the general formula:

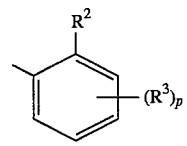

wherein p is 0, 1, 2, 3 or 4 and each $R^3$ is preferably in a meta or para position with respect to $R^2$ (if vacant);

each $R^3$ is individually a halogen atom or an alkyl, alkoxy, aryloxy, carbonamido, carbamoyl, sulphonamido, sulfamoyl, alkylsulphoxyl, arylsulphoxyl, alkylsulphonyl, arylsulphonyl, alkoxycarbonyl, aryloxycarbonyl, acyloxy, ureido, imido, carbamate, cyano, nitro, acyl, trifluoromethyl, alkylthio, carboxyl or heterocylic group; and $R^2$ is a hydrogen or halogen atom or an alkyl, alkoxy, aryloxy, alkylthio, arylthio, carbonamido, carbamoyl, sulphonamido, sulphamoyl, alkylsulpnonyl, arylsulphonyl, alkoxycarbonyl, acyloxy, acyl, cyano, nitro, or trifluoromethyl group.

Specific groups which R may represent are listed in the following table (Table 1).

TABLE 1

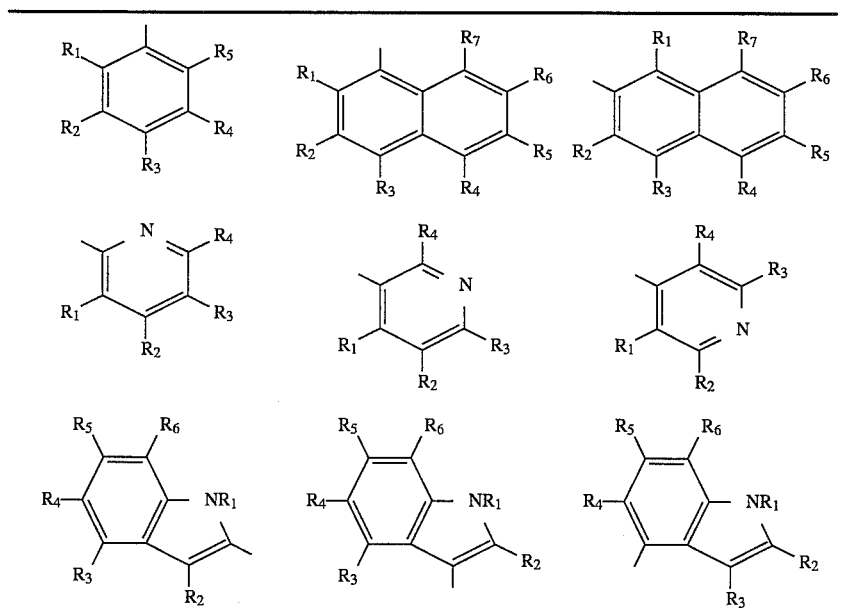

TABLE 1-continued
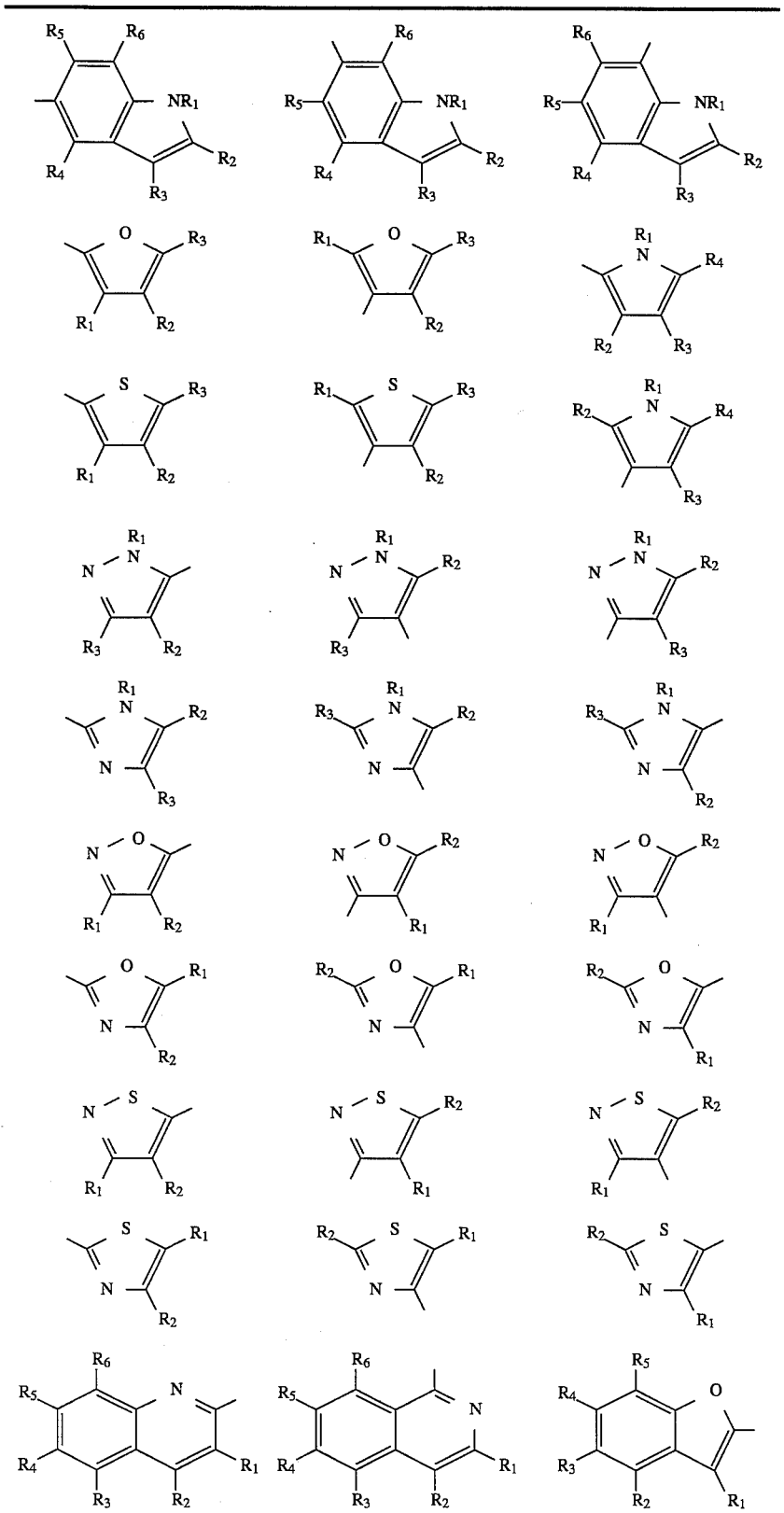

TABLE 1-continued
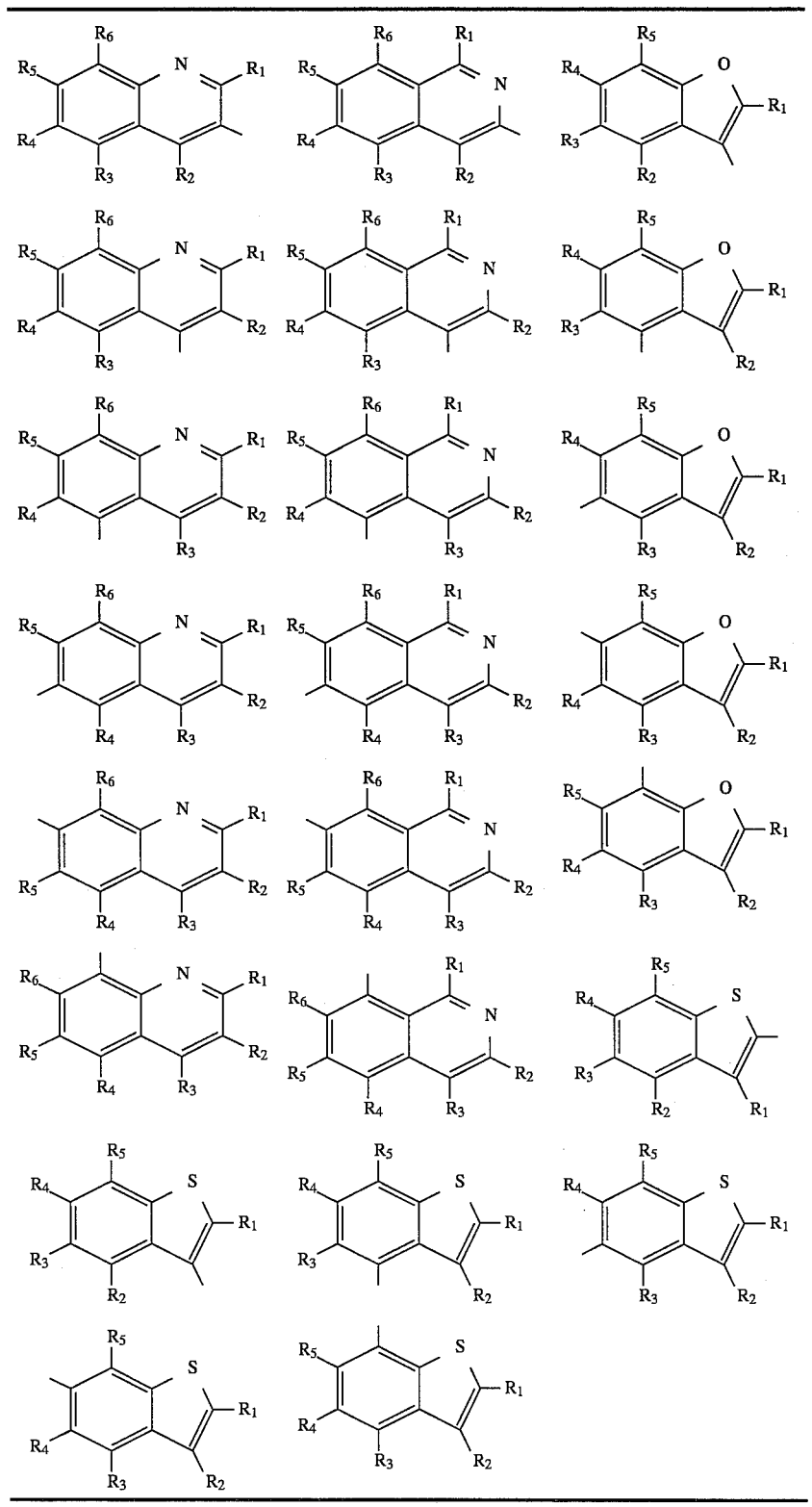
In the above groups the groups $R_1$ to $R_5$ are substituents not incompatible with the function of the compound. Examples of such substituents are those listed above for $R^2$ and $R^3$.
The ballast group or X may have water-solubilising substituents thereon and, in particular, those groups which will increase the activity of the coupler.

Examples of coupling-off groups which X may represent are shown in Table 3 below (a listing of compounds of the present invention).

The coupling-off group X may comprises the radical of a photographically useful group, for example a developer inhibitor or accelerator, a bleach accelerator, etc. Such groups are referred to in the Research Disclosure article referred to below.

Link may be a timing group which can be used to speed or slow release of a photographically useful group. Two timing groups may be used in circumstances where staged release is required.

The timing groups may have one of the following formulae shown in Table 2 in which they are shown attached to a photographically useful group (PUG):

TABLE 2

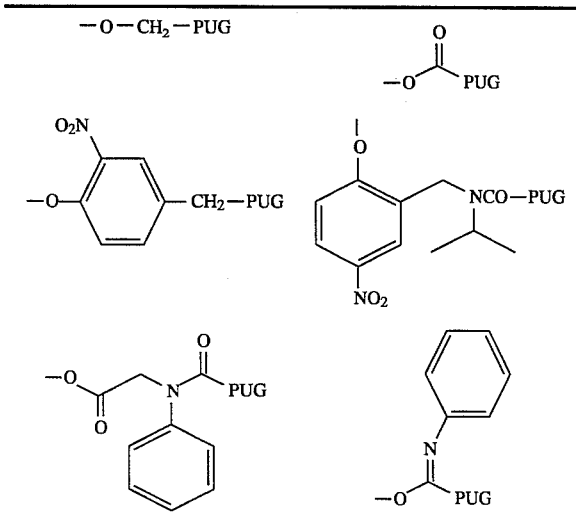

TABLE 2-continued

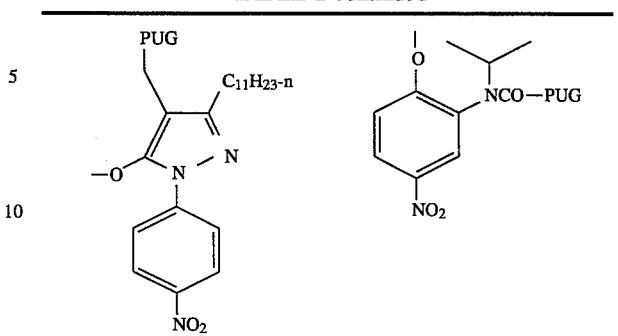

Specific examples of groups which $R^3$ may represent are given in the list of compounds of the invention listed in Table 3 below.

Examples of groups which split off on coupling include halogen, carboxy, heterocyclyl joined via a ring carbon or hetero atom in the heterocyclic nucleus $—OR^4$, $—SR^4$, arylazo or heterocyclylazo. Chloro is a particularly preferred coupling-off group as it gives the coupler superior activity. The group which splits off may provide a photographically useful compound. Many such groups are often known as photographically useful groups and they provide developer inhibitors, bleach accelerators, developer accelerators, antifoggants, competing couplers, etc. Many examples are listed in Research Disclosure Item 308119, December 1989 published by Kenneth Mason Publications, Emsworth, Hants, United Kingdom.

The present invention further provides photographic colour couplers of the general formulae:

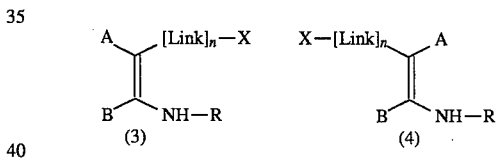

wherein A and B represent the same or different electron-withdrawing group,

X is H or a group which splits off on coupling with oxidised colour developer,

R is an alkyl, cycloalkyl, aryl or heterocyclic group any of which nay be substituted. $—COR^1$, $—CSR^1$, $SOR^1$, $SO_2R^1$, $—NHCOR^1$, $—CONHR^1$, $—COOR^1$, $—COSR^1$. $—NHSO_2R^1$ wherein $R^1$ is an alkyl, cycloalkyl, or aryl group any of which are optionally substituted, and wherein two or more of A, B, R, and X optionally form part of a ring, Link is a linking group and n is 0, 1 or 2.

Examples of couplers of the present invention are listed in Table 3 below.

TABLE 3
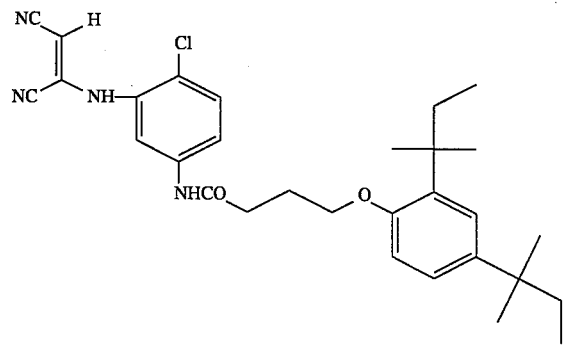 (C-1)
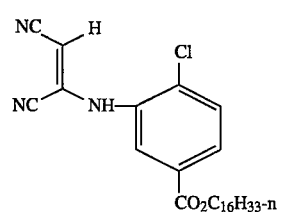 (C-2)
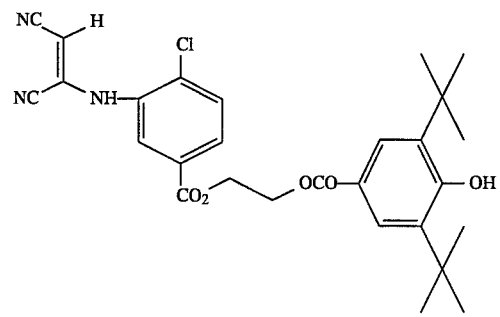 (C-3)
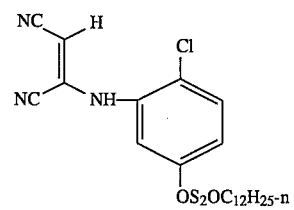 (C-4)
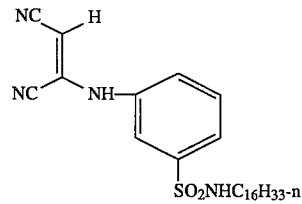 (C-5)
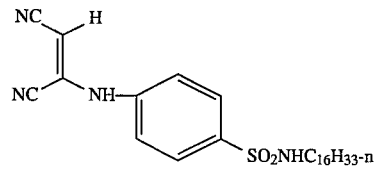 (C-6)

TABLE 3-continued
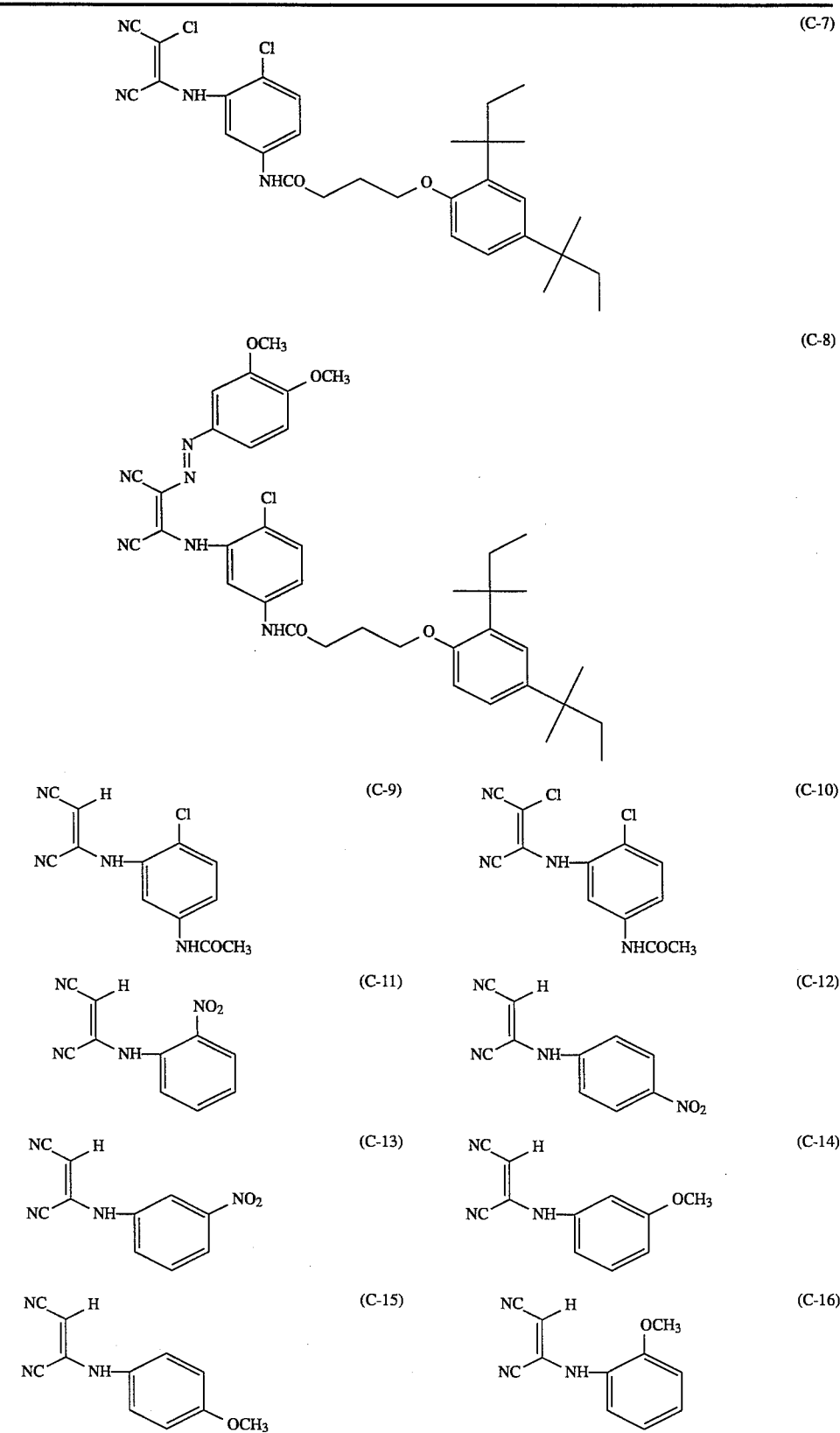

TABLE 3-continued
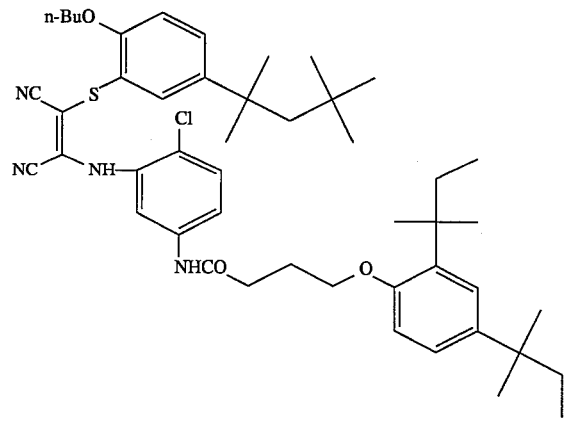
(C-17)
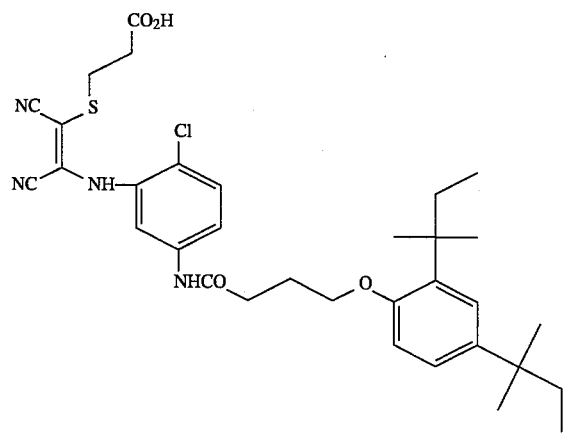
(C-18)
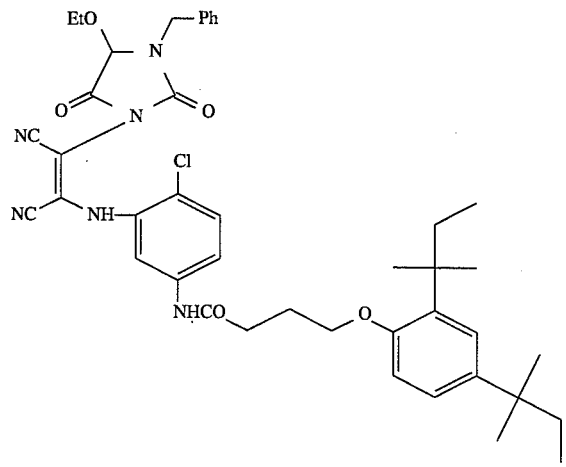
(C-19)

TABLE 3-continued
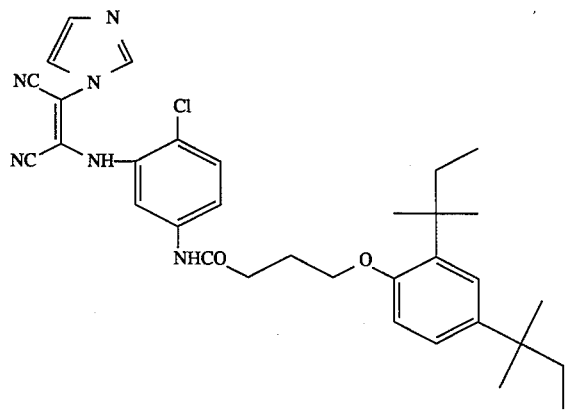
(C-20)
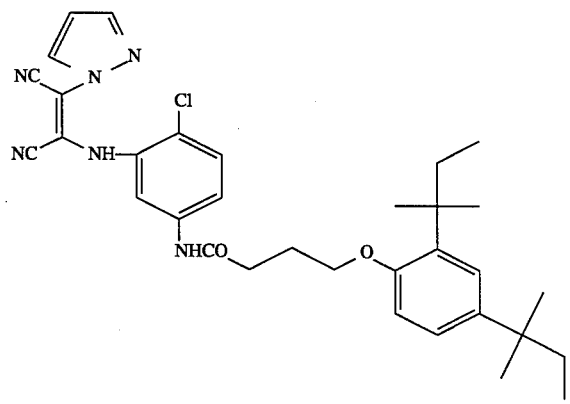
(C-21)
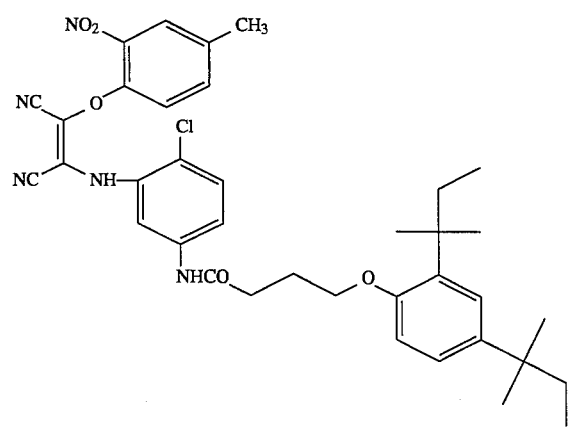
(C-22)
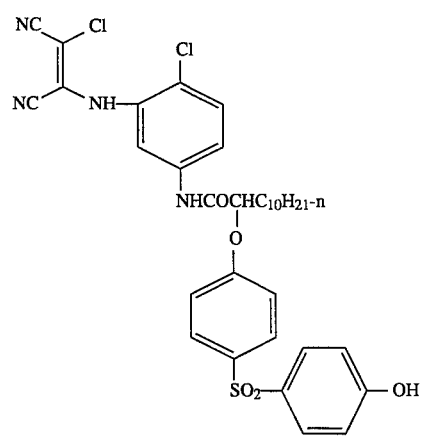
(C-23)

TABLE 3-continued
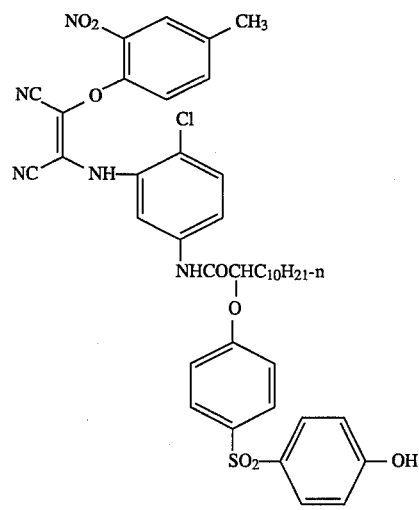
(C-24)
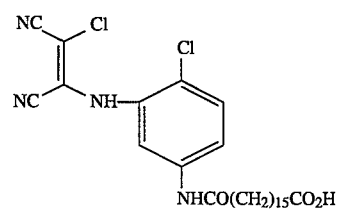
(C-25)
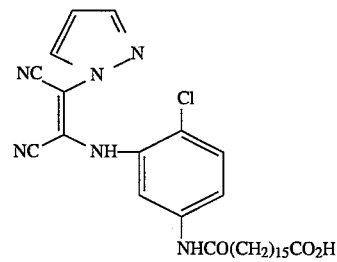
(C-26)
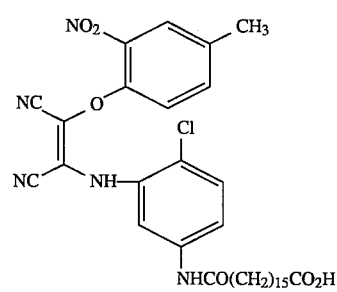
(C-27)
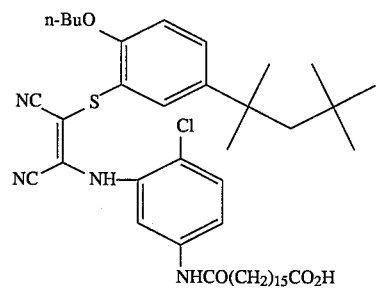
(C-28)

TABLE 3-continued
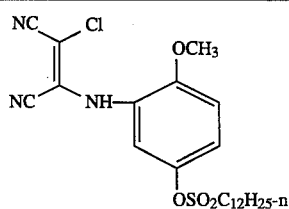
(C-29)
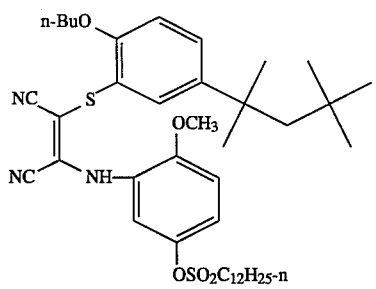
(C-30)
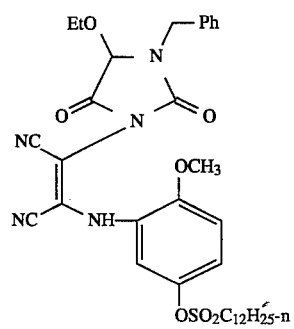
(C-31)
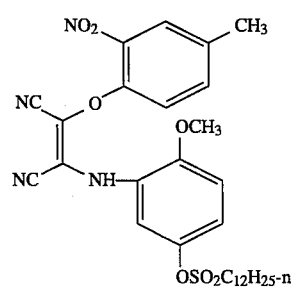
(C-32)
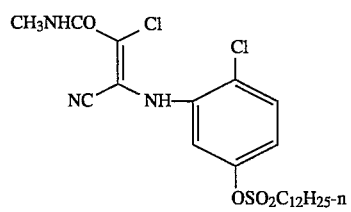
(C-33)
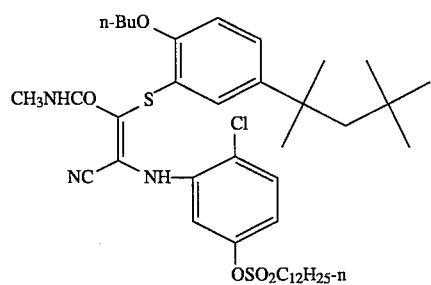
(C-34)

TABLE 3-continued
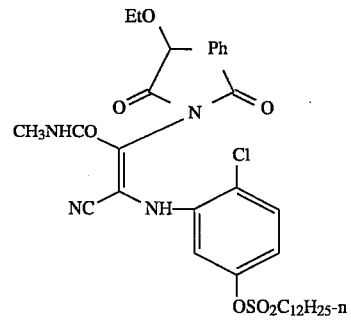 (C-35)
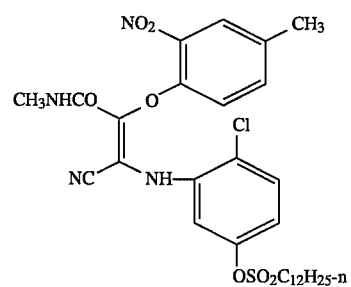 (C-36)
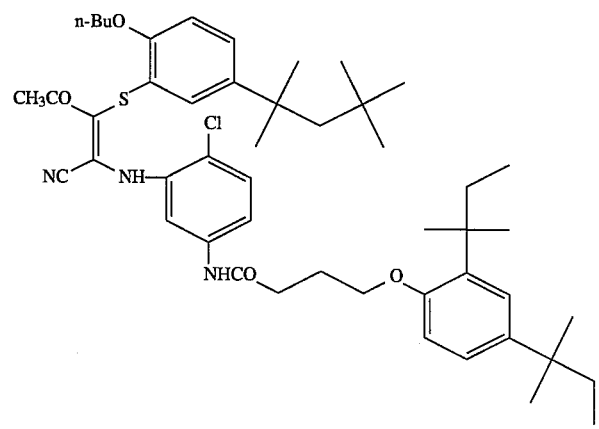 (C-37)
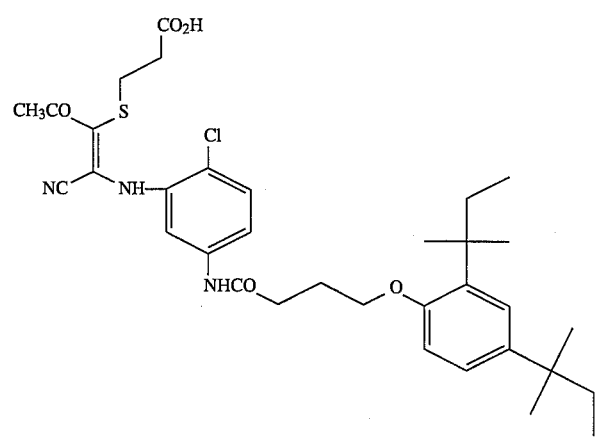 (C-38)

TABLE 3-continued
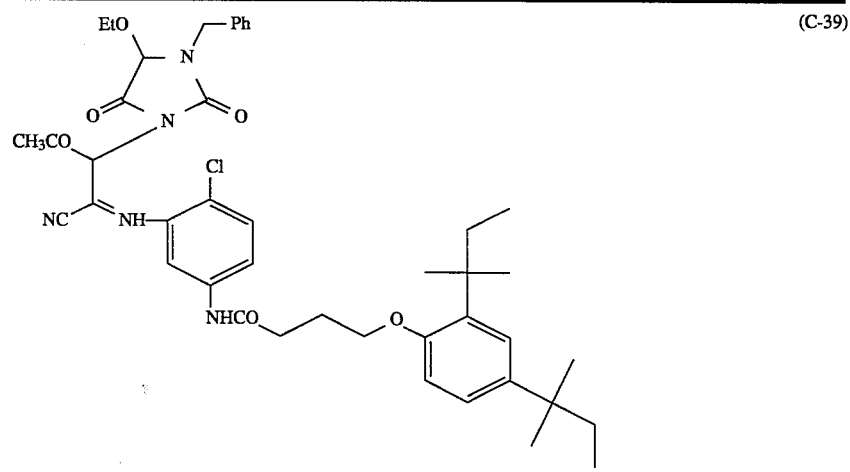
(C-39)
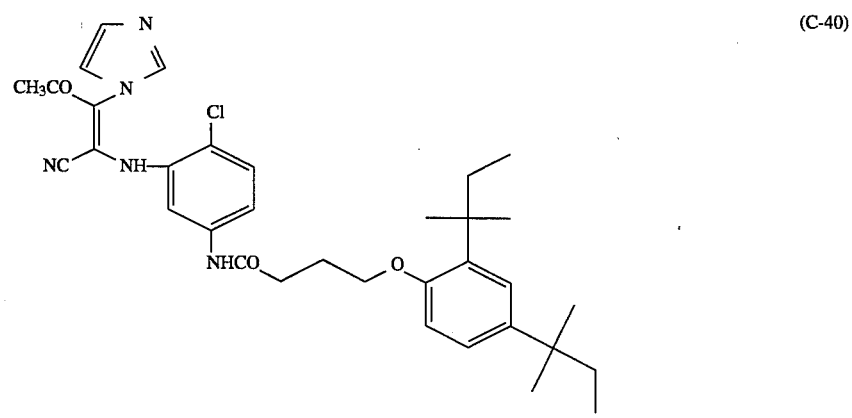
(C-40)
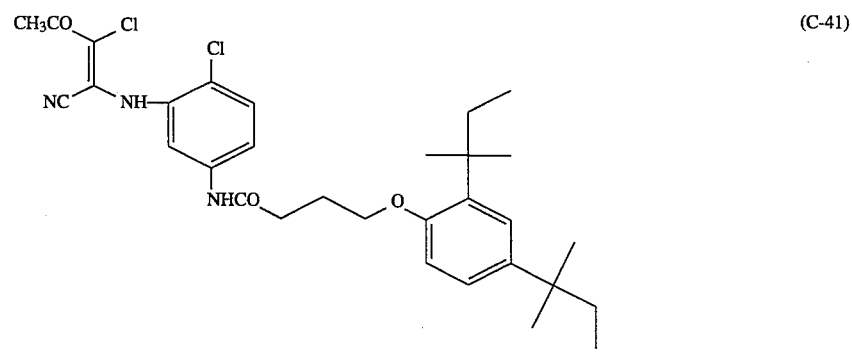
(C-41)
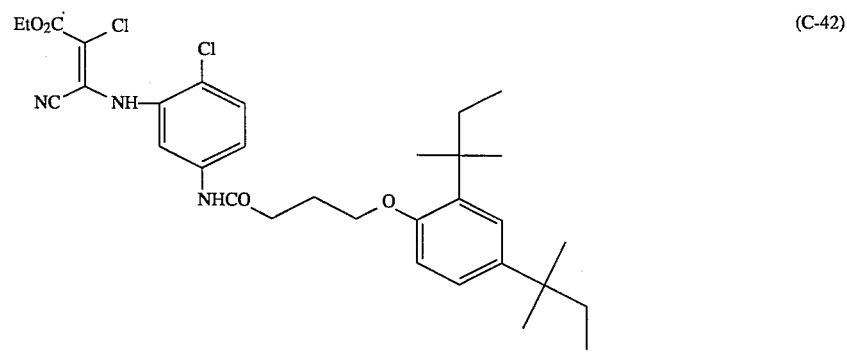
(C-42)

TABLE 3-continued
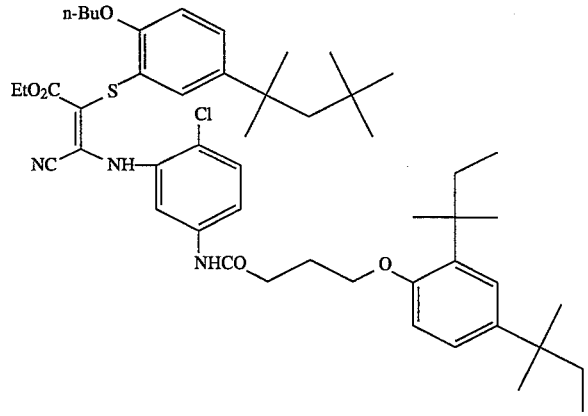
(C-43)
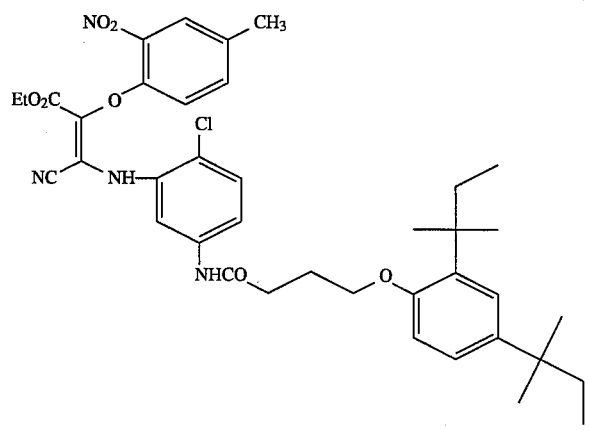
(C-44)
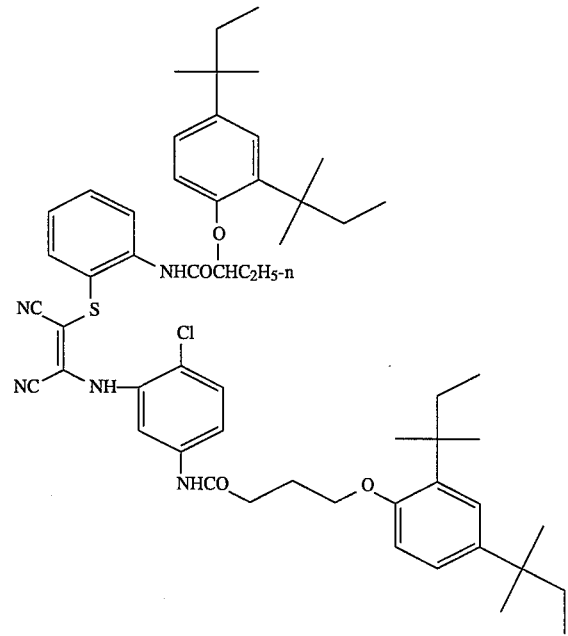
(C-45)

TABLE 3-continued
(C-46)
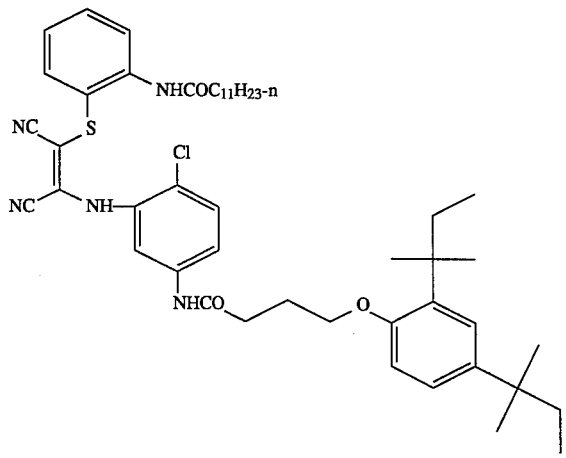
(C-47)
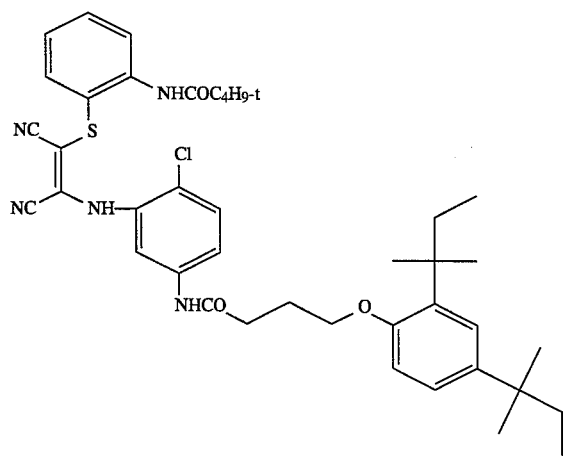
(C-48)
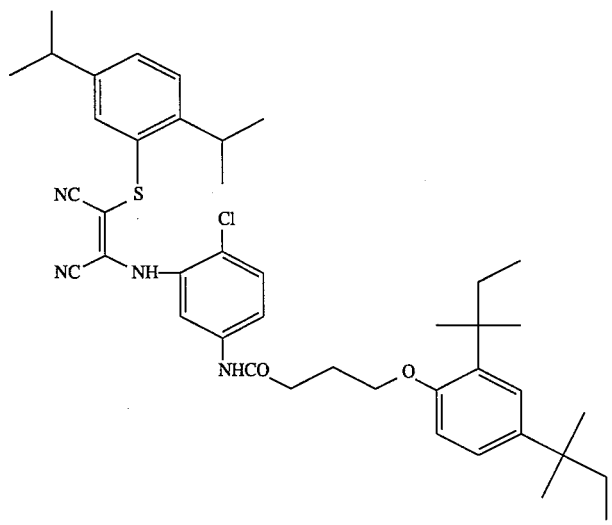

TABLE 3-continued
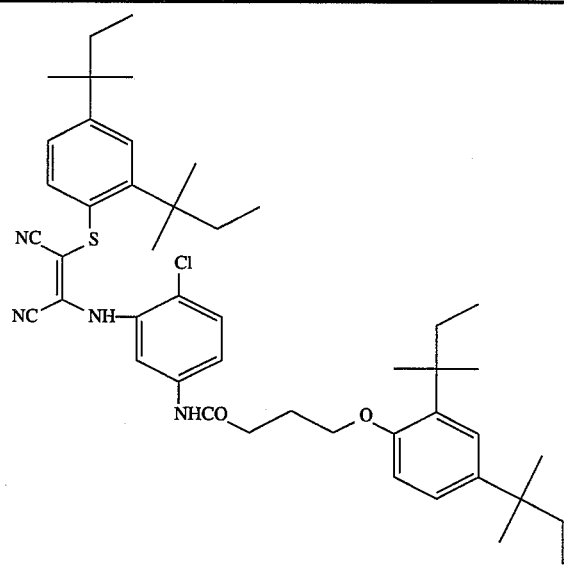
(C-49)
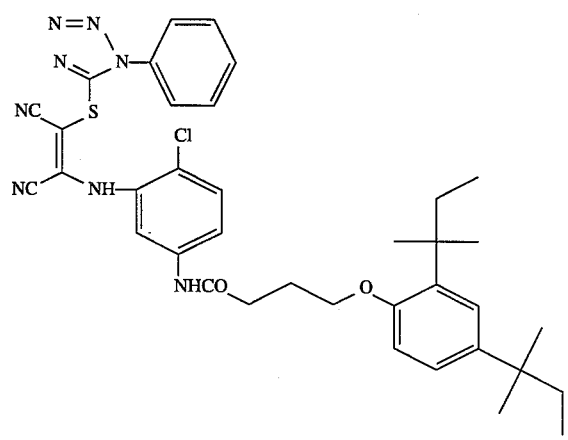
(C-50)
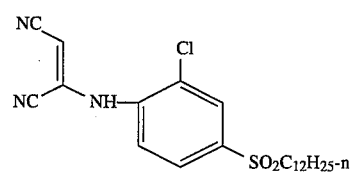
(C-51)
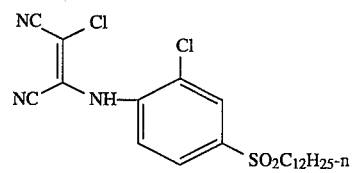
(C-52)

TABLE 3-continued
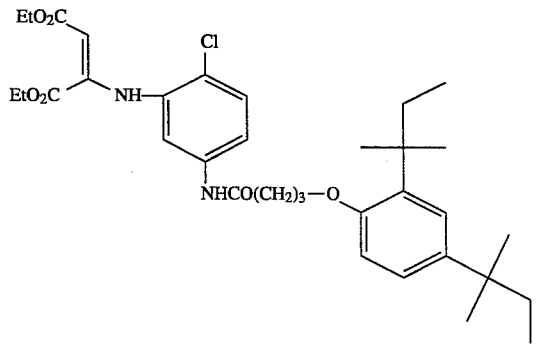
(C-53)
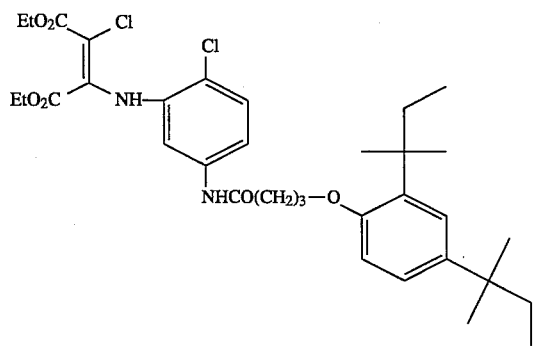
(C-54)
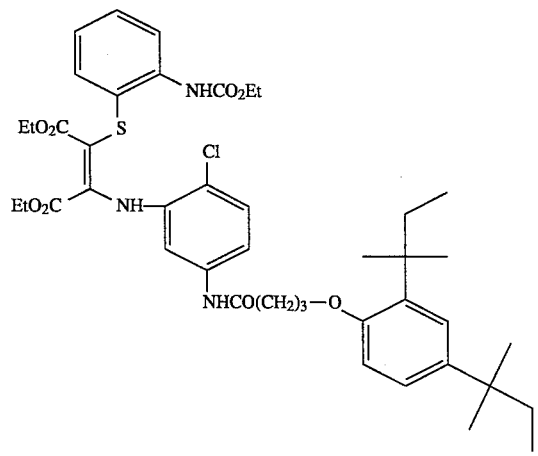
(C-55)
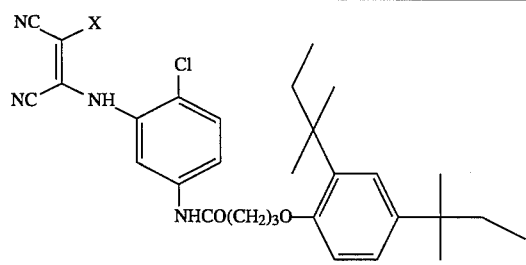
Where X is:-
| C-56 | C-57 | C-58 | C-59 |

TABLE 3-continued
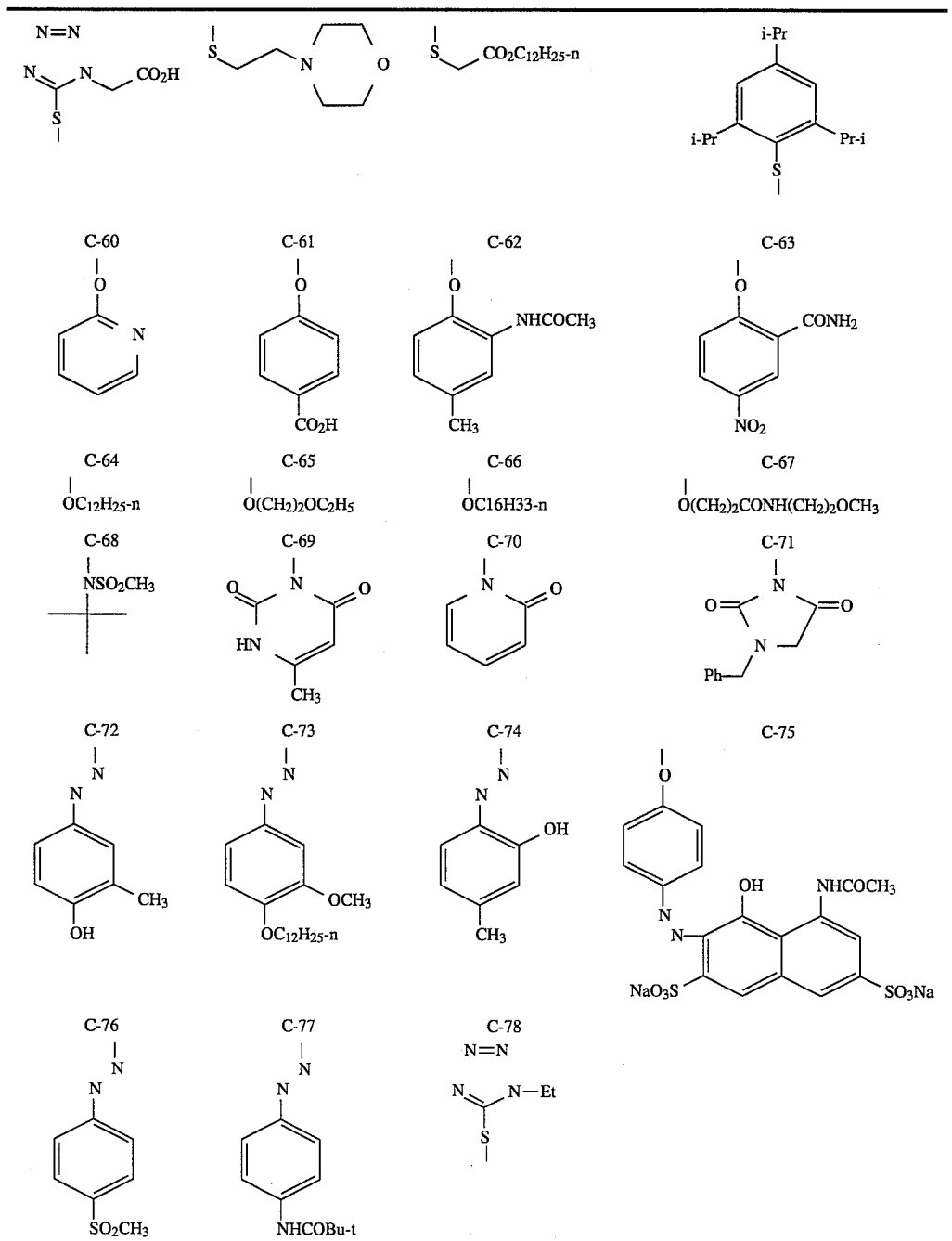
Where X is:-
| C-79 | C-80 | C-81 | C-82 |
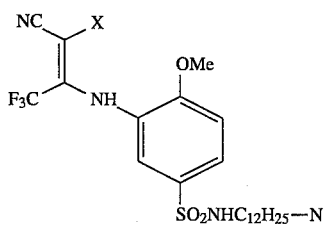

TABLE 3-continued
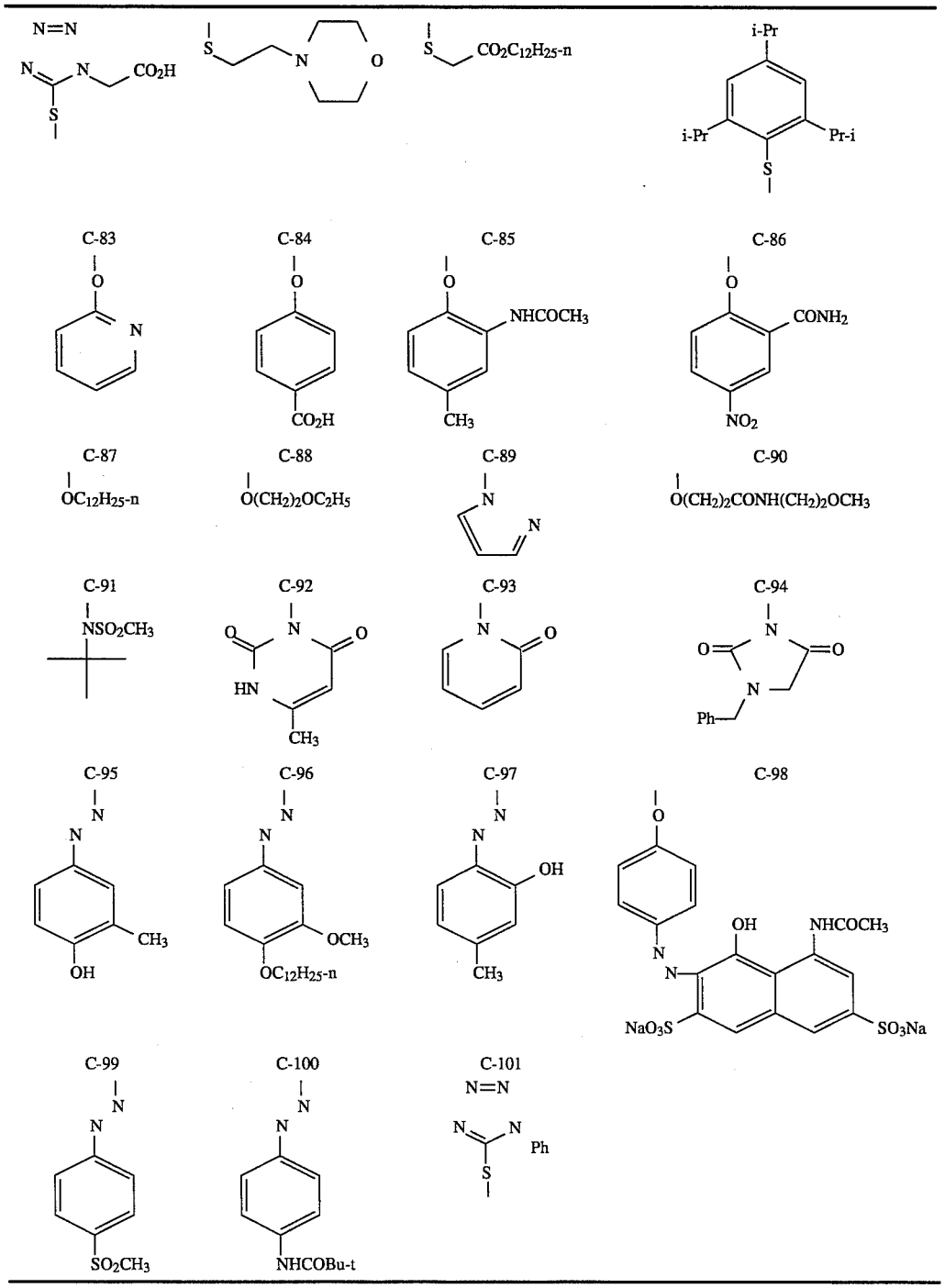
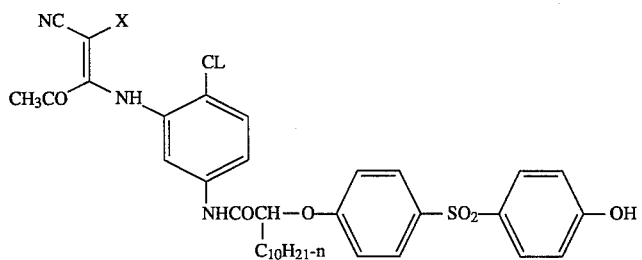

TABLE 3-continued
Where X is:-
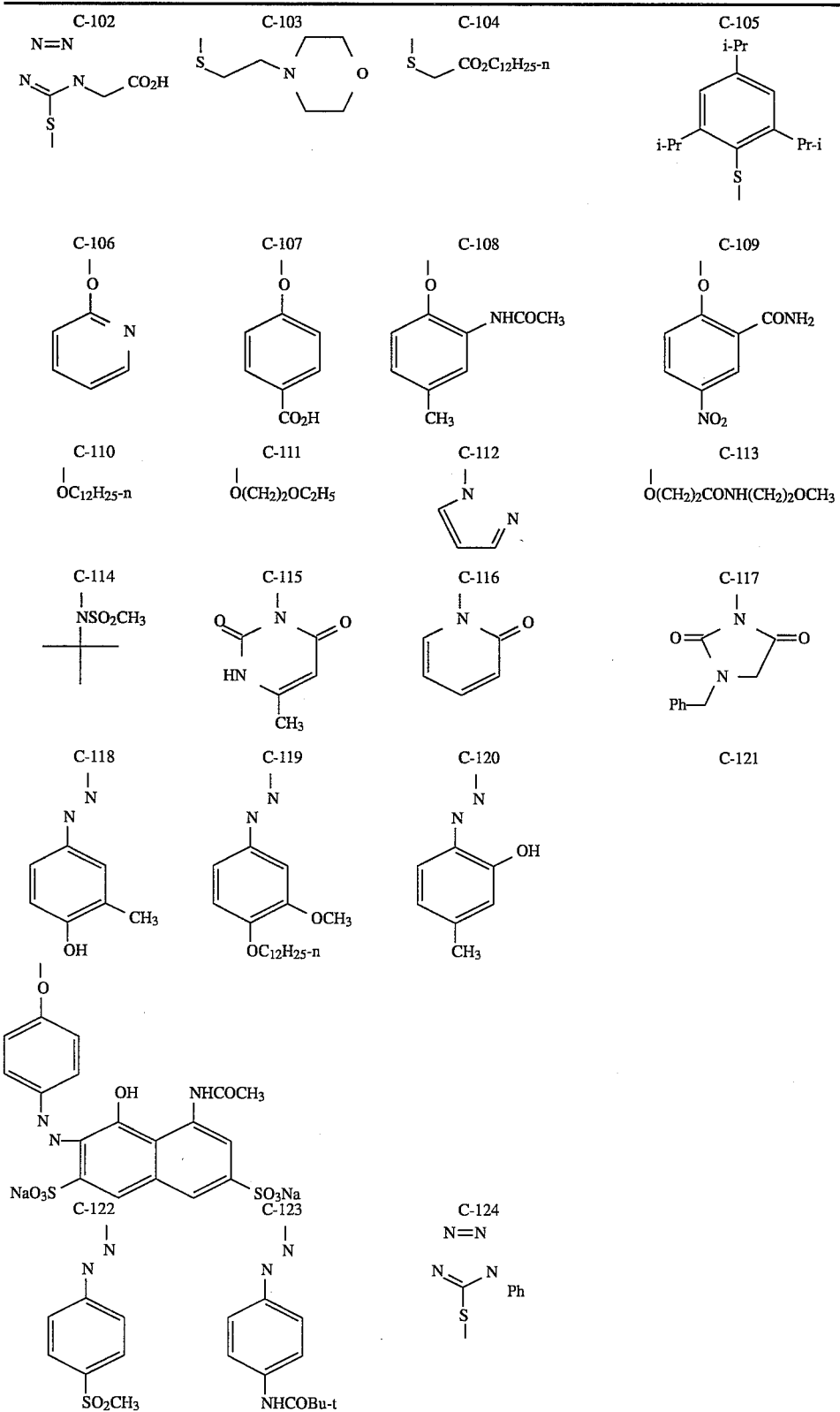

TABLE 3-continued
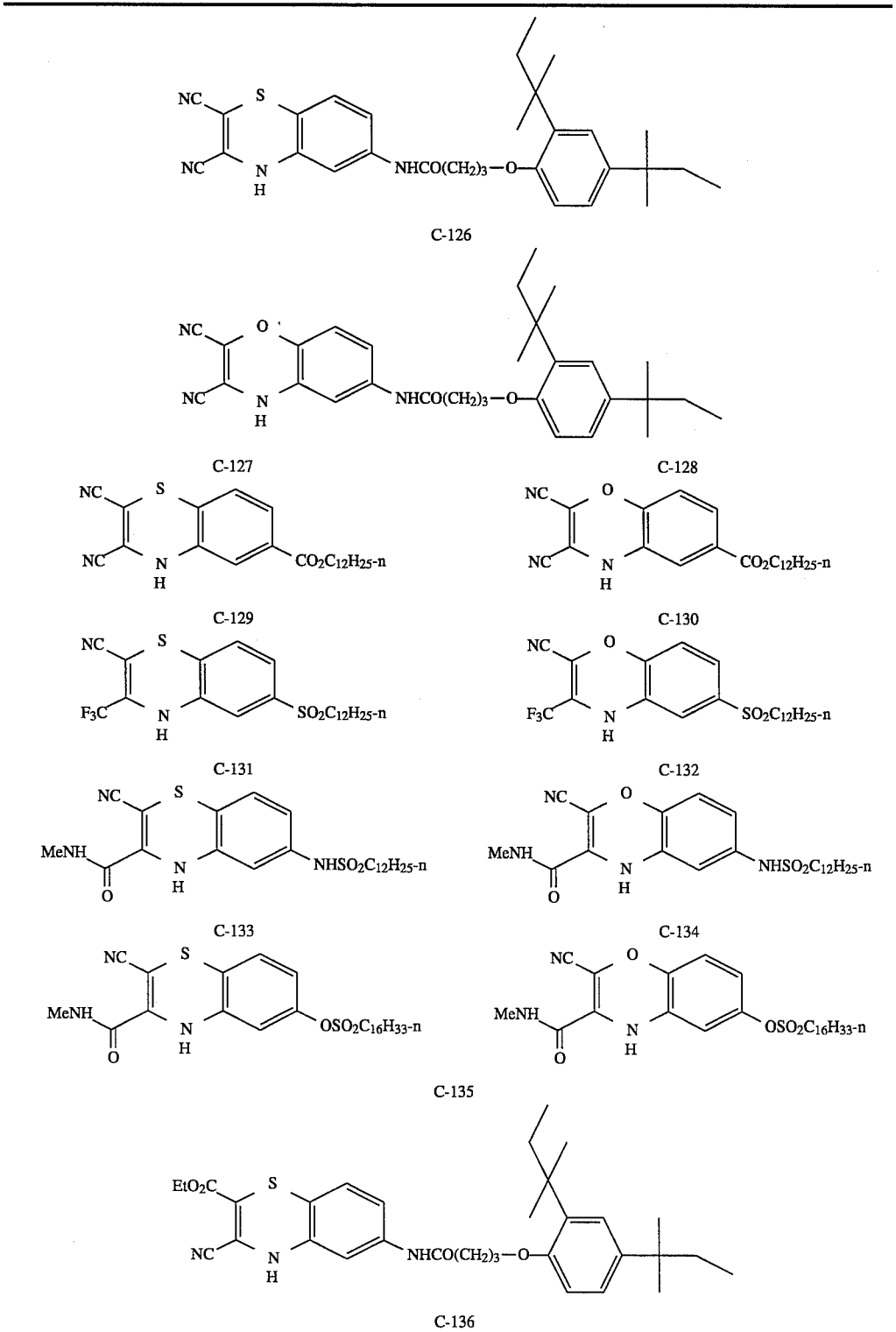

TABLE 3-continued
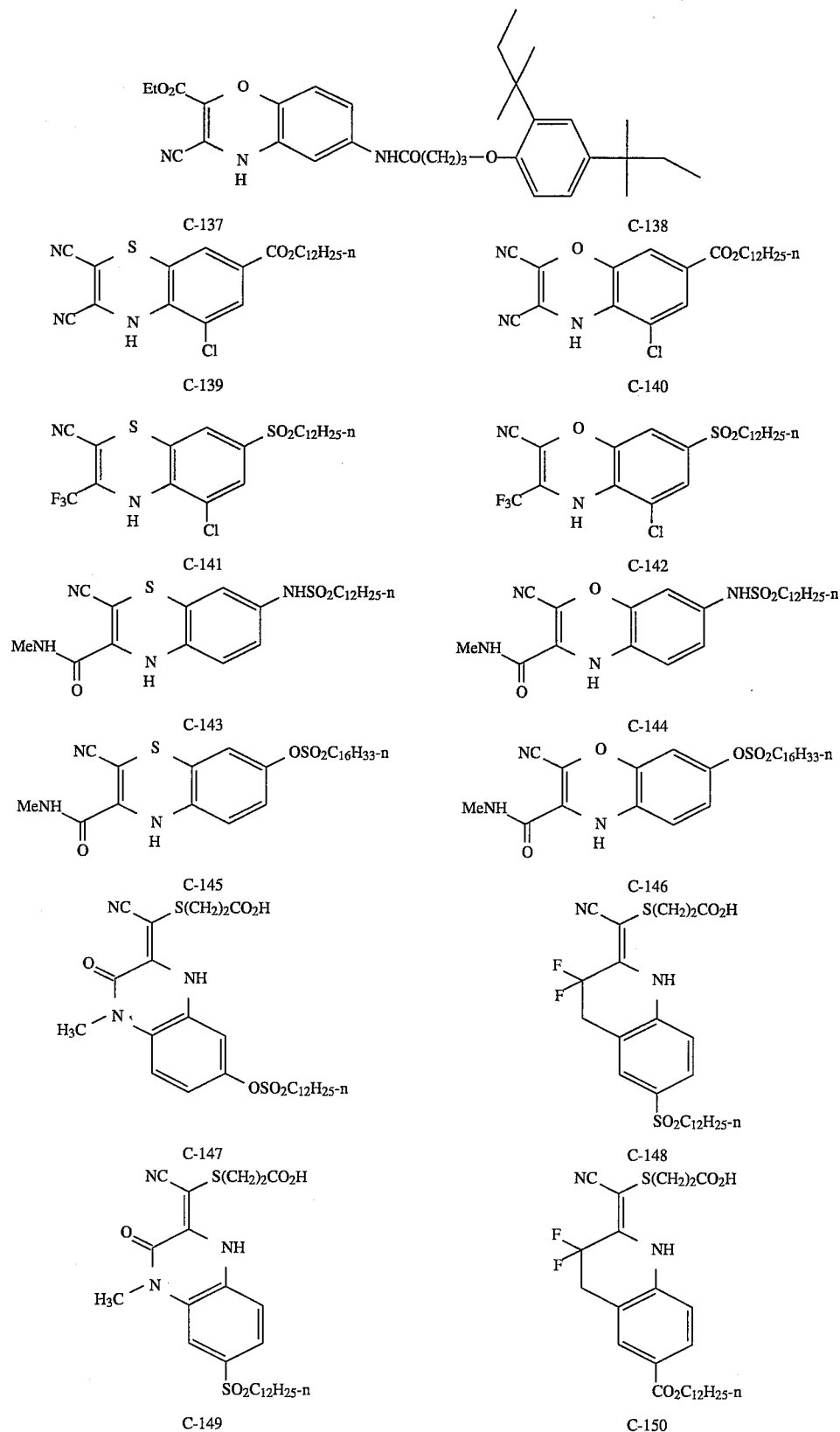

TABLE 3-continued
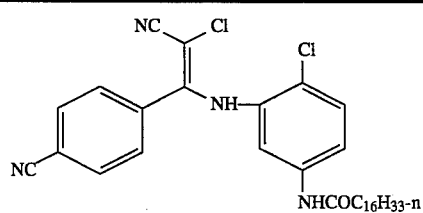
C-151
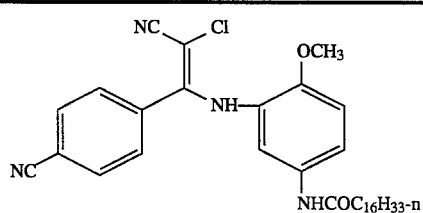
C-152
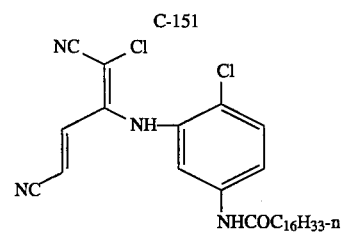
C-153
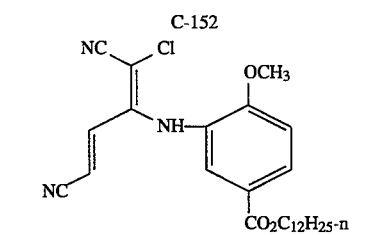
C-154
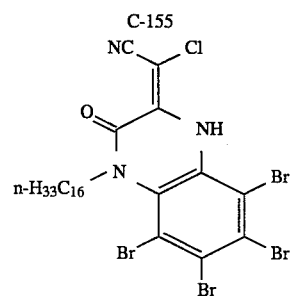
C-155
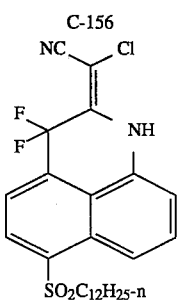
C-156
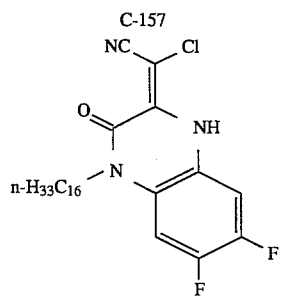
C-157
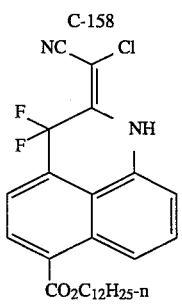
C-158
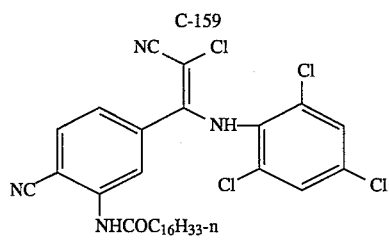
C-161
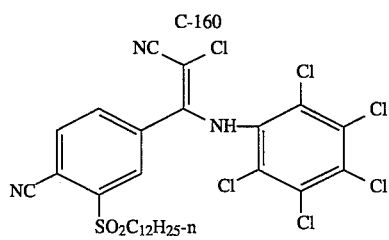
C-162

TABLE 3-continued
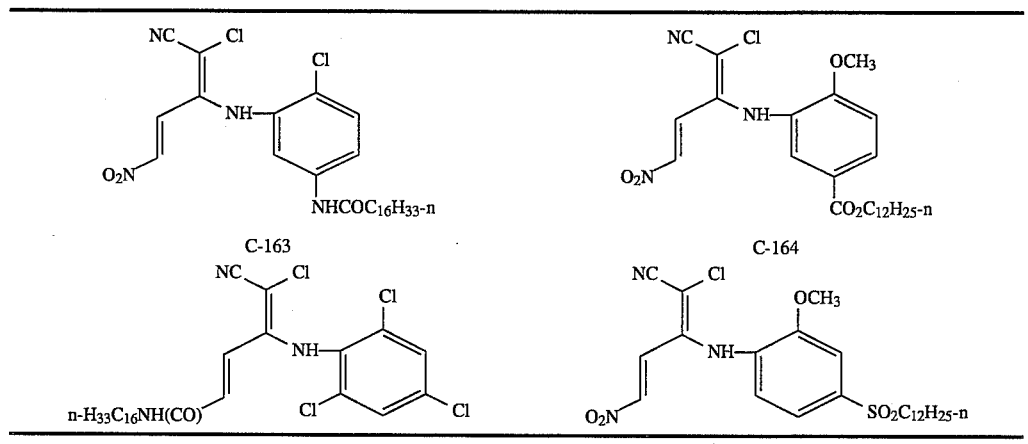
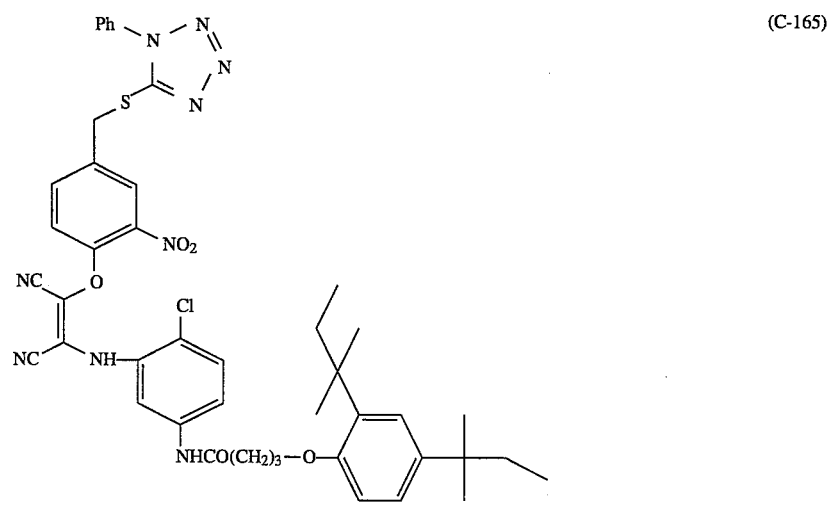
(C-165)
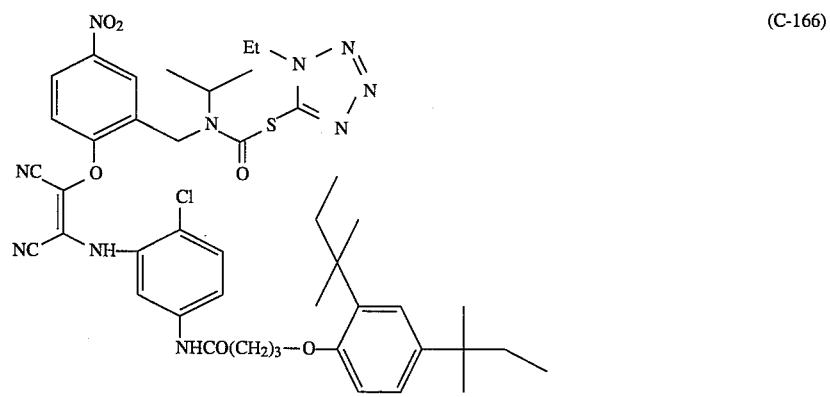
(C-166)

TABLE 3-continued
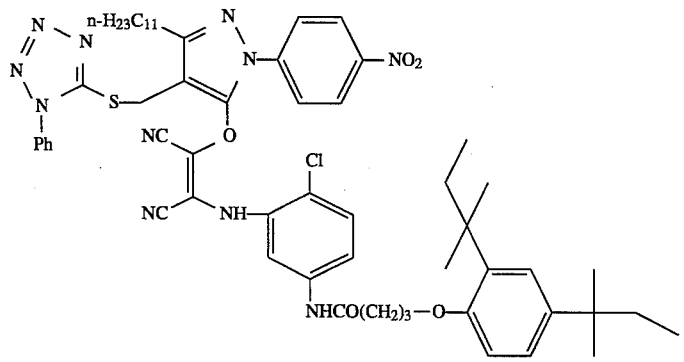
(C-167)
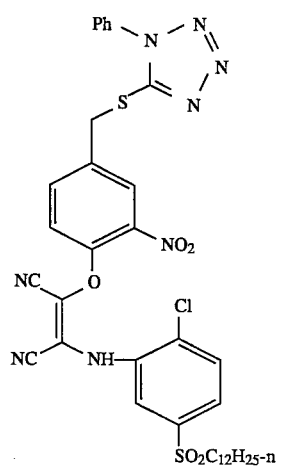
(C-168)
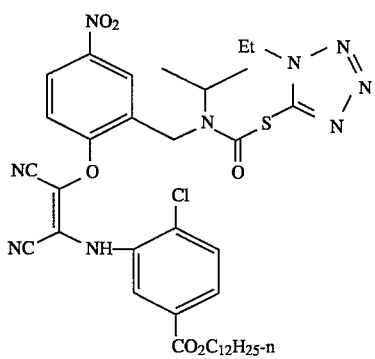
(C-169)
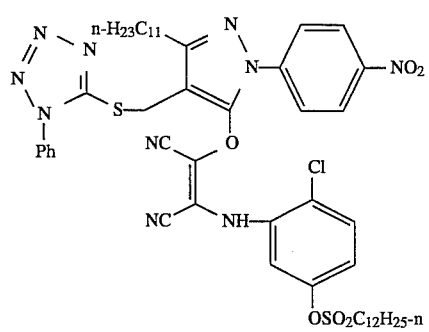
(C-170)

TABLE 3-continued
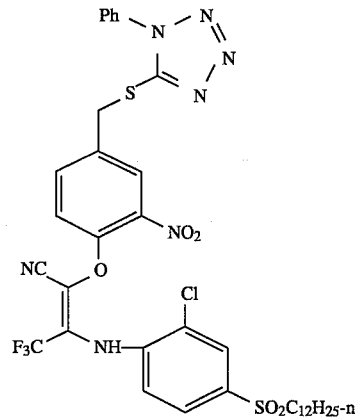
(C-171)
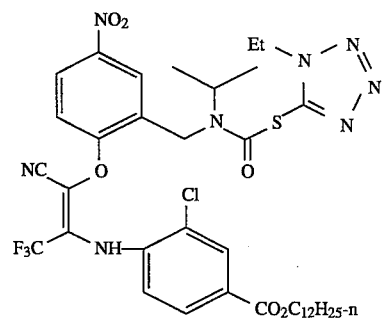
(C-172)
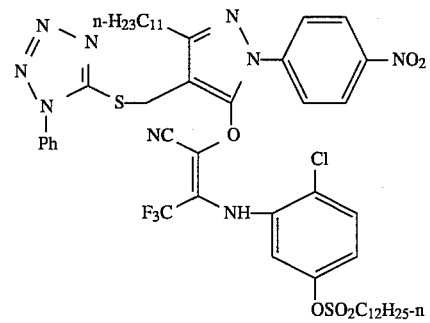
(C-173)
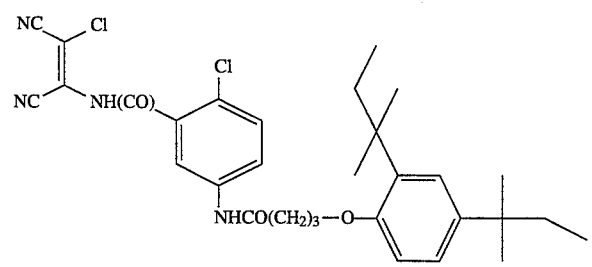
(C-174)
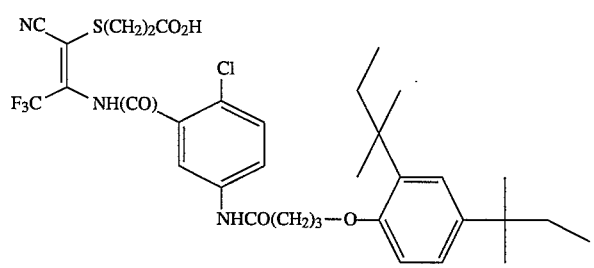
(C-175)

TABLE 3-continued
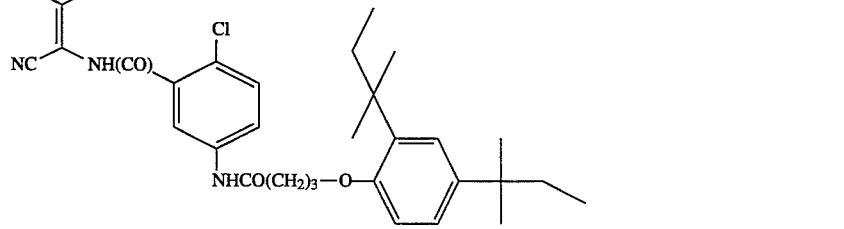
(C-176)
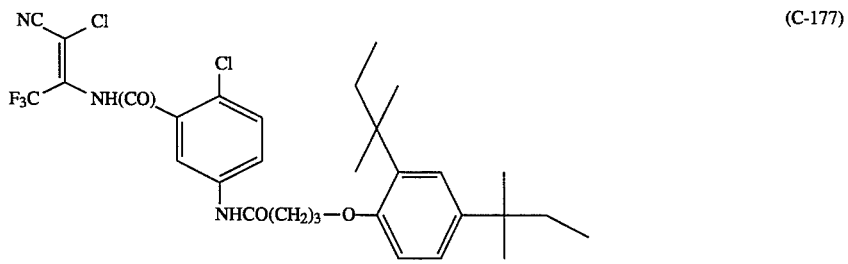
(C-177)
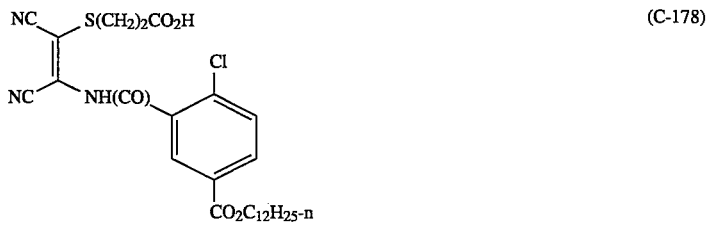
(C-178)
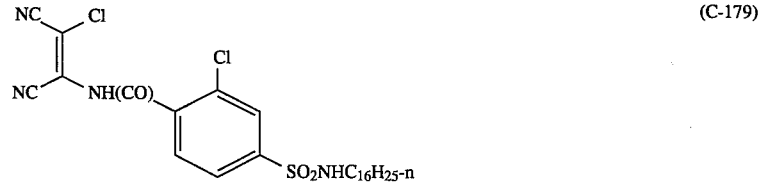
(C-179)
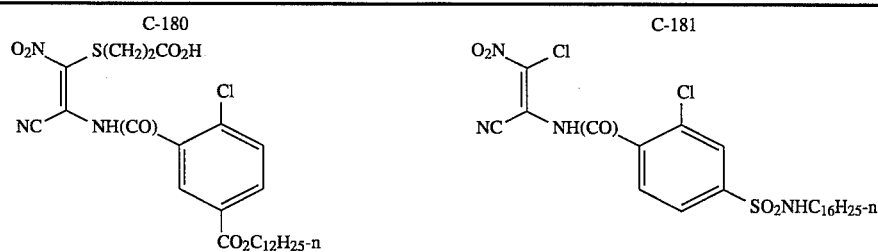
C-180              C-181
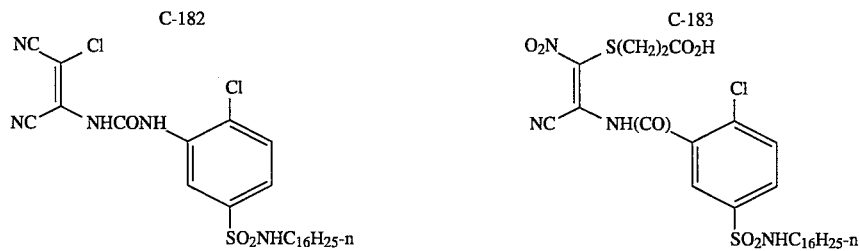
C-182              C-183
C-184              C-185

TABLE 3-continued

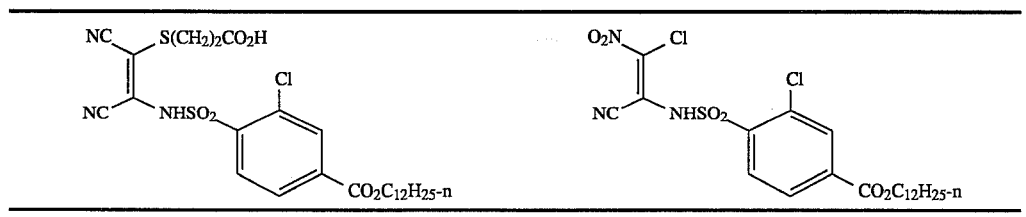

Couplers 53 to 55 above form yellow image dyes whereas the erst all form magenta image dyes.

In addition there are also provided dyes of the formula:

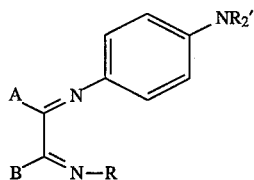

wherein A, B and R are as defined above, and R' is an alkyl or substituted alkyl group.

An example of such a dye is:

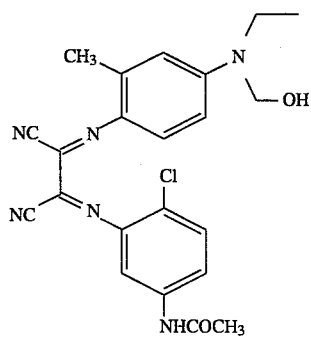

The present colour couplers may be prepared by the following general scheme:

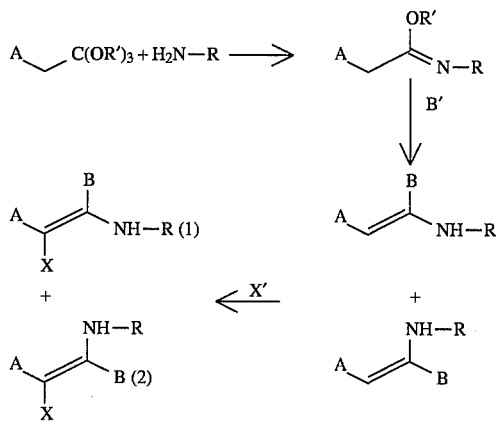

in which B' may be an anionic or neutral species and X' may be an anionic, neutral or cationic species.

The couplers of this invention can be used in any of the ways and in any of the combinations in which couplers are used in the photographic art. Typically, the coupler is incorporated in a silver halide emulsion and the emulsion coated on a support to form part of a photographic element. Alternatively, the coupler can be incorporated at a location adjacent to the silver halide emulsion where, during development, the coupler will be in reactive association with development products such as oxidized color developing agent. Thus, as used herein, the term "associated" signifies that the coupler is in the silver halide emulsion layer or in an adjacent location where, during processing, the coupler is capable of reacting with silver halide development products.

For example, the magenta coupler of the invention may be used to replace all or part of the magenta layer image coupler or may be added to one or more of the other layers in a color negative photographic element comprising a support bearing the following layers from top to bottom:

(1) one or more overcoat layers containing ultraviolet absorber(s);

(2) a two-coat yellow pack with a fast yellow layer containing "Coupler 1": Benzoic acid, 4-chloro- 3-((2-(4-ethoxy-2,5-dioxo-3-(phenylmethyl)-1-imidazolidinyl)-3-(4-methoxyphenyl)-1,3-dioxopropyl)amino)-, dodecyl ester and a slow yellow layer containing the same compound together with "Coupler 2": Propanoic acid, 2-[[5-[[4-[2-[[ [2,4-bis( 1,1-dimethylpropyl)phenoxy]acetyl]amino]-5-[ (2,2,3,3,4,4,4-heptafluoro-1-oxobutyl)amino]-4-hydroxyphenoxy]- 2,3-dihydroxy-6-[(propylamino)carbonyl] phenyl]thio]-1,3,4-thiadiazol-2-yl]thio]-, methyl ester and "Coupler 3": 1-((dodecyloxy)carbonyl) ethyl (3-chloro-4-((3-(2-chloro-4-((1-tridecanoylethoxy) carbonyl)anilino)-3-oxo-2-(( 4) (5) (6)-(phenoxycarbonyl)-1H-benzotriazol-1-yl)propanoyl)amino))benzoate;

(3) an interlayer containing fine metallic silver;

(4) a triple-coat magenta pack with a fast magenta layer containing "Coupler 4": Benzamide, 3-(( 2-(2,4-bis(1,1-dimethylpropyl)phenoxy)-1-oxobutyl)amino)-N-( 4,5-dihydro-5-oxo-1-(2,4,6-trichlorophenyl)- 1H-pyrazol-3-yl) -, "Coupler 5": Benzamide, 3-((2-(2,4-bis(1,1-dimethylpropyl)phenoxy)- 1-oxobutyl)amino)-N-(4',5'-dihydro-5'-oxo-1'-(2,4,6-trichlorophenyl) (1,4'-bi-1H-pyrazol)-3'-yl)-, "Coupler 6": Carbamic acid, (6-(((3-(dodecyloxy)propyl) amino)carbonyl)-5-hydroxy-1-naphthalenyl)-, 2-methylpropyl ester, "Coupler 7": Acetic acid, ((2-((( 3-(((3- (dodecyloxy)propyl)amino) carbonyl)-4-hydroxy- 8-(((2-methylpropoxy)carbonyl) amino)-1-naphthalenyl)oxy)ethyl)thio)-, and "Coupler 8" Benzamide, 3-((2-(2,4-bis (1,1-dimethylpropyl) phenoxy)-1-oxobutyl)amino)-N-(4,5-dihydro-4-((4-methoxyphenyl) azo)-5-oxo-1-(2,4,6-trichlorophenyl)-1 H-pyrazol-3-yl)-; a mid-magenta layer and a slow magenta layer each containing "Coupler 9": 2-Propenoic acid, butyl ester, styrene, 2:1:1 polymer with (N[1-( 2,4,6-trichlorophenyl)-4,5-dihydro-5-oxo-1H-pyrazol- 3-yl]-2-methyl-2-propenamide)$_2$ and "Coupler 10": Tetradecanamide, N-(4-chloro-3-((4-((4-((2,2-dimethyl-1-oxopropyl)amino)phenyl)azo)-4,5-dihydro-5-oxo-1-( 2,4, 6-trichlorophenyl)-1H-pyrazol-3-yl)amino)phenyl)-, in addition to Couplers 3 and 8;

(5) an interlayer;

(6) a triple-coat cyan pack with a fast cyan layer containing Couplers 6 and 7; a mid-cyan containing Coupler 6 and "Coupler 11": 2,7-Naphthalenedisulfonic acid, 5-(acetylamino)-3-((4-(2-((3-(((3-( 2,4-bis(1,1-dimethylpropyl)phenoxy) propyl)amino)carbonyl)-4-hydroxy-1-naphthalenyl)oxy)ethoxy)phenyl)azo)-4-hydroxy-, disodium salt; and a slow cyan layer containing Couplers 2 and 6;

(7) an undercoat layer containing Coupler 8; and (8) an antihalation layer.

In a color paper format, the magenta coupler of the invention may suitably be used to replace all or a part of the magenta coupler in a photographic element such as one comprising a support bearing the following from top to bottom:

(1) one or more overcoats;

(2) a cyan layer containing "Coupler 1": Butanamide, 2-(2,4-bis(1,1-dimethylpropyl)phenoxy)-N-( 3,5-dichloro-2-hydroxy-4-methylphenyl)-, "Coupler 2": Acetamide, 2-(2,4-bis(1,1-dimethylpropyl)phenoxy)-N-( 3,5-dichloro-2-hydroxy-4-, and UV Stabilizers: Phenol, 2-(5-chloro-2H-benzotriazol-2-yl)-4,6-bis(1,1-dimethylethyl)-;Phenol, 2-(2H-benzotriazol-2-yl)-4-( 1,1-dimethylethyl)-;Phenol, 2-(2H-benzotriazol-2-yl)- 4- (1,1-dimethylethyl)-6-(1-methylpropyl)-; and Phenol; 2-(2H-benzotriazol-2-yl)-4,6-bis (1,1-dimethylpropyl)- and a poly(t-butylacrylamide) dye stabilizer;

(3) an interlayer;

(4) a magenta layer containing "Coupler 3": Octanamide, 2-[2,4-bis(1,1-dimethylpropyl)phenoxy]-N-[ 2-(7-chloro-6-methyl-1H-pyrazolo[ 1,5-b] [1,2,4]triazol-2-yl)propyl]-together with 1,1-Spirobi(1 1H-indene), 2,2', 3,3'-tetrahydro-3,3,3',3'-tetramethyl- 5,5',6,6'-tetrapropoxy-;

(5) an interlayer; and (6) a yellow layer sontaining "Coupler 4": 1Imidazolidineacetamide, N-(5-((2-(2,4-bis(1,1-dimethylpropyl))phenoxy)-1-oxobutyl)amino)-2-chorophenyl)-.alpha.-( 2,2-dimethyl-1-oxopropyl)-4-ethoxy-2,5-dioxo-3-(phenylmethyl)-.

In a reversal medium, the magenta coupler of the invention could be used to replace all or part of the magenta coupler in a photographic element such as one comprising a support and bearing the following layers from top to bottom:

(1) one or more overcoat layers;

(2) a nonsensitized silver halide containing layer;

(3) a triple-coat yellow layer pack with a fast yellow layer containing "Coupler 1": Benzoic acid, 4-( 1-(((2-chloro-5-((dodecylsulfonyl)amino)phenyl) amino)carbonyl)-3,3-dimethyl-2-oxobutoxy)-, 1-methylethyl ester; a mid yellow layer containing Coupler 1 and "Coupler 2": Benzoic acid, 4-chloro-3-[ [2-[4-ethoxy-2,5-dioxo-3-(phenylmethyl)-1-imidazolidinyl]- 4,4-dimethyl-1,3-dioxopentyl]amino]-, dodecylester; and a slow yellow layer also containing Coupler 2;

(4) an interlayer;

(5) a layer of fine-grained silver;

(6) an interlayer;

(7) a triple-coated magenta pack with a fast magenta layer containing "Coupler 3": 2-Propenoic acid, butyl ester, polymer with N-[1-(2,5-dichlorophenyl)- 4,5-dihydro-5-oxo-1H-pyrazol-3-yl]-2-methyl- 2-propenamide; "Coupler 4": Benzamide, 3-((2-( 2,4-bis (1,1-dimethylpropyl)phenoxy)-1-oxobutyl)amino)-N-( 4,5-dihydro-5-oxo-1-(2,4,6-trichlorophenyl)- 1H-pyrazol-3-yl)-; and "Coupler 5": Benzamide, 3-(((2,4-bis(1,1-dimethylpropyl)phenoxy)acetyl)amino)-N-( 4,5-dihydro-5-oxo- 1-(2,4,6-trichlorophenyl)-1H-pyrazol-3-yl)-; and containing the stabilizer 1,1'-Spirobi(1H-indene), 2,2',3,3'-tetrahydro-3,3,3',3'-tetramethyl-5,5',6,6'-tetrapropoxy-; and in the slow magenta layer Couplers 4 and 5 with the same stabilizer;

(8) one or more interlayers possibly including fine-grained nonsensitized silver halide;

(9) a triple-coated cyan pack with a fast cyan layer containing "Coupler 6": Tetradecanamide, 2-(2-cyanophenoxy)-N-( 4-((2,2,3,3,4,4,4-heptafluoro-1-oxobutyl)amino)-3-hydroxyphenyl)-; a mid cyan containing "Coupler 7": Butanamide, N-(4-((2-(2,4-bis( 1,1-dimethylpropyl)phenoxy)-1-oxobutyl)amino)-2-hydroxyphenyl)- 2,2,3,3,4,4,4-heptafluoro- and "Coupler 8": Hexanamide, 2-(2,4-bis(1,1-dimethylpropyl)phenoxy)-N-( 4-((2,2,3,3,4,4,4-heptafluoro-1-oxobutyl)amino)-3-hydroxyphenyl)-;

(10) one or more interlayers possibly including fine-grained nonsensitized silver halide; and

(11) an antihalation layer.

It is common to include ballast or "BALL" substituents in the coupler. Representative BALL groups are of such size and configuration as to confer on the coupler molecule sufficient bulk to render the coupler substantially non-diffusible from the layer in which it is coated in the described photographic recording material.

Representative ballast groups include substituted or unsubstituted alkyl or aryl groups containing 8 to 40 carbon atoms.

Representative substituents on such groups include alkyl, aryl, alkoxy, aryloxy, alkylthio, hydroxy, halogen, alkoxycarbonyl, aryloxcarbonyl, carboxy, acyl, acyloxy, amino, anilino, carbonamido, carbamoyl, alkylsulfonyl, arysulfonyl, sulfonamido, and sulfamyl groups wherein the substituents typically contain 1 to 40 carbon atoms. Such substituents can also be further substituted.

The photographic elements can be single color elements or multicolor elements. Multicolor elements contain dye image-forming units sensitive to each of the three primary regions of the spectrum. Each unit can be comprised of a single emulsion layer or of multiple emulsion layers sensitive to a given region of the spectrum. The layers of the element, including the layers of the image-forming units, can be arranged in various orders as known in the art. In a alternative format, the emulsions sensitive to each of the three primary regions of the spectrum can be disposed as a single segmented layer.

A typical multicolor photographic element comprises a support bearing a cyan dye image-forming unit comprised of at least one red-sensitive silver halide emulsion layer having associated therewith at least one cyan dye-forming coupler, a magenta dye image-forming unit comprising at least one green-sensitive silver halide emulsion layer having associated therewith at least one magenta dye-forming coupler, and a yellow dye image-forming unit comprising at least one blue-sensitive silver halide emulsion layer having associated therewith at least one yellow dye-forming coupler, at least one of the couplers in the element being a coupler of this invention. The element can contain additional layers, such as filter layers, interlayers, overcoat layers, subbing layers, and the like.

In the following discussion of suitable materials for use in the emulsions and elements of this invention, reference will be made to *Research Disclosure,* December 1989, Item 308119, published by Kenneth Mason Publications, Ltd., Dudley Annex, 12a North Street, Emsworth, Hampshire P010 7DQ, ENGLAND, which will be identified hereafter by the term "Research Disclosure." The contents of the Research Disclosure, including the patents and publications referenced therein, are incorporated herein by reference, and the Sections hereafter referred to are Sections of the Research Disclosure.

The silver halide emulsions employed in the elements of this invention can be either negative-working or positive-working. Suitable emulsions and their preparation as well as methods of chemical and spectral sensitization are described in Sections I through IV. Color materials and development modifiers are described in Sections V and XXI. Vehicles are described in Section IX, and various additives such as brighteners, antifoggants, stabilizers, light absorbing and scattering materials, hardeners, coating aids, plasticizers, lubricants and matting agents are described, for example, in Sections V, VI, VIII, X, XI, XII, and XVI. Manufacturing methods are described in Sections XIV and XV, other layers and supports in Sections XIII and XVII, processing methods and agents in Sections XIX and XX, and exposure alternatives in Section XVIII.

Preferred color developing agents are p-phenylenediamines. Especially preferred are:

4-amino N,N-diethylaniline hydrochloride,
4-amino-3-methyl-N,N-diethylaniline hydrochloride,
4-amino-3-methyl-N-ethyl-N-(b-(methanesulfonamido)ethyl)aniline sesquisulfate hydrate,
4-amino-3-methyl-N-ethyl-N-(b-hydroxyethyl)aniline sulfate,
4-amino-3-b-(methanesulfonamido)ethyl-N,N-diethylaniline hydrochloride and
4-amino-N-ethyl-N-(2-methoxyethyl)-m-toluidine di-p-toluene sulfonic acid.

With negative working silver halide a negative image can be formed. Optionally positive (or reversal) image can be formed.

The magenta coupler described herein may be used in combination with other classes of magenta image couplers such as 3-acylamino-5-pyrazolones and heterocyclic couplers (e.g. pyrazoloazoles) such as those described in EP 285,274; U.S. Pat. No. 4,540,654; EP 119,860, or with other 5-pyrazolone couplers containing different ballasts or coupling-off groups such as those described in U.S. Pat. No. 4,301,235; U.S. Pat. No. 4,853,319 and U.S. Pat. No. 4,351,897. The coupler may also be used in association with yellow or cyan colored couplers (e.g. to adjust levels of interlayer correction) and with masking couplers such as those described in EP 213.490; Japanese Published Application 58-172,647; U.S. Pat. No. 2,983,608; German Application DE 2,706,117C; U.K. Patent 1,530,272; Japanese Application A-113935; U.S. Pat. No. 4,070,191 and German Application DE 2,643. 965. The masking couplers may be shifted or blocked.

The couplers may also be used in association with materials that accelerate or otherwise modify the processing steps e.g. of bleaching or fixing to improve the quality of the image. Bleach accelerators described in EP 193,389; EP 301,477; U.S. Pat. No. 4,163,669; U.S. Pat. No. 4,865,956; and U.S. Pat. No. 4,923,784 are particularly useful. Also contemplated is use of the coupler in association with nucleating agents, development accelerators or their precursors (UK Patent 2,097,140; U.K. Patent 2,131,188); electron transfer agents (U.S. Pat. No. 4,859,578; U.S. Pat. No. 4,912,025); antifogging and anti color-mixing agents such as derivatives of hydroquinones, aminophenols, amines, gallic acid; catechol; ascorbic acid; hydrazides; sulfonamidophenols; and non color-forming couplers.

The couplers may also be used in combination with filter dye layers comprising colloidal silver sol or yellow and/or magenta filter dyes, either as oil-in-water dispersions, latex dispersions or as solid particle dispersions. Additionally, they may be used with "smearing" couplers (e.g. as described in U.S. Pat. No. 4,366,237; EP 96,570; U.S. Pat. No. 4,420,556; and U.S. Pat. No. 4,543,323.) Also, the couplers may be blocked or coated in protected form as described, for example, in Japanese Application 61/258,249 or U.S. Pat. No. 5,019,492.

The coupler may further be used in combination with image-modifying compounds such as "Developer Inhibitor-Releasing" compounds (DIR's). DIR's useful in conjunction with the couplers of the invention are known in the art and examples are described in U.S. Pat. Nos. 3,137,578; 3,148,022; 3,148,062; 3,227,554; 3. 384,657; 3,379,529; 3,615,506; 3,617,291; 3,620,746; 3,701,783; 3,733,201; 4,049,455; 4,095,984; 4,126,459; 4,149,886; 4,150,228; 4,211,562; 4,248,962; 4,259,437: 4,362,878; 4,409,323; 4,477,563; 4,782,012; 4,962,018; 4,500,634; 4,579,816; 4,607,004; 4,618,571; 4,678,739; 4,746,600; 4,746,601; 4,791,049; 4,857,447; 4,865,959; 4,880,342; 4,886,736; 4,937,179; 4,946,767; 4,948,716; 4,952,485; 4,956,269; 4,959,299; 4,966,835; 4,985,336 as well as in patent publications GB 1,560,240; GB 2,007,662; GB 2,032,914; GB 2,099,167; DE 2,842,063, DE 2,937,127; DE 3,636,824; DE 3,644,416 as well as the following European Patent Publications: 272,573; 335,319; 336,411; 346,899; 362,870; 365,252; 365,346; 373,382; 376,212; 377,463; 378,236; 384,670; 396,486; 401,612; 401,613.

Such compounds are also disclosed in "Developer-Inhibitor-Releasing (DIR) Couplers for Color Photography," C. R. Barr, J. R. Thirtle and P. W. Vittum in *Photographic Science and Engineering*, Vol. 13, p. 174 (1969), incorporated herein by reference. Generally, the developer inhibitor-releasing (DIR) couplers include a coupler moiety and an inhibitor coupling-off moiety (IN). The inhibitor-releasing couplers may be of the time-delayed type (DIAR couplers) which also include a timing moiety or chemical switch which produces a delayed release of inhibitor. Examples of typical inhibitor moieties are: oxazoles, thiazoles, diazoles, triazoles, oxadiazoles, thiadiazoles, oxathiazoles, thiatriazoles, benzotriazoles, tetrazoles, benzimidazoles, indazoles, isoindazoles, mercaptotetrazoles, selenotetrazoles, mercaptobenzothiazoles, selenobenzothiazoles, mercaptobenzoxazoles, selenobenzoxazoles, mercaptobenzimidazoles, selenobenzimidazoles, benzodiazoles, mercaptooxazoles, mercaptothiadiazoles, mercaptothiazoles, mercaptotriazoles, mercaptooxadiazoles, mercaptodiazoles, mercaptooxathiazoles, telleurotetrazoles or benzisodiazoles, In a preferred embodiment, the inhibitor moiety or group is selected from the following formulas:

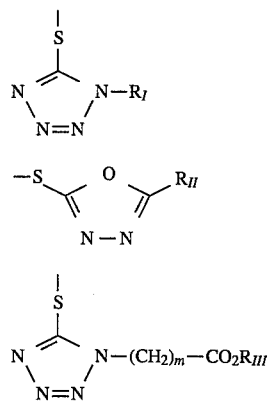

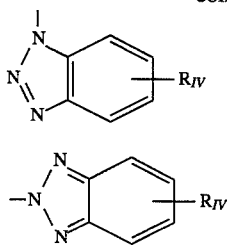

wherein $R_I$ is selected from the group consisting of straight and branched alkyls of from 1 to about 8 carbon atoms, benzyl and phenyl groups and said groups containing at least one alkoxy substituent; $R_{II}$ is selected from $R_I$ and —$SR_I$; $R_{III}$ is a straight or branched alkyl group of from 1 to about 5 carbon atoms and m is from 1 to 3; and $R_{IV}$ is selected from the group consisting of hydrogen, halogens and alkoxy, phenyl and carbonamido groups, —$COOR_V$ and —NHCO-$OR_V$ wherein $R_V$ is selected from substituted and unsubstituted alkyl and aryl groups.

Although it is typical that the coupler moiety included in the developer inhibitor-releasing coupler forms an image dye corresponding to the layer in which it is located, it may also form a different color as one associated with a different film layer. It may also be useful that the coupler moiety included in the developer inhibitor-releasing coupler forms colorless products and/or products that wash out of the photographic material during processing (so-called "universal" couplers).

As mentioned, the developer inhibitor-releasing coupler may include a timing group which produces the time-delayed release of the inhibitor group such as groups utilizing the cleavage reaction of a hemiacetal (U.S. Pat. No. 4,146,396, Japanese Applications 60-249148; 60- 249149); groups using an intramolecular nucleophilic substitution reaction (U.S. Pat. No. 4,248,962); groups utilizing an electron transfer reaction along a conjugated system (U.S. Pat. Nos. 4,409,323; 4,421,845; Japanese Applications 57-188035; 58-98728; 58-209736; 58- 209738) groups utilizing ester hydrolysis (German Patent Application (OLS) No. 2,626,315; groups utilizing the cleavage of imino ketals (U.S. Pat. No. 4,546,073); groups that function as a coupler or reducing agent after the coupler reaction (U.S. Pat. No. 4,438,193; U.S. Pat. No. 4,618,571) and groups that combine the features describe above. It is typical that the timing group or moiety is of one of the formulas:

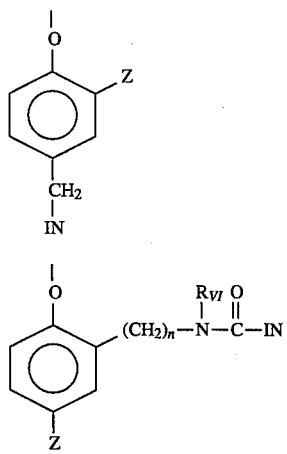

wherein IN is the inhibitor moiety, Z is selected from the group consisting of nitro, cyano, alkylsulfonyl; sulfamoyl (—$SO_2NR_2$); and sulfonamido (—$NRSO_2R$) groups; n is 0 or 1; and $R_{VI}$ is selected from the group consisting of substituted and unsubstituted alkyl and phenyl groups. The oxygen atom of each timing group is bonded to the coupling-off position of the respective coupler moiety of the DIAR.

Suitable developer inhibitor-releasing couplers for use in the present invention include, but are not limited to, the following:

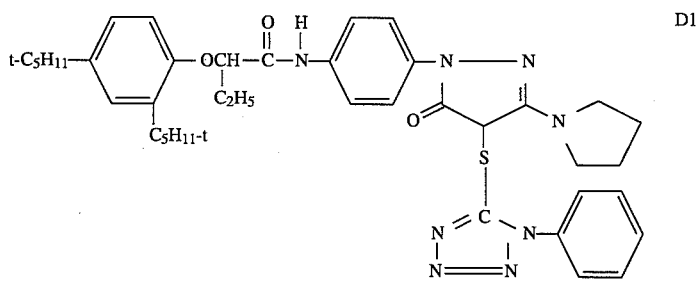

D1

-continued
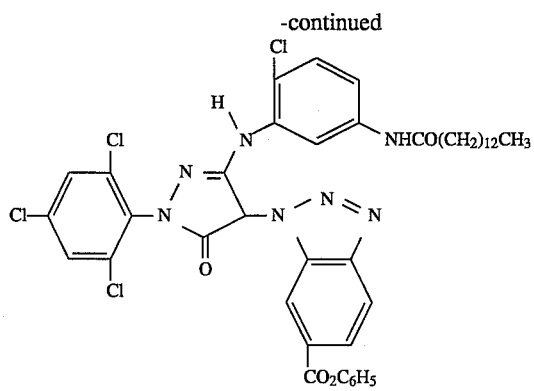
D2
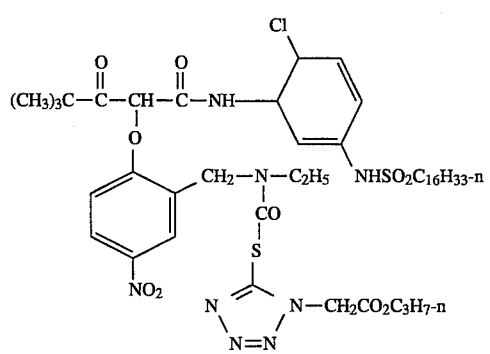
D3
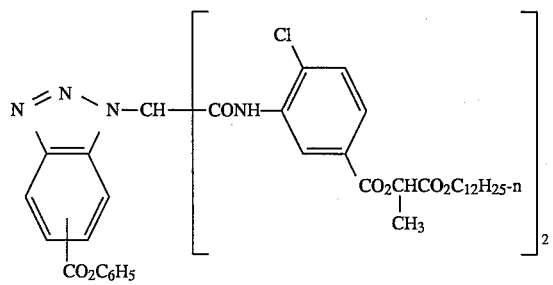
D4
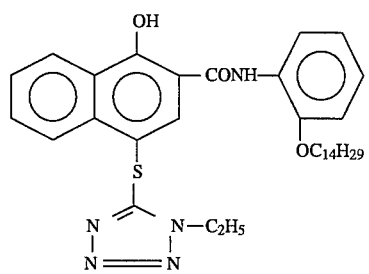
D5

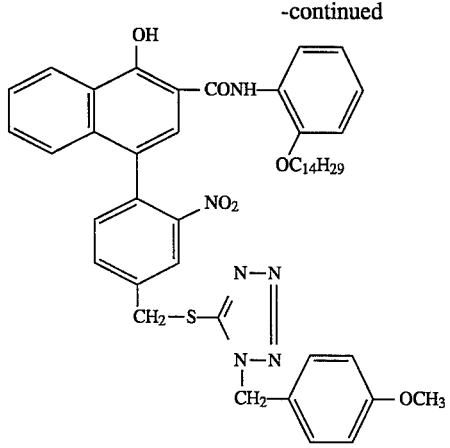

D6

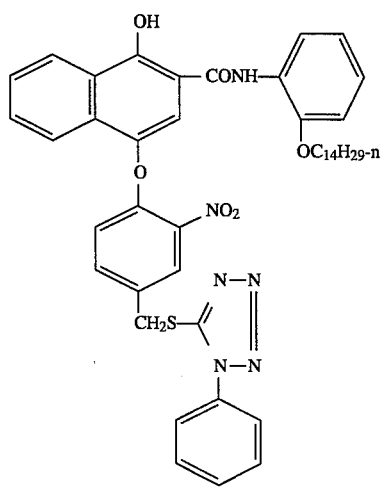

D7

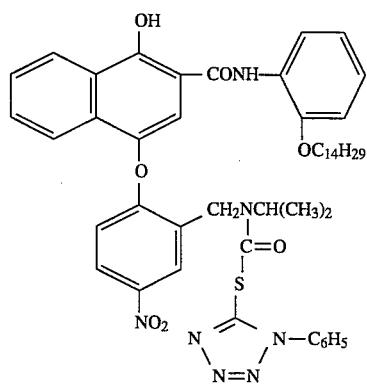

D8

It is also contemplated that the concepts of the present invention may be employed to obtain reflection color prints as described in *Research Disclosure*, November 1979, Item 18716, available from Kenneth Mason Publications, Ltd, Dudley Annex, 12a North Street, Emsworth, Hampshire P0101 7DQ, England, incorporated herein by reference. Materials of the invention may be coated on pH adjusted support as described in U.S. Pat. No. 4,917,994; with epoxy solvents (EP 0 164 961); with nickel complex stabilizers (U.S. Pat. No. 4,346,165; U.S. Pat. No. 4,540,653 and U.S. Pat. No. 4,906,559 for example); with ballasted chelating agents such as those in U.S. Pat. No. 4,994,359 to reduce sensitivity to polyvalent cations such as calcium; and with stain reducing compounds such as described in U.S. Pat. No. 5,068,171 and U.S. Pat. No. 5,096,805. Other compounds useful in combination with the invention are disclosed in Japanese Published;.Applications 83-09,959; 83-62,586; 90-072,629, 90-072,630; 90-072,632; 90-072,633; 90- 072,634; 90-077,822; 90-078,229; 90-078,230; 90- 079,336; 90-079,338; 90-079,690; 90-079,691; 90- 080,487; 90-080,489; 90-080,490; 90-080,491; 90- 080,492; 90-080,494; 90-085,928; 90-086,669; 90- 086,670; 90-087,361; 90-087,362; 90-087,363; 90- 087,364; 90-088,096; 90-088,097; 90-093,662; 90- 093,663; 90-093,664; 90-093,665; 90-093,666; 90- 093,668; 90-094,055; 90-094,056; 90-101,937; 90-103,409; 90-151,577.

Especially useful in this invention are tabular grain silver halide emulsions. Specifically contemplated tabular grain emulsions are those in which greater than 50 percent of the total projected area of the emulsion grains are accounted for by tabular grains having a thickness of less than 0.3 micron (0.5 micron for blue sensitive emulsion) and an average tabularity (T) of greater than 25 (preferably greater than 100), where the term "tabularity" is employed in its art recognized usage as $$T = ECD/t^2$$

where

ECD is the average equivalent circular diameter of the tabular grains in microns and t is the average thickness in microns of the tabular grains.

The average useful ECD of photographic emulsions can range up to about 10 microns, although in practice emulsion ECD's seldom exceed about 4 microns. Since both photographic speed and granularity increase with increasing ECD's, it is generally preferred to employ the smallest tabular grain ECD's compatible with achieving aim speed requirements.

Emulsion tabularity increases markedly with reductions in tabular grain thickness. It is generally preferred that aim tabular grain projected areas be satisfied by thin (t< 0.2 micron) tabular grains. To achieve the lowest levels of granularity it is preferred to that aim tabular grain projected areas be satisfied with ultrathin (t< 0.06 micron) tabular grains. Tabular grain thicknesses typically range down to about 0.02 micron. However, still lower tabular grain thicknesses are contemplated. For example, Daubendiek et al U.S. Pat. No. 4,672,027 reports a 3 mole percent iodide tabular grain silver bromoiodide emulsion having a grain thickness of 0.017 micron.

As noted above tabular grains of less than the specified thickness account for at least 50 percent of the total grain projected area of the emulsion. To maximize the advantages of high tabularity it is generally preferred that tabular grains satisfying the stated thickness criterion account for the highest conveniently attainable percentage of the total grain projected area of the emulsion. For example, in preferred emulsions tabular grains satisfying the stated thickness criteria above account for at least 70 percent of the total grain projected area. In the highest performance tabular grain emulsions tabular grains satisfying the thickness criteria above account for at least 90 percent of total grain projected area.

Suitable tabular grain emulsions can be selected from among a variety of conventional teachings, such as those of the following: Research Disclosure, Item 22534, January 1983, published by Kenneth Mason Publications, Ltd., Emsworth, Hampshire P010 7DD, England; U.S. Pat. Nos. 4,439,520; 4,414,310; 4,433,048; 4,643,966; 4,647,528; 4,665,012; 4,672,027; 4,678,745; 4,693,964; 4,713,320; 4,722,886; 4,755,456; 4,775,617; 4,797,354; 4,801,522; 4,806,461; 4,835,095; 4,853,322; 4,914,014; 4,962,015; 4,985,350; 5,061,069 and 5,061,616.

The photographic elements can be single colour elements or multicolour elements. In a multicolour element, the dye-forming couplers of this invention which provide magenta dyes would usually be associated with a green-sensitive emulsion, although they could be associated with an emulsion sensitised to a different region of the spectrum, or with a panchromatically sensitised, orthochromatically sensitised or unsensitised emulsion. Multicolour elements contain dye image-forming units sensitive to each of the three primary regions of the spectrum. Each unit can be comprised of a single emulsion layer or of multiple emulsion layers sensitive to a given region of the spectrum. The layers of the element, including the layers of the image-forming units, can be arranged in various orders as known in the art.

A typical multicolour photographic element comprises a support bearing yellow, magenta and cyan dye image-forming units comprising at least one blue-, green- or red-sensitive silver halide emulsion layer having associated therewith at least one yellow, magenta or cyan dye-forming coupler respectively, at least one of the dye-forming couplers being a coupler of this invention. The element can contain additional layers, such as filter and barrier layers.

The following Examples are included for a better understanding of the invention.

Preparative Example 1

Compound C-1 of Table 1 is prepared by a four-step synthesis and synthetic details for it and all intermediates are provided below. The preparation is illustrated by the following sequence.

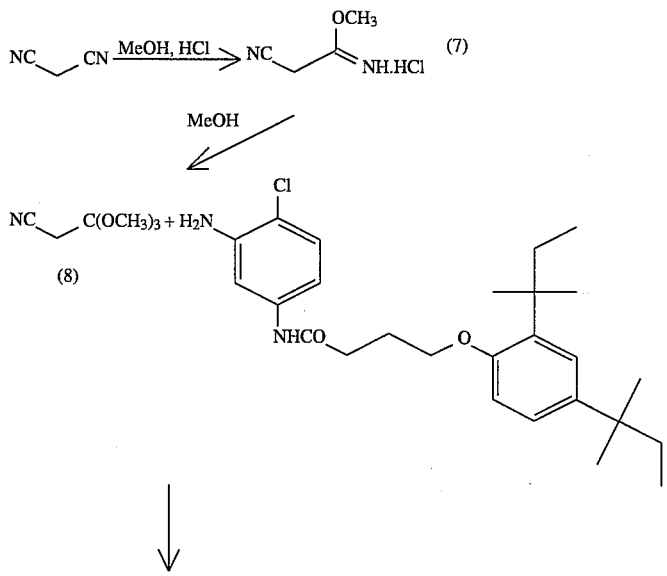

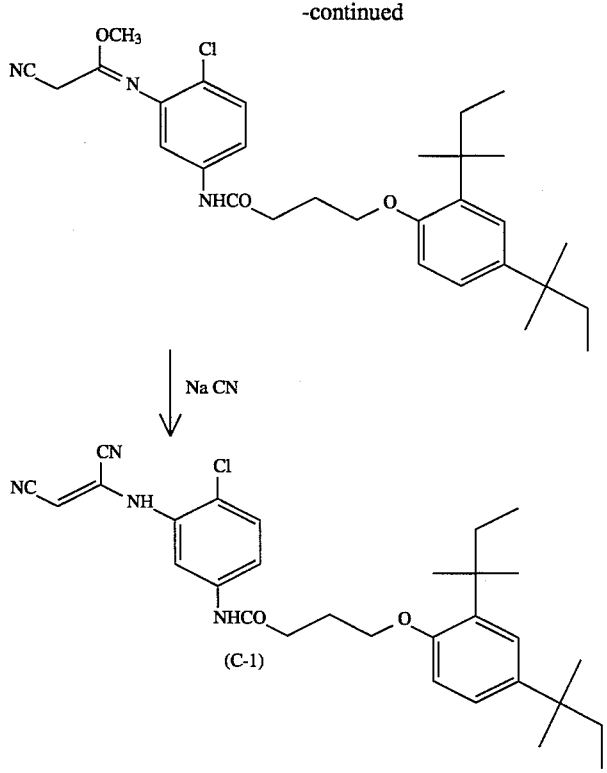

Methyl Cyanoacetimidate Hydrochloride (7)

A solution of malononitrile (66 g; 1 mole) in diethyl ether (500 ml) and methanol (44 g; 1.38 mole) was cooled to 0° C. by means of an ice-salt bath. The solution was well stirred and hydrogen chloride bubbled through it for 1 h. On standing at 0° C. overnight the product crystallised as a white solid. This was filtered, washed with diethyl ether and allowed to dry to afford the imidate hydrochloride as white crystals (100.6 g; 75% yield). The product was used without characterisation in the preparation of trimethyl ortho-cyanoacetate.

Trimethyl ortho-cyanoacetate (8)

The methyl imidate ester hydrochloride salt was added to methanol (1.01) and stirred at room temperature for 18 h. Precipitated ammonium chloride was removed by filtration and the filtrate evaporated to dryness. The residue was partitioned between ether (900 ml) and a saturated sodium carbonate solution (300 ml). The organic layer was separated, dried over magnesium sulphate and filtered. Removal of the ether in vacuo gave the orthoester as a pale yellow oil (75 g; 69%). The product was shown to be pure by NMR spectroscopy [2.86 (2H, s, NC—CH2) and 3.36 (9H, s, OMe)] and used without further characterisation.

Compound (9)

Trimethyl ortho-cyanoacetate (14.5 g; 100 mmole) and the aniline (33.3 g; 75 mmole) were mixed together in a round-bottom flask and heated by means of an oil bath at a temperature of 130°–140° C. When all of the aniline had melted so that the reaction comprised a mobile liquid, a catalytic amount of p-toluene sulphonic acid was added. This caused the reaction mixture to bubble and methanol to distill from the open flask. Heating was continued for a further 40 minutes then suction was applied to the reaction vessel by means of a water pump for 5 minutes more. The reaction mixture was opened to the air and allowed to cool to room temperature to leave a brown gum which was then dissolved in hot methanol (100 ml). On stirring the solution at ice-bath temperature, a cream coloured solid crystallised. This was filtered and dried under suction to give the pure imidate product as an amorphous solid (30.34 g; 77%).

| $C_{30}H_{40}ClN_3O_3$ | % | | | |
|---|---|---|---|---|
| | C | H | Cl | N |
| requires: | 68.5 | 7.6 | 6.8 | 8.0 |
| found: | 68.4 | 7.7 | 6.75 | 8.0 |

Compound C-1

To a solution of 5.3 g (10 mmole) compound 9 obtained above in water (5 ml) and DMF (75 ml) was added sodium cyanide (1 g; 20 mmole). The mixture was allowed to stir at room temperature for 4 hours then it was warmed gently by means of a steam bath for 2 hours. The solution was then allowed to cool before being poured onto 1.51 of brine into which had been dissolved 15 ml of concentrated hydrochloric acid. The brown precipitate was extracted into ethyl acetate and washed with brine. The organic layer was separated, dried with anhydrous magnesium sulphate, and filtered. The solvents were removed under reduced pressure to leave a brown gum. Column chromatography using ethyl acetate: 60–80 petrol in the ratio of 1:3 gave impure product as a pale yellow solid (4.8 g). Pure product was obtained as a cream coloured solid (4 g; 77%) by trituration with a mixture of ethyl acetate and 60–80 petrol. The product exhibited satisfactory mass and proton NMR spectra.

| $C_{30}H_{37}ClN_4O_2$ | % | | | |
|---|---|---|---|---|
| | C | H | Cl | N |
| requires: | 69.1 | 7.2 | 6.8 | 10.75 |
| found: | 69.1 | 7.5 | 6.8 | 10.6 |

Preparative Example 2

Compound C-50 of Table 1 is prepared from compound C-1 by a two step synthesis and synthetic details for it are provided below.

Compound C-50

Sulphuryl chloride (1.61 g; 12 mmol) was added dropwise to a solution of 1-phenyl-1H-tetrazole-5-thiol (1.96 g; 11 mmol) in dry dichloromethane (100 ml) and the resulting mixture stirred at room temperature for 3 hours. After this time the solvents were removed under reduced pressure to leave a brown oil. This was dissolved in dry dimethylformamide (10 ml) then added rapidly to a solution of compound C-1 (5.21 g; 10 mmol) in dimethylformamide (50 ml). The resulting solution was stirred at room temperature for 18 hours before being poured onto dilute hydrochloric acid (40 ml of c.HCl in 31 of water) to precipitate a pale yellow solid. The solid was extracted into ethyl acetate and washed with brine; the organic layer was separated, dried with anhydrous magnesium sulphate, filtered then the solvents were removed under reduced pressure to leave the crude product as a yellow solid (6.96 g). Pure product (5.2 g, 75%) was obtained from this as a pale yellow solid by column chromatography using silica-gel (63–200 mesh) as the solid support and ethyl acetate and 60–80 petroleum, in the ratio of 1:2, as eluent. The product exhibited satisfactory mass and proton NMR spectroscopy.

| $C_{37}H_{41}ClN_8O_2S$ | % | | | | |
|---|---|---|---|---|---|
| | C | H | Cl | N | S |
| requires: | 63.7 | 5.9 | 5.0 | 16.1 | 4.6 |
| found: | 63.1 | 6.0 | 4.7 | 16.1 | 4.4 |

Compound C-52

Compound C-52 of Table 1 was prepared from C-51 in a one-step synthesis and the synthetic details are provided below.

A solution of sulphuryl chloride (2.43 g; 18 mmol) in dichloromethane (50 ml) was added to a solution of compound C-51 (7.83 g; 18 mmol) in dichloromethane (100 ml) over 30 minutes. The resulting pale yellow solution was stirred at room temperature for 1 hour before the solvents were removed under reduced pressure to leave the crude product as a yellow oil. Trituration of this with ethyl acetate and 60–80 petroleum in the ratio of 1:100 afforded pure product as a cream coloured solid (4.59 g; 54%). The product exhibited satisfactory mass and proton NMR spectra.

| $C_{22}H_{29}C_{12}N_3O_2S$ | % | | | | |
|---|---|---|---|---|---|
| | C | H | Cl | N | S |
| requires: | 56.2 | 6.2 | 15.1 | 8.9 | 6.8 |
| found: | 56.2 | 6.3 | 15.0 | 8.9 | 6.55 |

Example 1—Dye Image Properties

The compounds C-1 to C-6 of the present invention and control compounds 1–3 were incorporated into a photographic silver bromoiodide emulsion and coated in the following format:-

| Gel Supercoat | gelatin | 1.50 g/m² |
|---|---|---|
| Emulsion Layer | Silver bromoiodide | 1.60 g/m² |
| Coupler | | 1.04 mmol/m² |
| Gelatin | | 2.42 g/m² |
| Bis (vinylsulphonyl)-methane (hardener) | | 0.06 g/m² |
| Support | Cellulose acetate | |

Control compounds 1–3 had the following formulae:

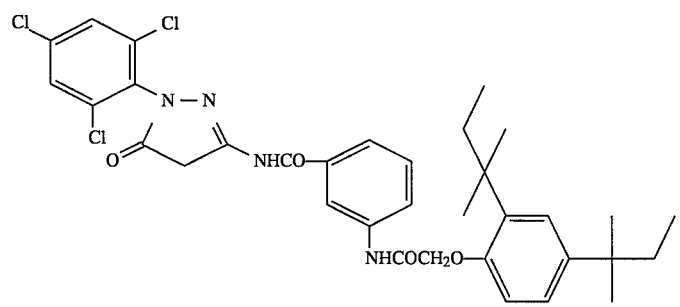

CONTROL 1

-continued

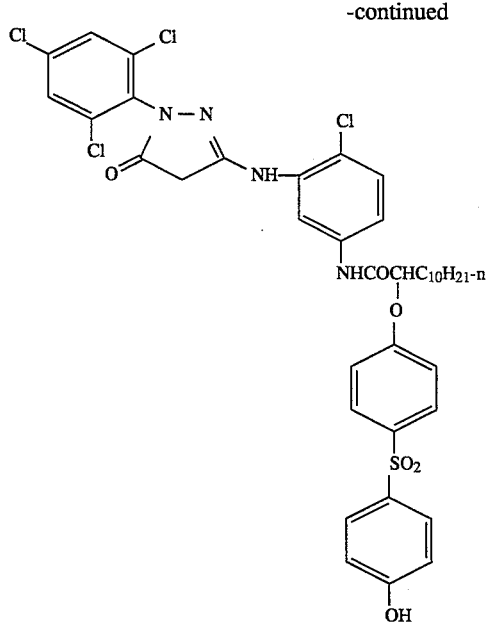

CONTROL 2

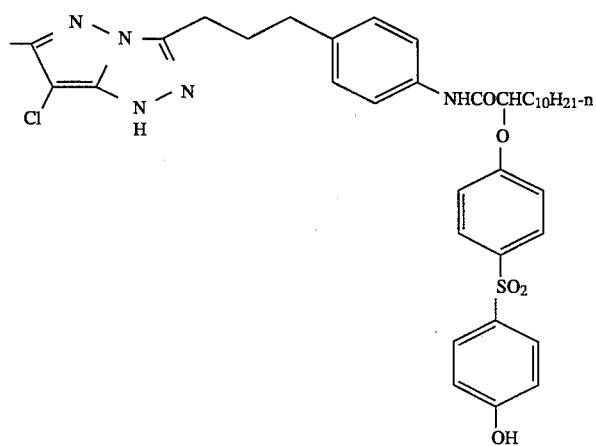

CONTROL 3

The coupler dispersion used contained 6% w/w gelatin, 8.8% coupler and coupler solvents in the ratio:- coupler: tricresyl phosphate: 2-(2-butoxyethoxy)ethyl acetate 1:0.5:1.5.

The experimental photographic coatings prepared in this way are slit and chopped into 35 mm test strips. These are exposed through a 0–4.0 neutral density step wedge (0.2 ND step increments) and Daylight V, Wratten 9 filters then processed through the following the C-41 process described in British Journal of Photography (1988) 196–198:

| Developer | 2.5 minutes |
| Bleach | 4.0 minutes |
| Wash | 2.0 minutes |
| Fix | 4.0 minutes |
| Wash | 2.0 minutes |

For each test strip, step-wedge densities are measured using a Macbeth TD/504/Hewlett Packard 85 automatic transmission densitometer. Measurements of minimum density (Dmin), maximum density (Dmax) and contrast (gamma) are calculated from the D log E curves.

The results are shown in Table 4 below.

TABLE 4

| Compound | $D_{min}$ | $D_{max}$ | $\lambda_{max}$ nm | HBW nm |
|---|---|---|---|---|
| Control 1 | 0.18 | 2.52 | 555.5 | 96.0 |
| Control 2 | 0.30 | 2.75 | 547.5 | 94.5 |
| Control 3 | 0.15 | 2.68 | 553.3 | 90.5 |
| C-1 | 0.19 | 2.22 | 549.0 | 92.0 |
| C-2 | 0.31 | 3.36 | 550.0 | 95.0 |
| C-3 | 0.40 | 2.93 | 555.0 | 100.0 |
| C-4 | 0.22 | 2.48 | 552.5 | 92.0 |
| C-5 | 0.27 | 1.85 | 549.0 | 101.0 |
| C-6 | 0.22 | 1.14 | 552.0 | 106.0 |
| C-45 | 0.16 | 2.64 | 546.0 | 87.0 |

The results presented in Table 4 for the $\lambda_{max}$ and half-band width values show that compounds C-1 to C-6 produce dyes of similarly desirable absorption characteristics as each of the control couplers. However the dyes from compounds C-1 to C-6 show much less secondary absorption in the blue region of the spectrum than the dyes from control pyrazolone couplers 1 or 2. This is similar to control compound 3 (a pyrazolotriazole). It is well recognised that a secondary absorption in the blue region is undesirable as it has an adverse effect on colour reproduction. Accordingly the use of compounds C-1 to C-6 in a photographic system offers advantages over the use of the control couplers 1 or 2.

The dye formed from coupler C-9 has an extinction coefficient of 50,000 in ethyl acetate and 52,000 in tricresyl phosphate. This is similar or higher than dyes formed from known magenta couplers.

FIG. 1 is a plot of absorbance vs wavelength for the dyes obtained from coupler C-3 and Control 1 (dotted line). It can be seen that the unwanted absorption of Control 1 in the 400–450 nm region is not present in the dye formed from coupler C-3.

The dyes from C-1 to C-6 show good light fastness and keeping properties when compared with the control couplers 1-3.

As judged by the values presented for $D_{max}$, the couplers C-1 to C-6 show a range of photographic activity which may be less than, equal to or greater than the activity shown by the control couplers. The availability of such a range of coupler activity implies that a coupler may be selected to best comply with the requirements of any particular photographic system.

The preparation of control 3 involves difficult methods of synthesis in a multi-step sequence within which product yields are often low. By contrast, the compounds C-1 to C-6 are easily obtained in high yield from readily available starting materials in a four-step sequence.

Example 2—Fastness Properties

The dye sample patches (density= 1.0) are tested for light stability using the EDIE fadeometer for fade times of 100 h and 200 h accumulated fade. The spectrophotometric curves are remeasured after each fade period and the degree of fade quoted as the fractional decrease in density prior to fading.

Dark/wet stability is tested by incubating the yellow dye samples in a dark oven for periods of 1, 3 and 6 weeks at a constant 60° C. and 70% relative humidity. The spectrophotometric curves of the samples are then remeasured and once again the degree of fade is quoted as the fractional decrease in density at the absorption maximum (AD) relative to the initial density prior to fading. A positive value for dye fade indicates an increase in dye density.

Spectrophotometry has been chosen to monitor dye fade so that any subtle changes in curve shape as the dye fades will be apparent.

Typical EDIE fade results are shown below:

TABLE 5

| Compound | 100 hrs | 200 hrs |
|---|---|---|
| C-6 | −0.34 | −0.58 |
| Control 3 | −0.43 | −0.65 |

Typical dark/wet fade results are shown below:

TABLE 6

| Compound | 1 week | 2 weeks | 3 weeks |
|---|---|---|---|
| C-6 | −0.05 | −0.14 | −0.23 |
| Control 1 | −0.34 | −0.36 | −0.38 |

In both tables the dyes formed from couplers of the invention are shown to have light fastness as good as or better than Control 3 and dark/wet fade considerably better than Control 1.

Example 3—Variable $\lambda_{max}$ in coupler solvents

The dye obtained from coupler C-9 was dissolved in a number of solvent mixtures. The λmax and bandwidth of each solution was measured and the results recorded in the table below.

TABLE 7

| Solvent System | Ratio | $\lambda_{max}$ nm | Bandwidth nm |
|---|---|---|---|
| Cyclohexane:ethyl acetate | 9:1 | 520 | 73 |
| Diethyl ether:ethyl acetate | 9:1 | 525 | 72 |
| Methanol:ethyl acetate | 9:1 | 535 | 77 |
| Acetone:ethyl acetate | 9:1 | 537 | 77 |
| Dimethyl Sulphoxide | | 553 | 83 |
| Diethy lauramide:tricresyl phosphate | 9:1 | 544 | 73 |
| p-Dodecylphenol:tricresyl phosphate | 9:1 | 547 | 78 |

As can be seen, the $\lambda_{max}$ can be varied by choice of solvent while the bandwidth stays comparatively constant.

Example 4—Retouchability

The dye image of a number of the coatings described above was treated with a reducing solution to convert the dye to its leuco form which is relatively uncoloured. This is often the first step in the hand retouching of a photographic image. All samples showed considerable bleaching.

The reducing solution has the following composition:

| Stannous chloride | 10 g |
|---|---|
| Ethylenediamine tetraacetic acid.2Na | 1 g |
| Acetic acid | 20 ml |
| Water to | 200 ml |

Example 5—Formaldehyde Sensitivity

In-film resistance of the coupler to formaldehyde is measured by hanging unexposed test strips in a closed container in an atmosphere of formaldehyde generated from 10 g of paraformaldehyde. A controlled relative humidity is achieved using a water/glycerol mixture. Control strips are prepared by hanging similar strips in an identical closed container with the same humidity control but without the paraformaldehyde. After 48 hours the strips are removed from the respective containers, exposed and processed through the C-41 process as described above. The resistance of the coupler to formaldehyde is then calculated as a percentage density loss relative to the unfumed control. The results are shown in Table 8 below.

TABLE 8

| Dye from Coupler | % Density Loss |
|---|---|
| Control 1 | 90 |
| Control 2 | 97 |
| Control 3 | 0.5 |
| C-1 (4-equivalent) | 32.5 |
| C-45 (2-equivalent) | 0.5 |

The couplers of the invention both show resistance to fading compared to two of the prior art dyes while the 2-equivalent coupler C-45 and Control 3 (a pyrazolotriazole coupler) show substantial immunity to fading by formaldehyde.

The compounds of formula Control 1 and C-50 were together incorporated into a photographic silver bromoiodide emulsion and coated in the following format:-

| | | |
|---|---|---|
| Gel Supercoat | gelatin | 1.50 g/m² |
| Emulsion Layer | Silver bromoiodide | 0.8 g/m² |
| Control 1 | | 1.265 mmol/m² |
| Coupler C-50 | | (see Table 9 below) |
| Gelatin | | 2.42 g/m² |
| Bis (vinylsulphonyl)-methane (hardener) | | 0.06 g/m² |
| Support | Cellulose acetate | |

The coupler dispersion used for Control 1 contained 6% w/w gelatin, 8.8% coupler and coupler solvents in the ratio:- coupler: tricresyl phosphate: 2-(2-butoxyethoxy)ethyl acetate 1:0.5:1.5.

The coupler dispersion used for C-50 contained 12.5% w/w gelatin, 2.2% coupler and coupler solvents in the ratio:- C-50: tricresyl phosphate: 2-(2-butoxyethoxy)ethyl acetate 1:2:3.

The experimental photographic coatings prepared in this way are slit and chopped into 35 mm test strips. These are exposed through a 0–4.0 neutral density step wedge (0.2 ND step increments) and Daylight V, Wratten 9 filters then processed through the the C-41 process described in British Journal of Photography (1988) 196–198 as used above.

For each test 'strip, step-wedge densities are measured using a Macbeth TD/504/Hewlett Packard 85 automatic transmission densitometer. Measurements of maximum density (Dmax) and contrast (gamma) are calculated from the D log E curves The results from these measurements are shown in Table 9 below.

TABLE 9

| C-50 Laydown (mmol/m²) | D-max | Gamma |
|---|---|---|
| 0 | 2.22 | 1.51 |
| 0.06 | 2.07 | 1.19 |
| 0.12 | 1.89 | 1.11 |
| 0.24 | 1.63 | 0.97 |
| 0.36 | 1.47 | 0.91 |

The results show that both the $D_{max}$ and gamma of Control 1 are reduced as the level of C-50 within the emulsion layer is increased. Such a reduction in gamma and the corresponding loss in dye density clearly demonstrates that compound C-50 acts as a development inhibitor releasing coupler.

I claim:

1. A photographic element comprising a support, at least one photosensitive silver halide layer and associated therewith a color coupler of the general formula (1) or (2):

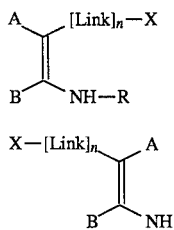

wherein A and B represent the same or different electron-withdrawing groups,

X is H or a group which splits off from the carbon atom to which it is attached on coupling with oxidized color developer, R is an alkyl, cycloalkyl, aryl or heterocyclic which may be substituted, —COR¹, —CSR¹, SOR¹, SO₂R¹, —NHCOR¹, —CONHR¹, —COOR¹, —COSR¹, —NHSO₂R¹ wherein R¹ is an alkyl, cycloalkyl, or aryl group any of which are optionally substituted, and wherein two or more of B, R, and X optionally form part of a ring and A does not form part of a ring with B, R, or X, Link is a linking group and n is 0, 1 or 2.

2. A photographic element as claimed in claim 1 in which the coupler contains a ballasting group of such size and configuration to render the coupler non-diffusible in the photographic material.

3. A photographic element as claimed in claim 1 in which the electron-withdrawing groups A and B each individually have a Hammett $\sigma_p$ value of at least 0.03.

4. A photographic element as claimed in claim 1 in which the electron-withdrawing groups A and B each individually have a Hammett $\sigma_p$ value of at least 0.35.

5. A photographic element as claimed in claim 1 in which the electron-withdrawing groups A and B each individually have a Hammett $\sigma_p$ value of 0.5 or above.

6. A photographic element as claimed in claim 1 in which groups A and B may each individually be a hydrogen, halogen, imido, —CN, —NO₂, —OR⁵, —SR⁵, —SO₂R¹, —OSO₂R¹, —SOR¹, —NHCOR⁵, — CONHR¹, —OCONHR¹, —NHCO—OR¹, —SO₂NH—R¹, —NHSO₂R¹, —NHSO₂NHR¹, —NHNH—SO₂—R⁵, —COOH, —COOR¹, —O—COR¹, —COR¹, —CSR¹, —CONHNHR¹, —CF₃, NHR⁵, —NHR⁵R⁵', or a silyloxy, aryl, aralkyl, alkyl, cycloalkyl, ureido, group having substituents such that the substituted group is electron-withdrawing, or an electron-withdrawing heterocycle, wherein R¹ is as defined in claim 1, R⁴ is an alkyl, cycloalkyl, aryl or heterocyclic group any of which are optionally substituted and R⁵ and R⁵' are each a substituted alkyl, cycloalkyl, aryl or heterocyclic group, and wherein the nature of the groups R¹, R¹', and R⁴ and the substituents thereon are such that the group is electron-withdrawing.

7. A photographic element as claimed in claim 6 in which R may be a group of the general formula:

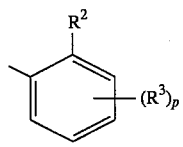

wherein p is 0 to 4 and each R³ is the same or different substituent, and

R² is a hydrogen or halogen atom or an alkyl, alkoxy, aryloxy, alkylthio, arylthio, carbonamido, carboamoyl, sulphonamido, sulphamoyl, alkylsulphonyl, arylsulphonyl, alkoxycarbonyl, acyloxy, acyl, cyano, nitro, or trifluoromethyl group.

8. A photographic element as claimed in claim 7 in which p is 0 to 3 and each R³ is in a meta or para position with respect to R² and is individually a halogen atom or an alkyl, alkoxy, aryloxy, carbonamido, carbamoyl, sulphonamido, sulfamoyl, alkylsulphoxyl, arylsulphoxyl, alkylsulphonyl, arylsulphonyl, alkoxycarbonyl, aryloxycarbonyl, acyloxy, ureido, imido, carbamate, cyano, nitro, acyl, trifluoromethyl, alkylthio, carboxyl or heterocylic group.

9. A photographic element as claimed in claim 1 in which the groups A or B are joined by way of a group that will extend the conjugated path from A or B to the —NH—R group while leaving the whole group electron-withdrawing such group having the formula:

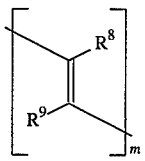

wherein $R^8$ and $R^9$ are each hydrogen, halogen, or an alkyl or aryl group that may be substituted, or $R^8$ and $R^9$ may complete a carbocyclic or heterocyclic ring, and m is 1 or 2.

10. A photographic element as claimed in claim 1 in which R may be a group of the general formula:

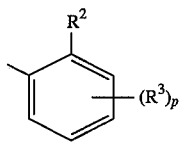

wherein p is 0 to 4 and each $R^3$ is the same or different substitutent, and $R^2$ is a hydrogen or halogen atom or an alkyl, alkoxy, aryloxy, alkylthio, arylthio, carbonamido, carboamoyl, sulphonamido, sulphamoyl, alkylsulphonyl, arylsulphonyl, alkoxycarbonyl, acyloxy, acyl, cyano, nitro, or trifluoromethyl group.

11. A photographic element as claimed in claim 10 in which p is 0 to 3 and each $R^3$ is in a meta or para position with respect to $R^2$ and is individually a halogen atom or an alkyl, alkoxy, aryloxy, carbonamido, carbamoyl, sulphonamido, sulfamoyl, alkylsulphoxyl, arylsulphoxyl, alkylsulphonyl, arylsulphonyl, alkoxycarbonyl, aryloxycarbonyl, acyloxy, ureido, imido, carbamate, cyano, nitro, acyl, trifluoromethyl, alkylthio, carboxyl or heterocylic group.

12. The element of claim 10 containing a ballast group of such size and configuration to render the coupler non-diffusible in the photographic material.

13. A photographic element as claimed in claim 10 in which the electron-withdrawing groups A and B each individually have a Hammett $\sigma_p$ value of 0.5 or above.

14. A photographic element as claimed in claim 13 in which groups A and B may each individually be a hydrogen, halogen, imido, —CN, —$NO_2$, —$OR^5$, —$SR^5$, —$SO_2R^1$, —$OSO_2R^1$, —$SOR^1$, —$NHCOR^5$, —$CONHR^1$, —$OCONHR^1$, —NHCO—$OR^1$, —$SO_2NH$—$R^1$, —$NHSO_2R^1$, —$NHSO_2NHR^1$, —NHNH—$SO_2$—$R^5$, —COOH, —$COOR^1$, —O—$COR^1$, —$COR^1$, —$CSR^1$, —$CONHNHR^1$, —$CF_3$, $NHR^5$, —$NHR^5R^{5'}$, or a silyloxy, aryl aralkyl, alkyl, cycloalkyl, ureido, group having substituents such that the substituted group is electron-withdrawing, or an electron-withdrawing heterocycle, wherein $R^1$ is as defined in claim 1, $R^{1'}$ has the same definition as $R^1$ and may be the same or different to $R^1$, $R^4$ is an alkyl, cycloalkyl, aryl or heterocyclic group any of which are optionally substituted and $R^5$ and $R^{5'}$ are each a substituted alkyl, cycloalkyl, aryl or heterocyclic group, and wherein the nature of the groups $R^1$, $R^{1'}$ and $R^4$ and the substituents thereon are such that the group is electron-withdrawing.

15. A photographic element as claimed in claim 1 in which the color coupler is any of those listed below:

TABLE 3

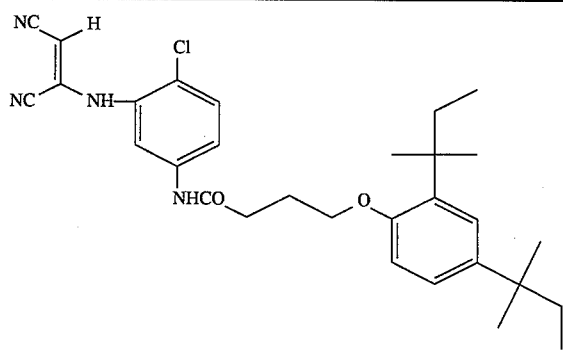
(C-1)

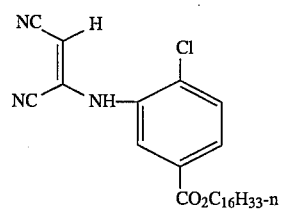
(C-2)

TABLE 3-continued
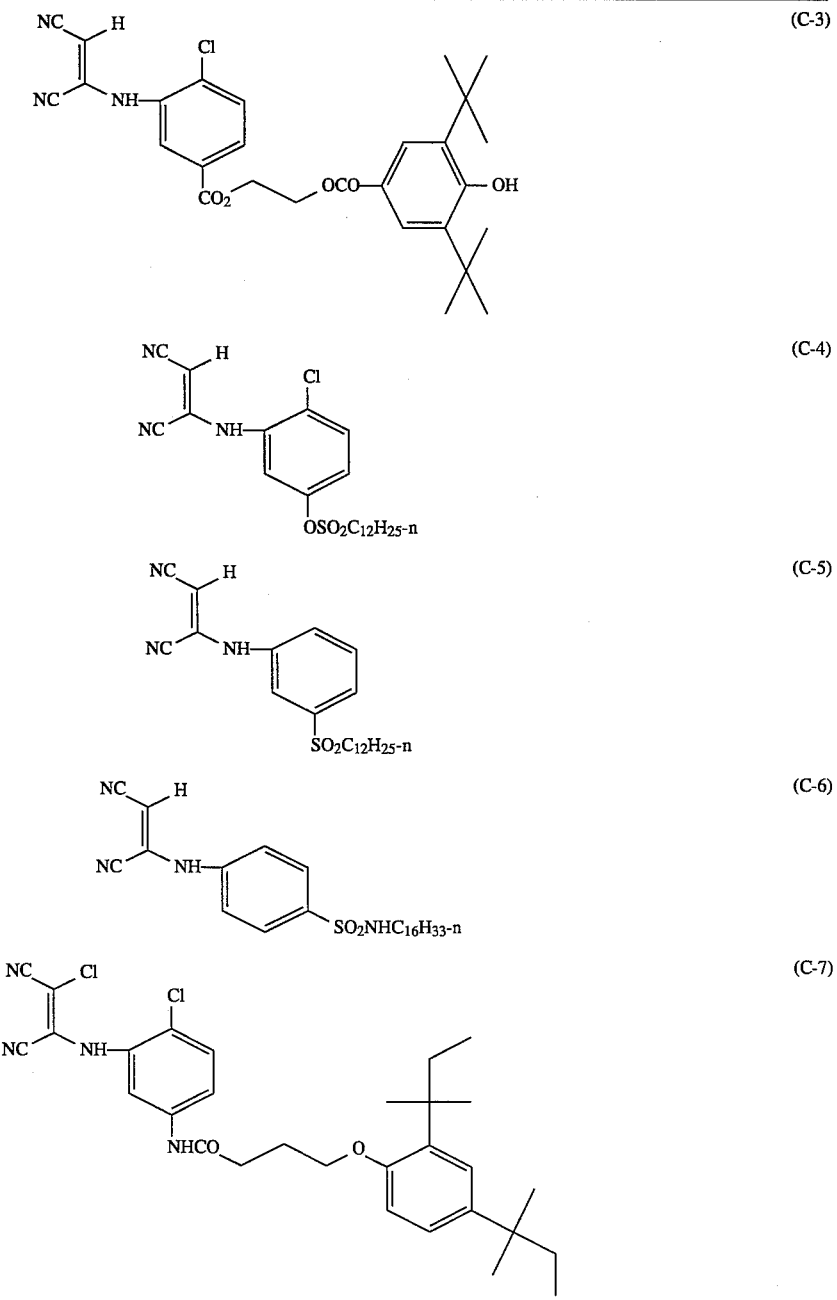

TABLE 3-continued
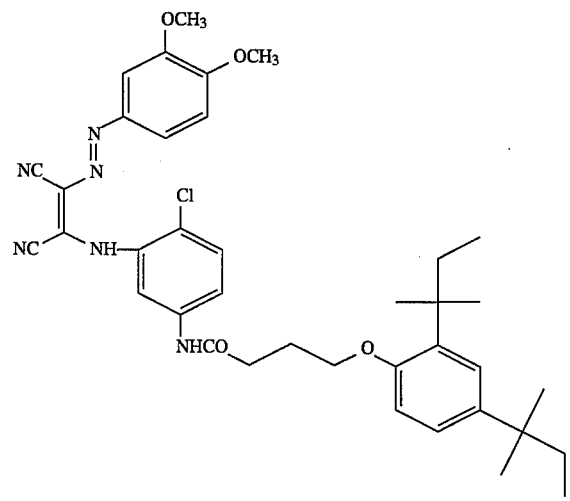
(C-8)
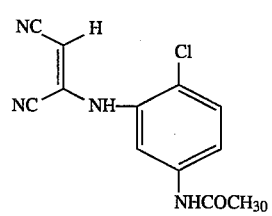
(C-9)
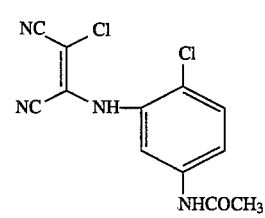
(C-10)
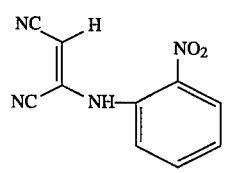
(C-11)
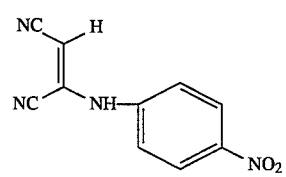
(C-12)
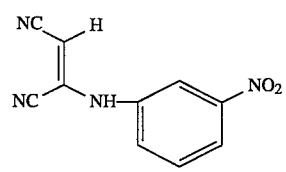
(C-13)
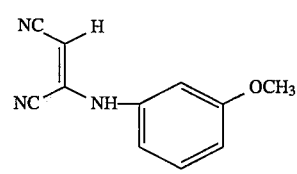
(C-14)
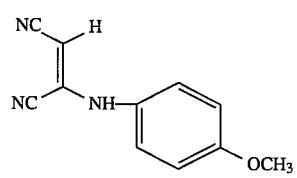
(C-15)
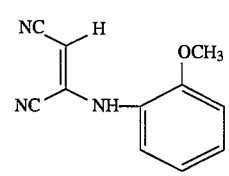
(C-16)
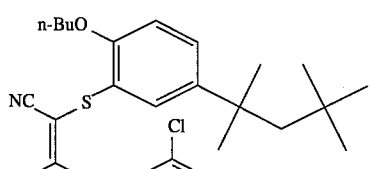
(C-17)

TABLE 3-continued
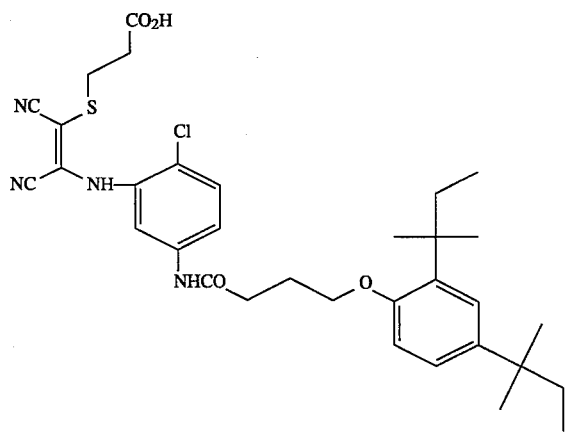
(C-18)
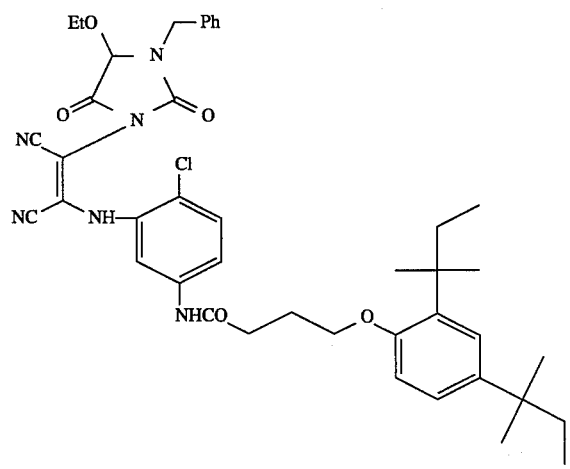
(C-19)
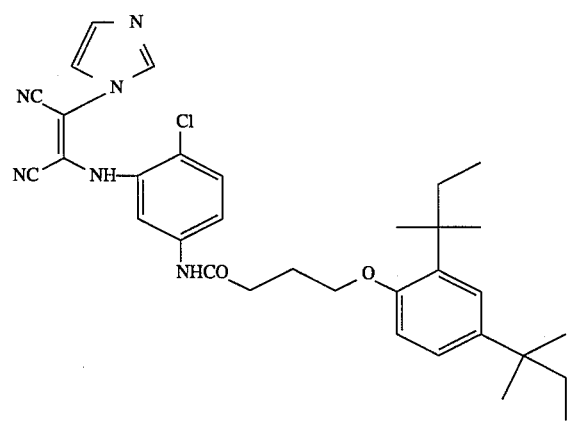
(C-20)

TABLE 3-continued
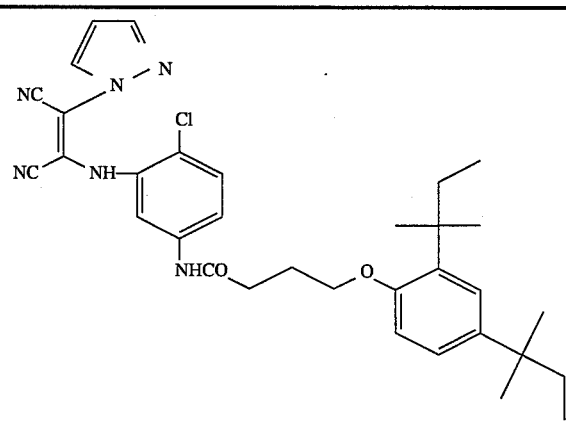
(C-21)
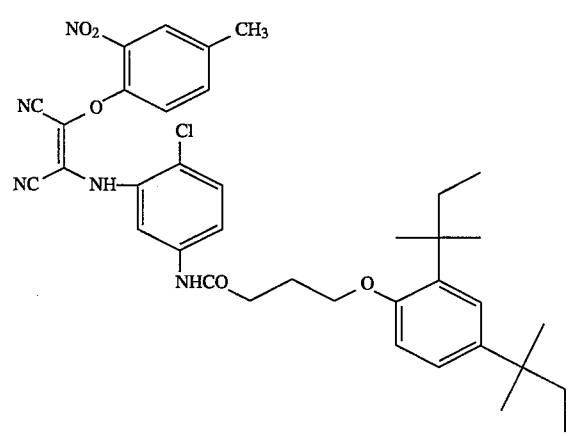
(C-22)
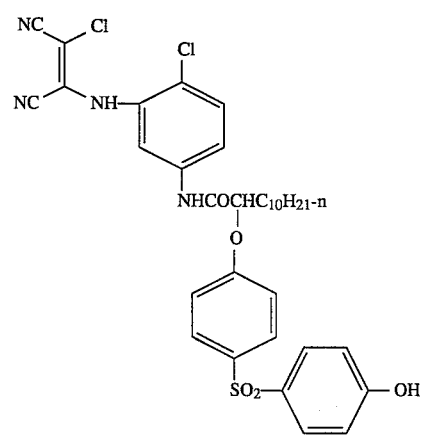
(C-23)

TABLE 3-continued
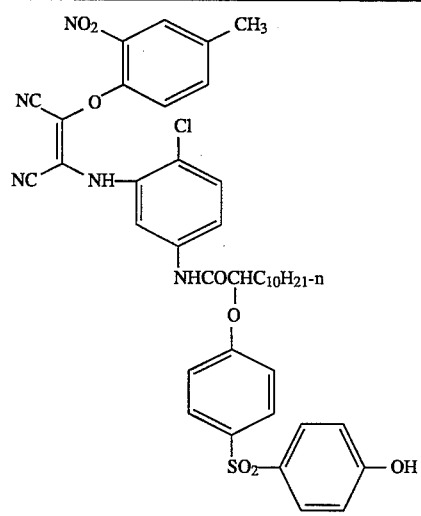
(C-24)
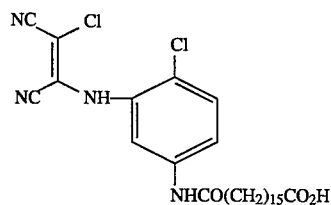
(C-25)
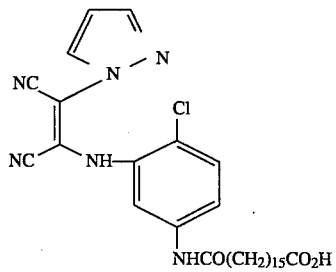
(C-26)
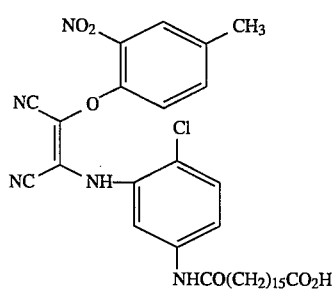
(C-27)
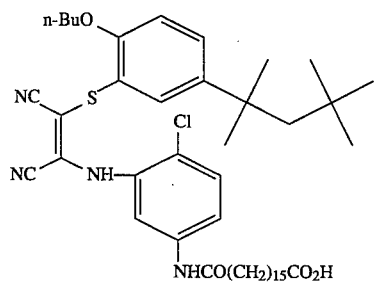
(C-28)

TABLE 3-continued
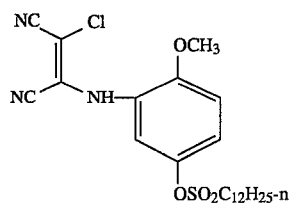
(C-29)
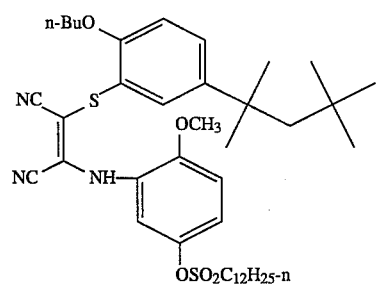
(C-30)
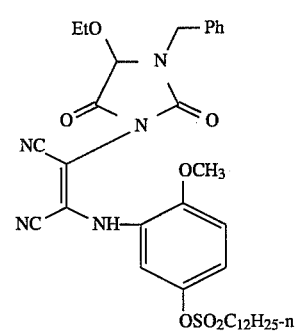
(C-31)
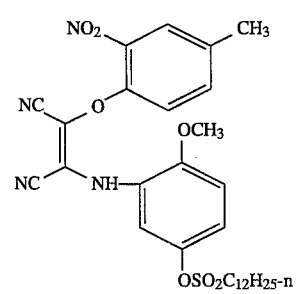
(C-32)
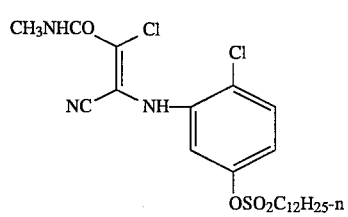
(C-33)
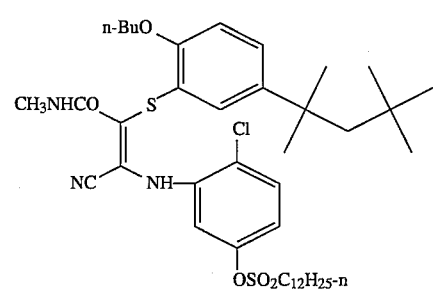
(C-34)

TABLE 3-continued
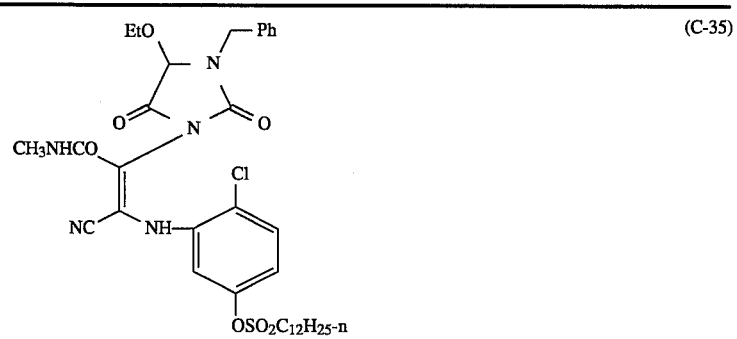
(C-35)
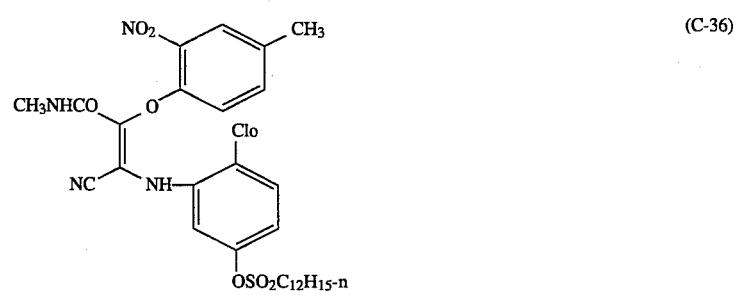
(C-36)
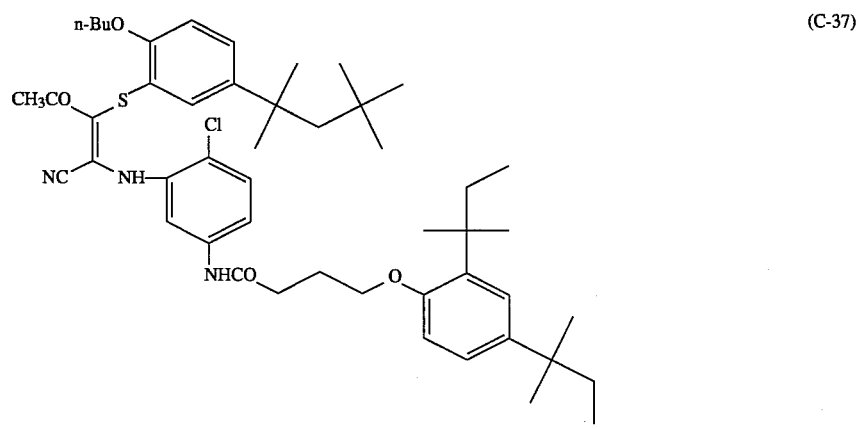
(C-37)
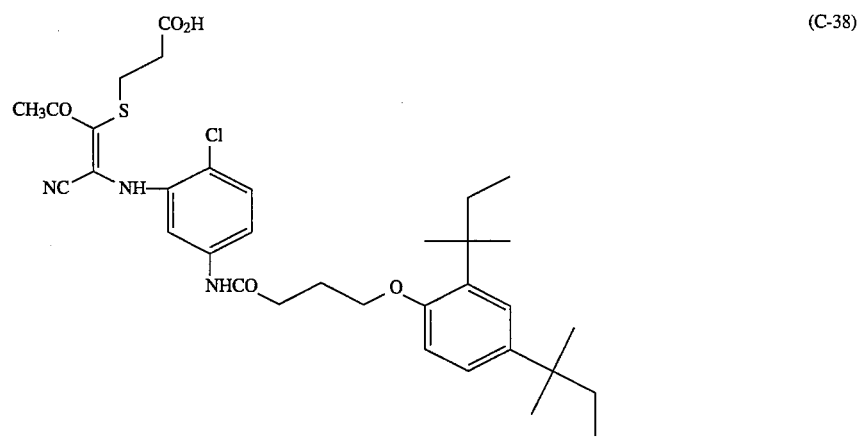
(C-38)

TABLE 3-continued
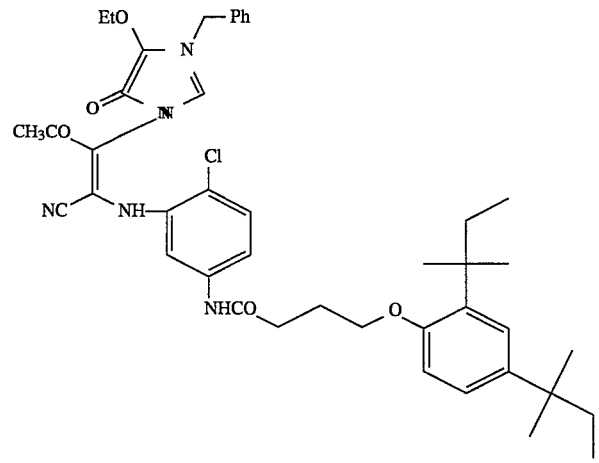
(C-39)
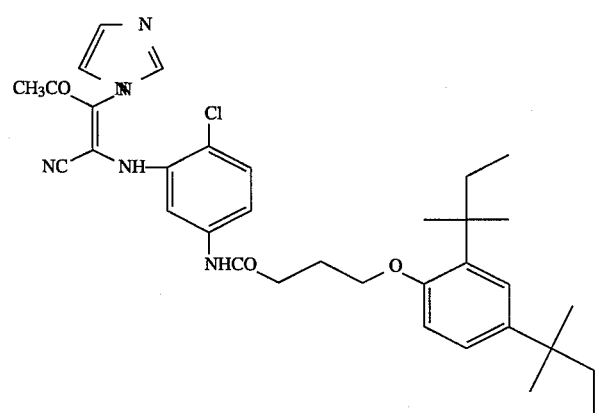
(C-40)
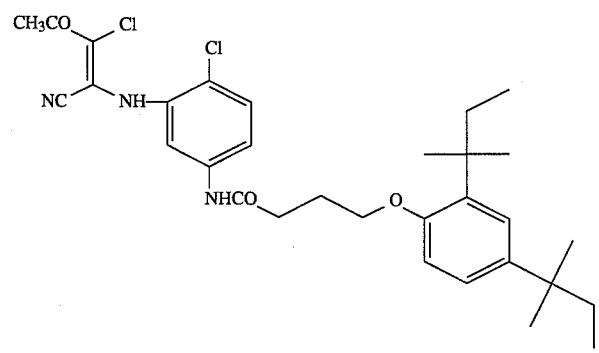
(C-41)
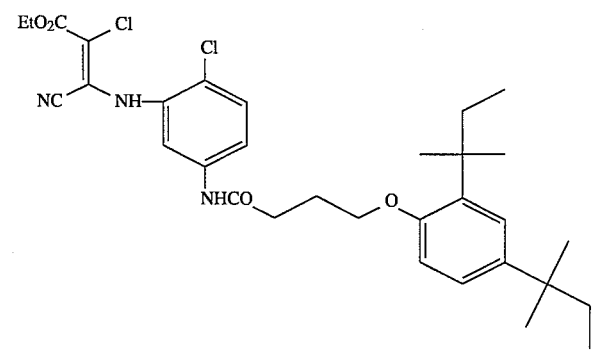
(C-42)

TABLE 3-continued
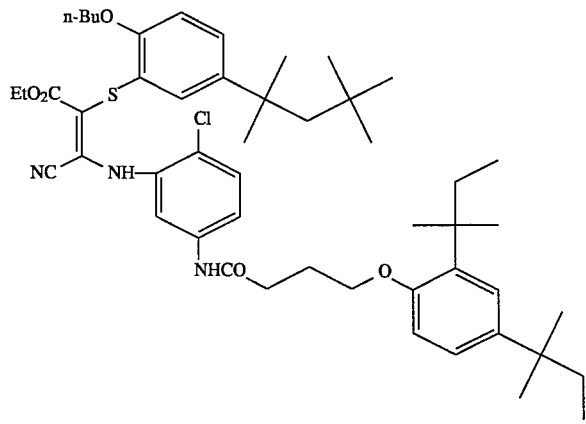
(C-43)
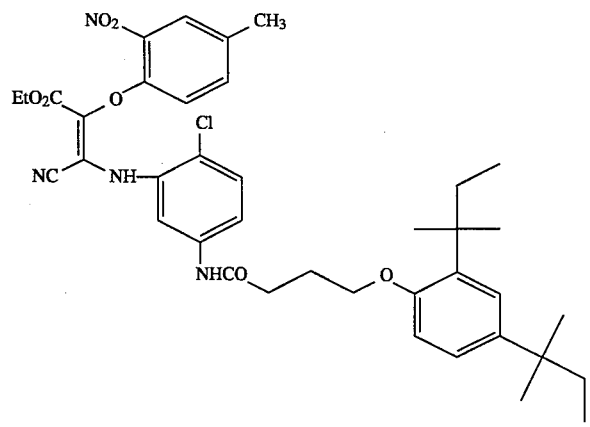
(C-44)
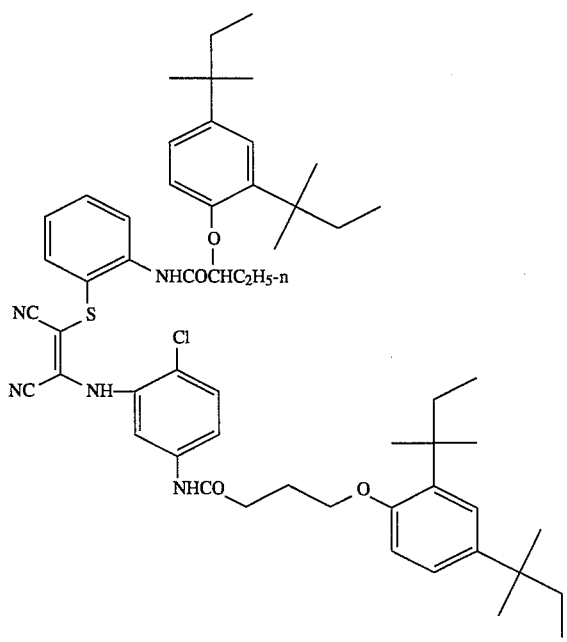
(C-45)

TABLE 3-continued
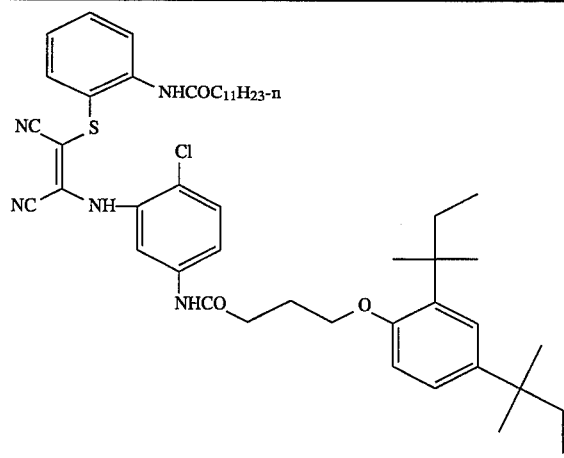
(C-46)
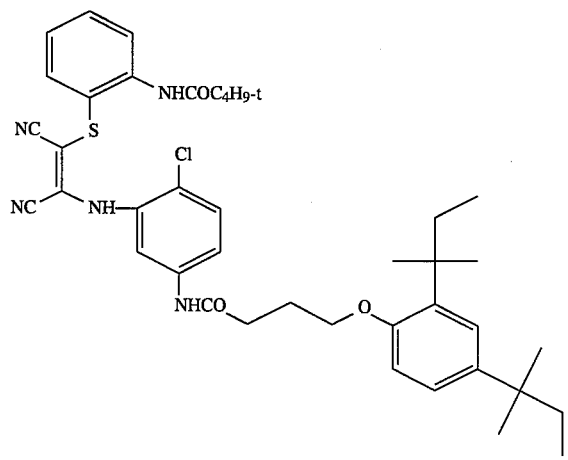
(C-47)
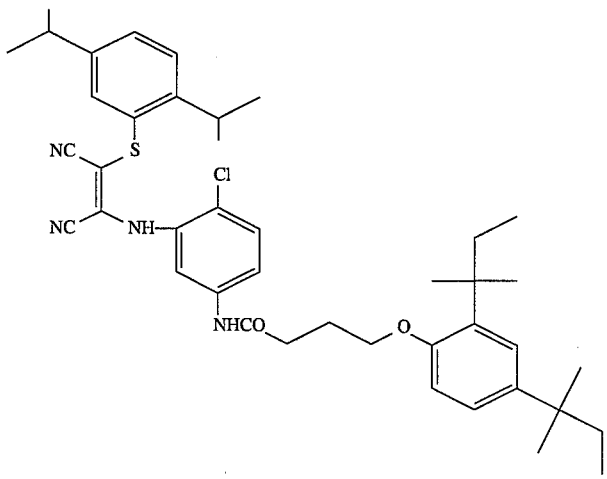
(C-48)

TABLE 3-continued
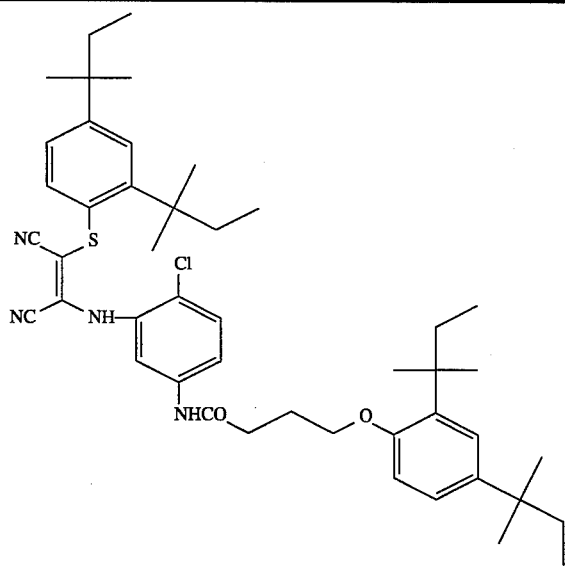
(C-49)
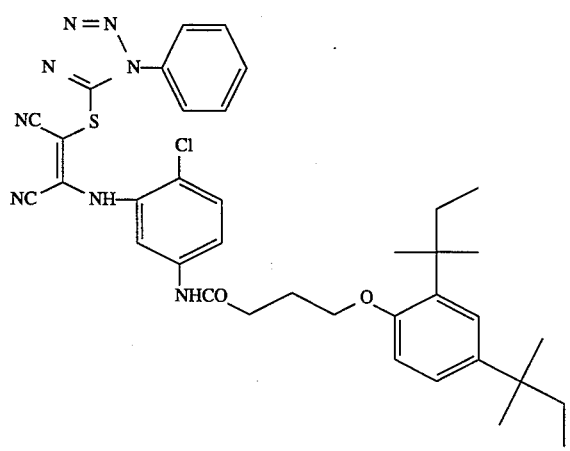
(C-50)
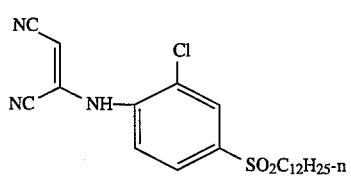
(C-51)
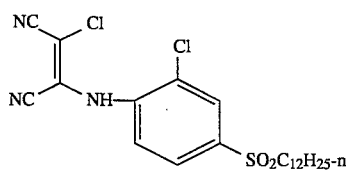
(C-52)

TABLE 3-continued
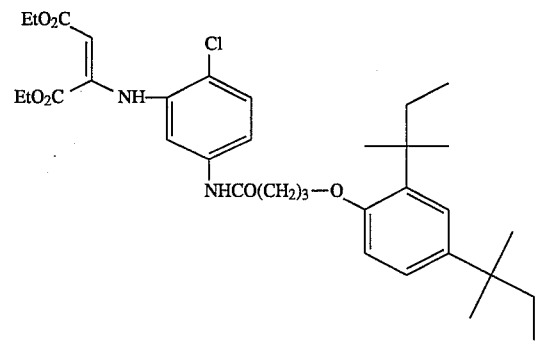
(C-53)
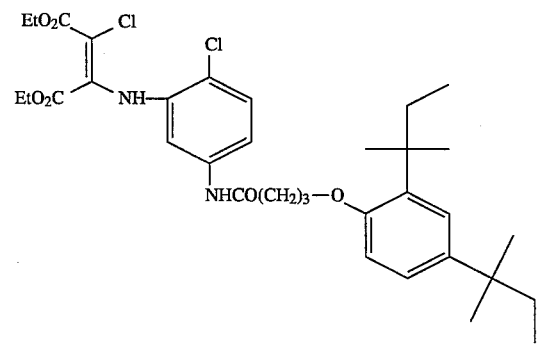
(C-54)
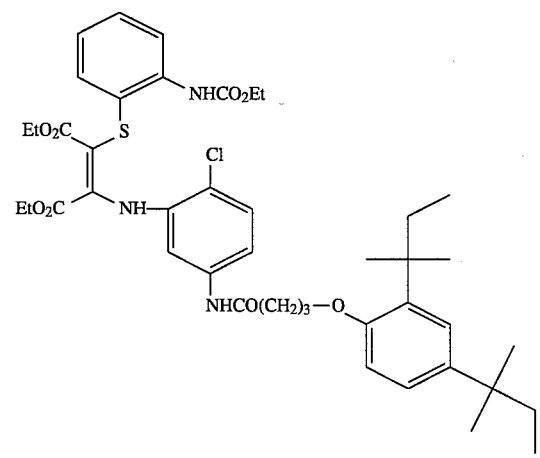
(C-55)
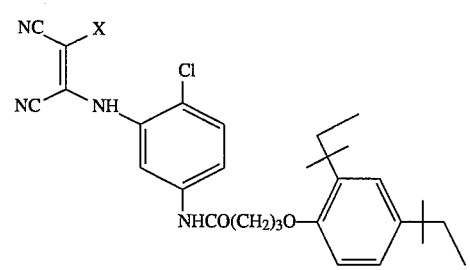
Where X is:-
C-56    C-57    C-58    C-59

TABLE 3-continued
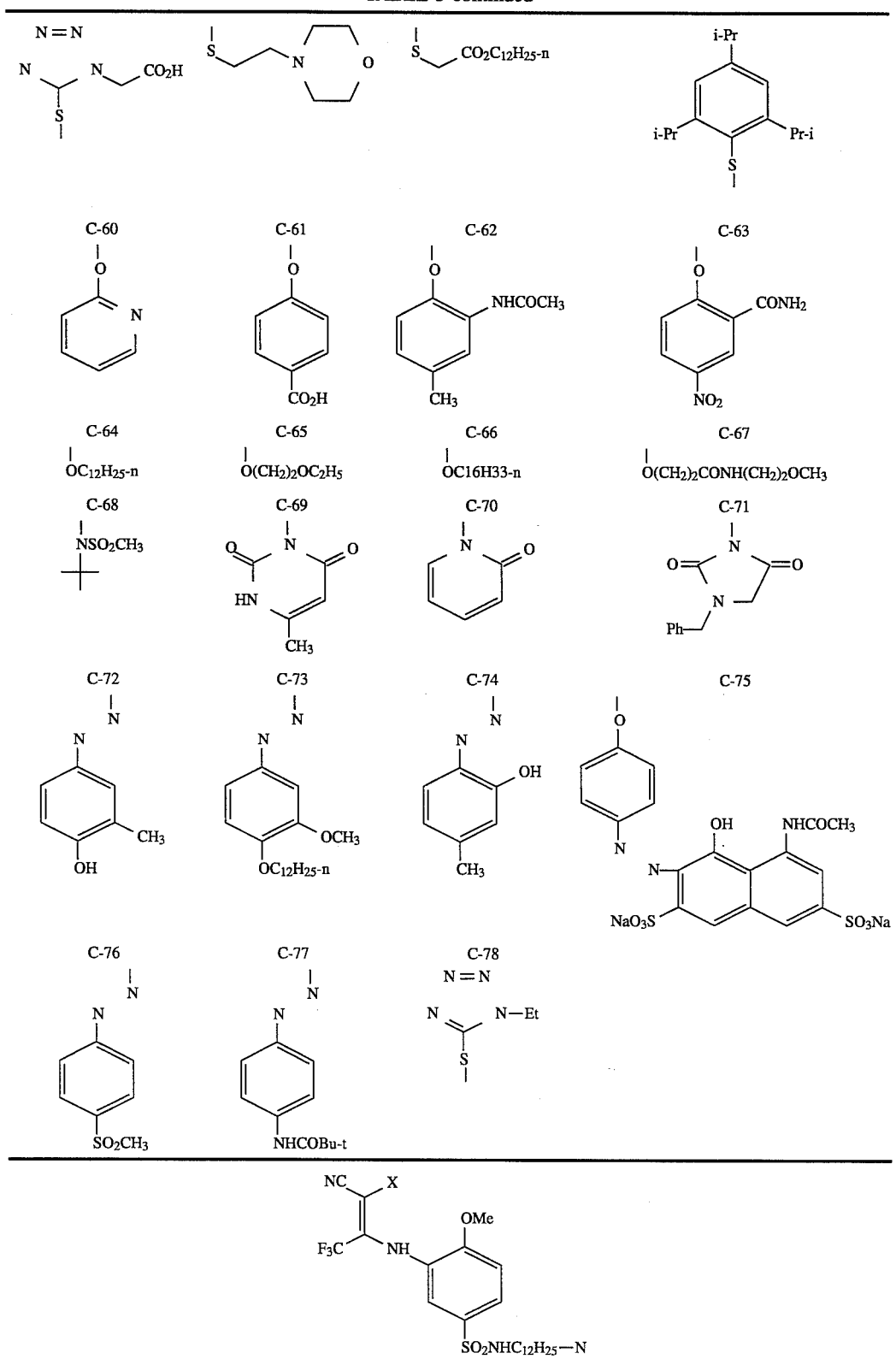
Where X is:-
| C-79 | C-80 | C-81 | C-82 |

TABLE 3-continued
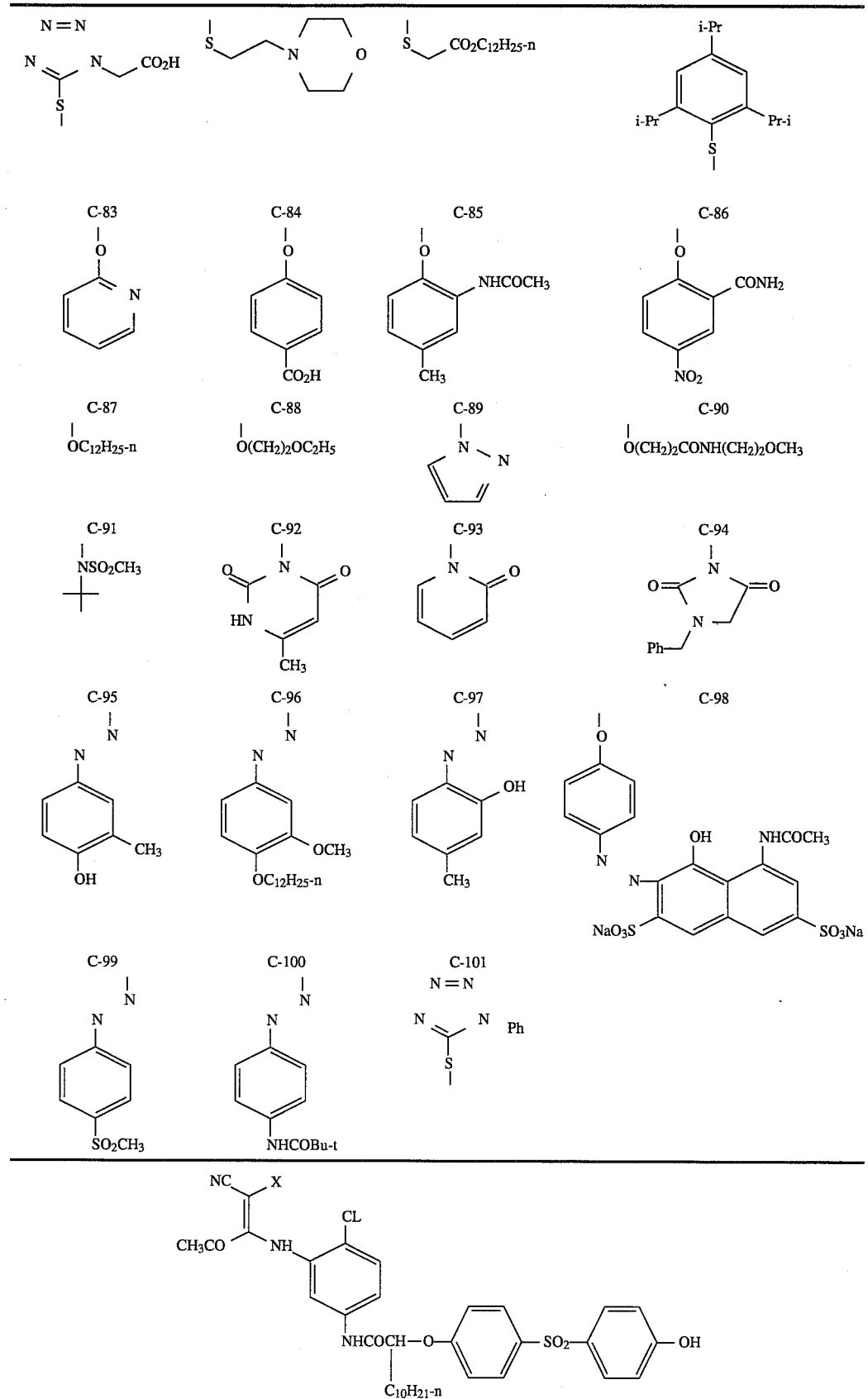

TABLE 3-continued
Where X is:-
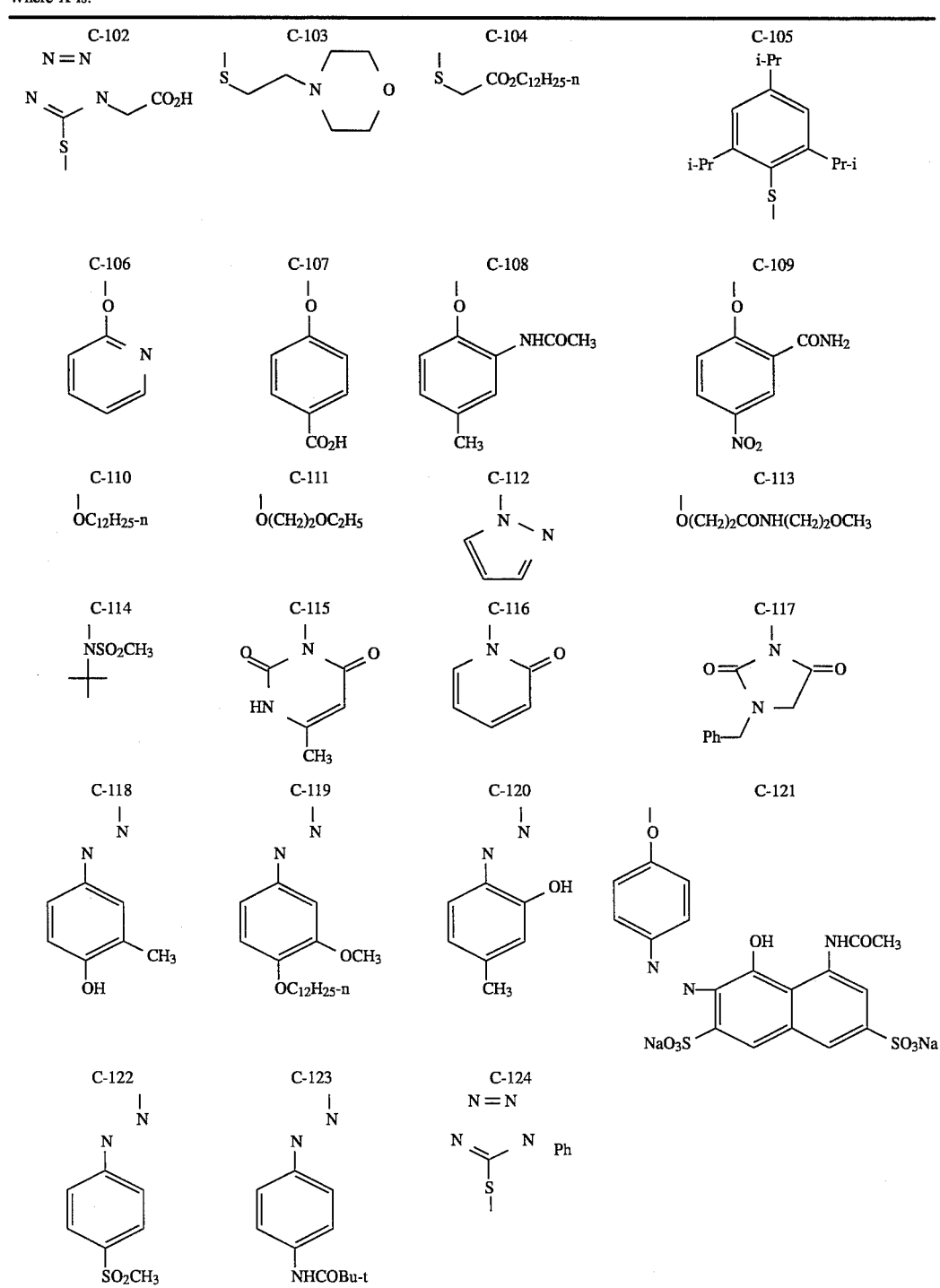

TABLE 3-continued
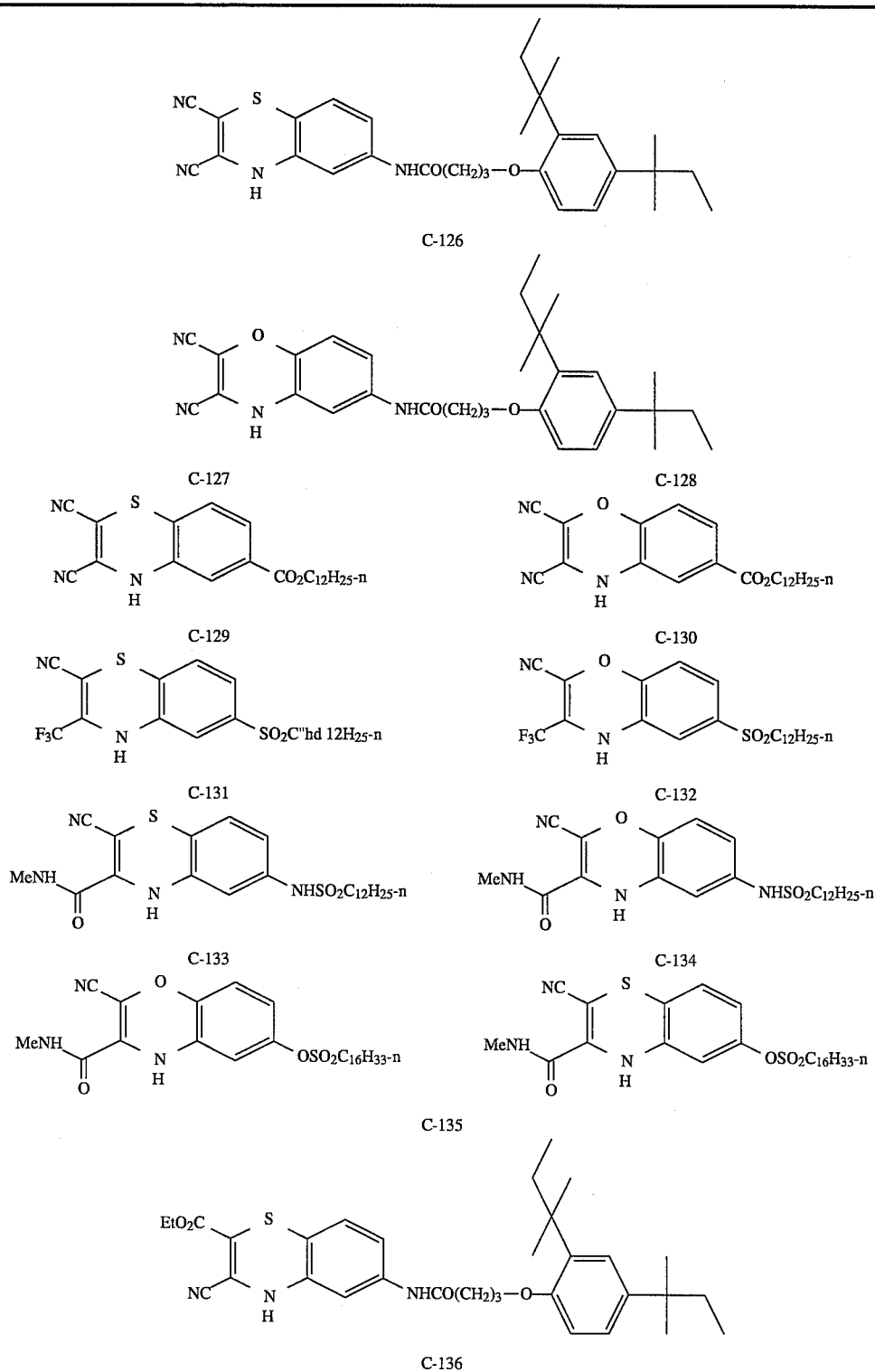

TABLE 3-continued
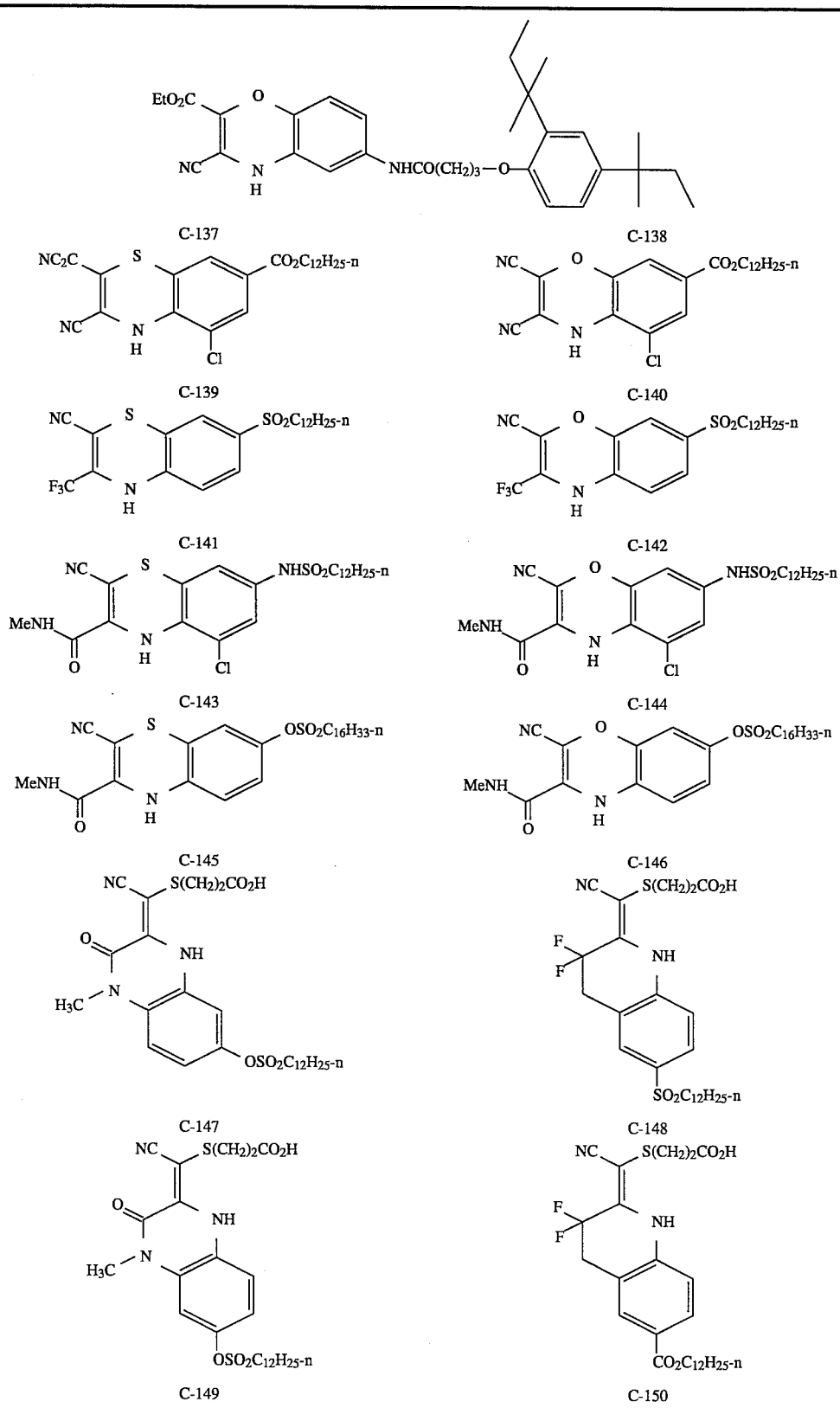

TABLE 3-continued
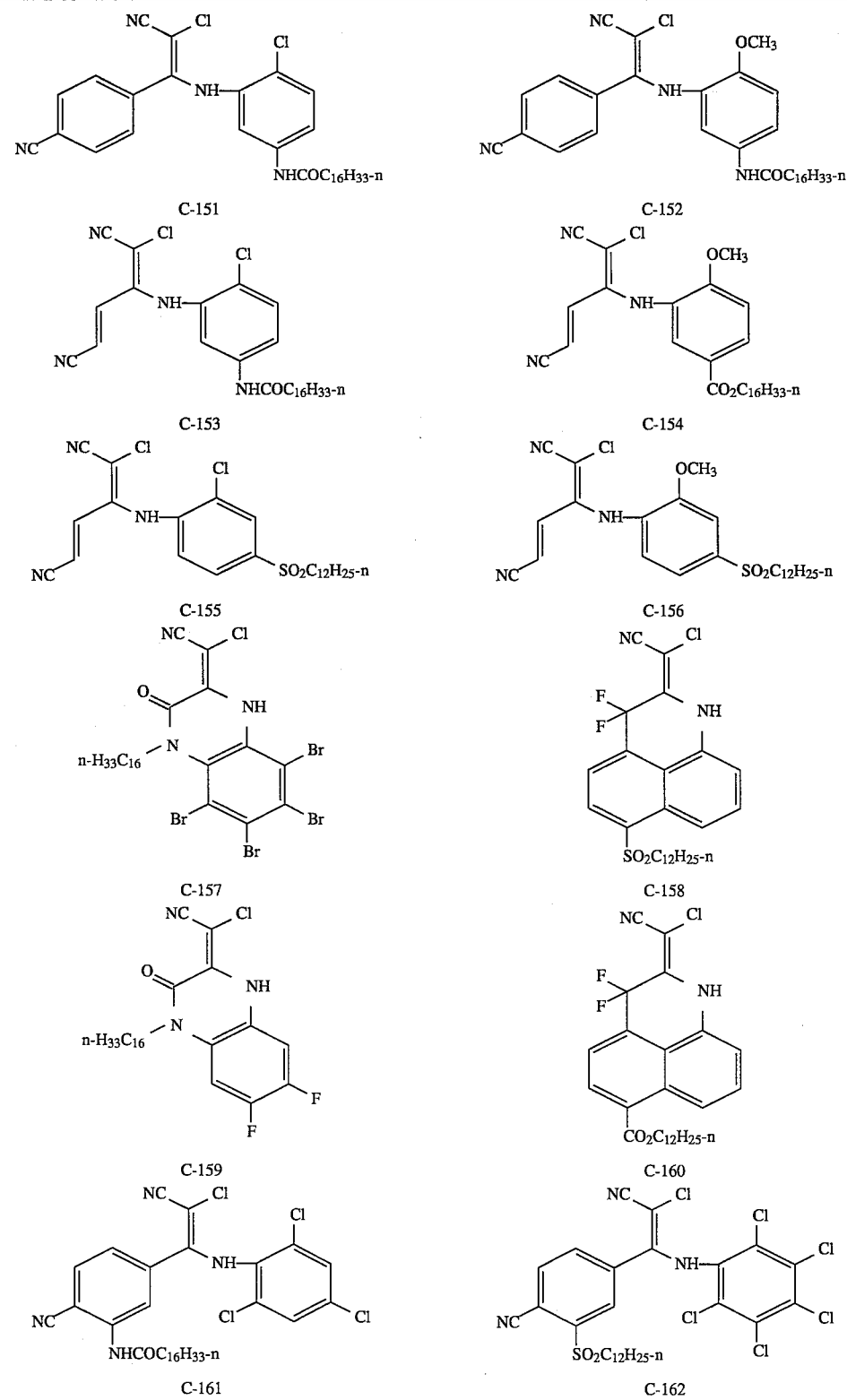

TABLE 3-continued
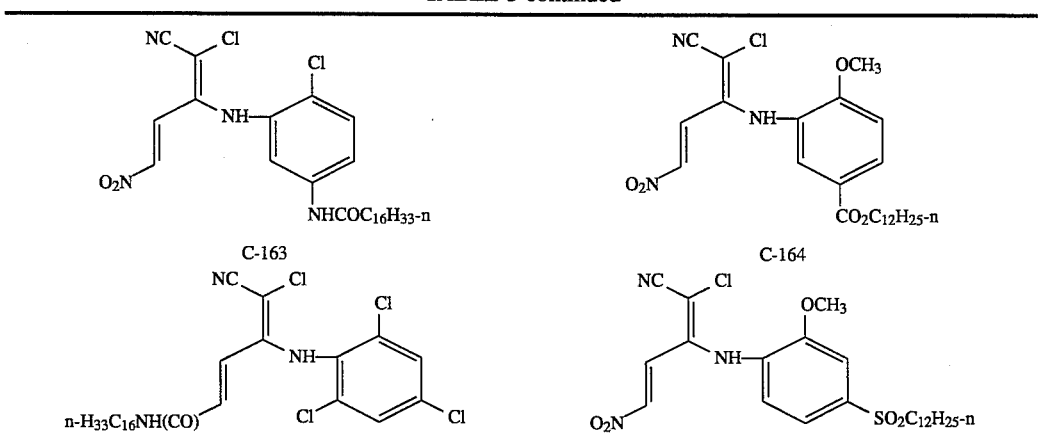
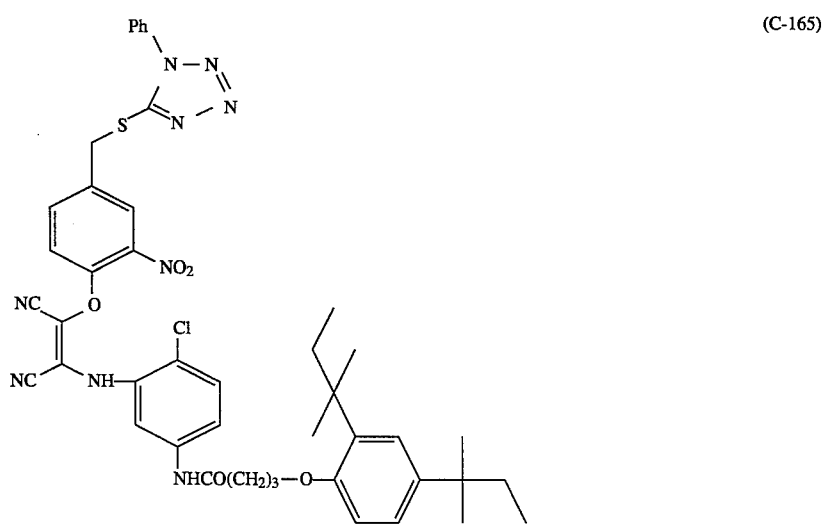
(C-165)
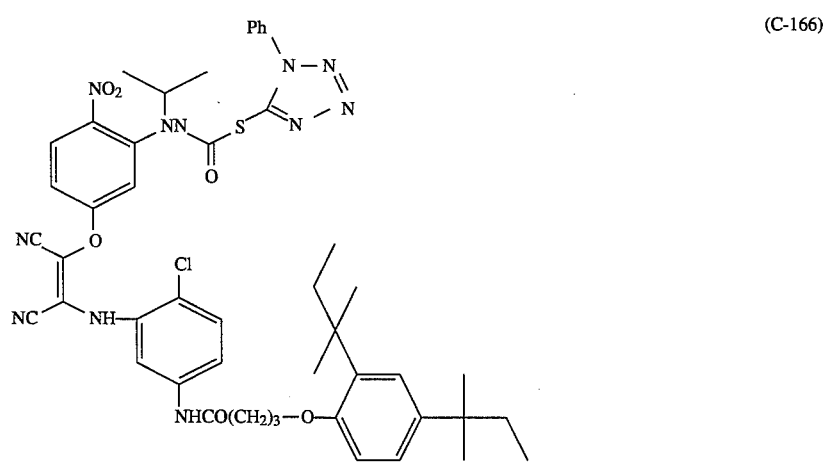
(C-166)

TABLE 3-continued
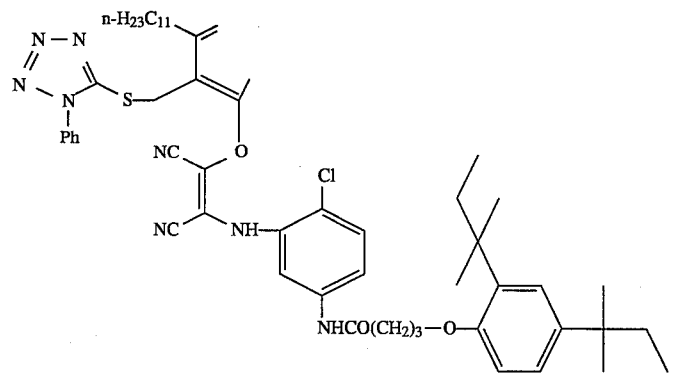
(C-167)
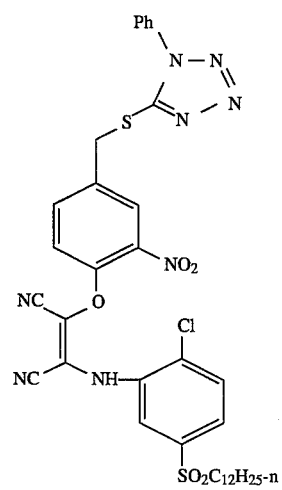
(C-168)
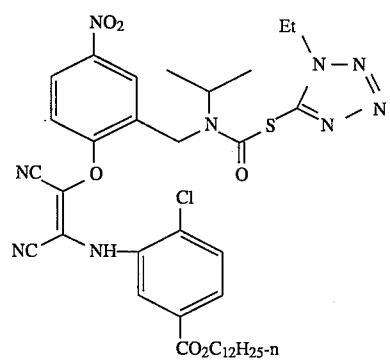
(C-169)
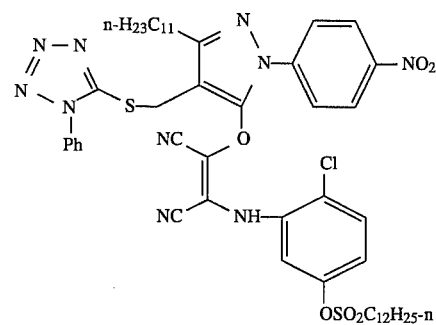
(C-170)

TABLE 3-continued
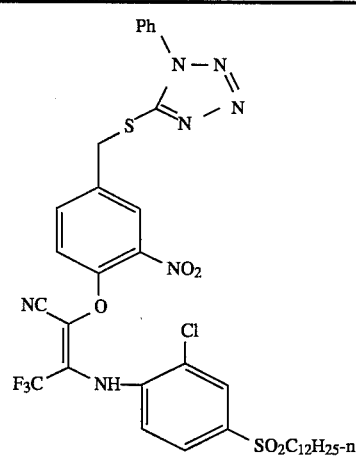
(C-171)
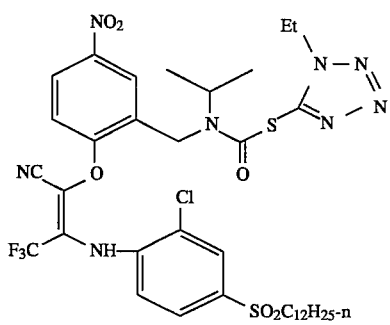
(C-172)
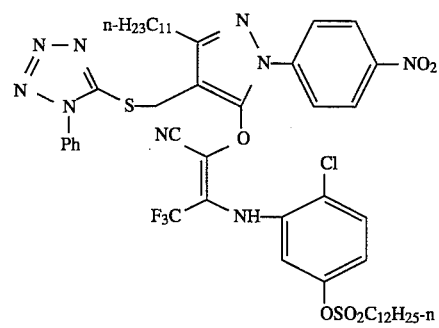
(C-173)
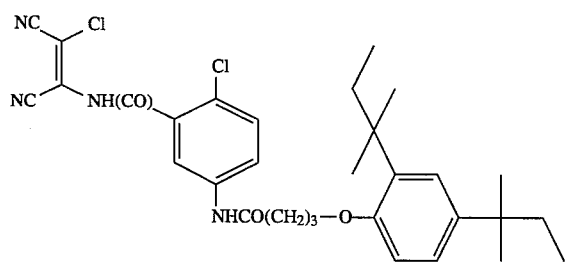
(C-174)
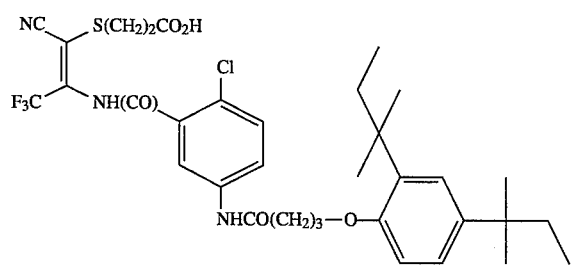
(C-175)

TABLE 3-continued
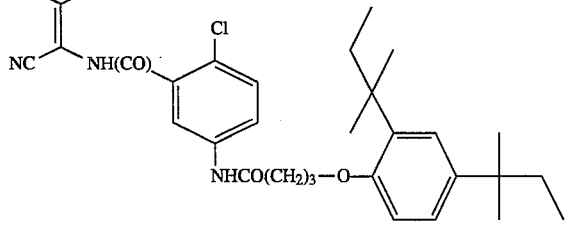
(C-176)
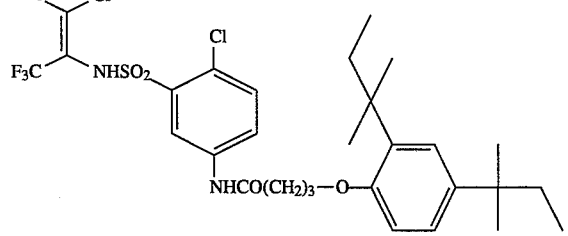
(C-177)
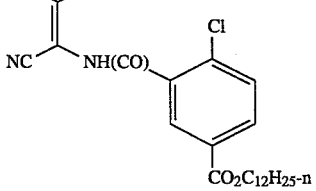
(C-178)
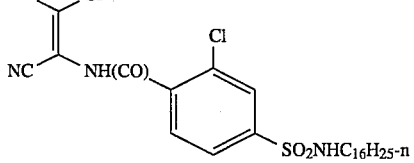
(C-179)
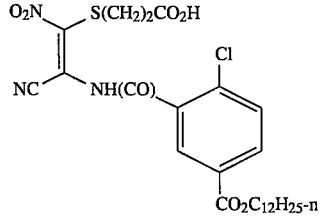
C-180
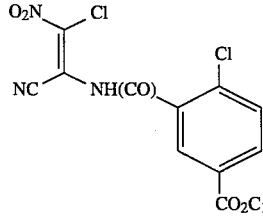
C-181
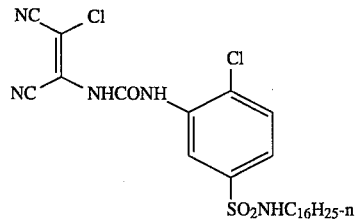
C-182
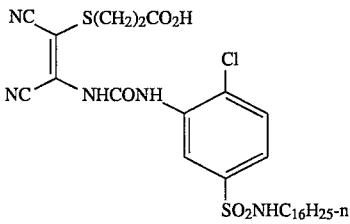
C-183
C-184
C-185

TABLE 3-continued

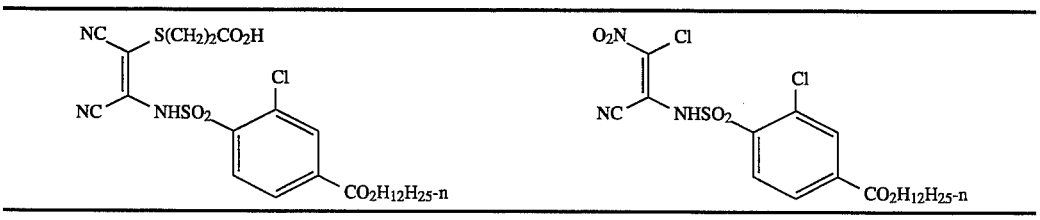

16. A photographic element as claimed in claim 1 in which the element is a multicolor photographic material comprising a support bearing a yellow dye image-forming unit comprised of at least one blue-sensitive silver halide emulsion layer having associated therewith at least one yellow dye-forming coupler, at least one magenta dye image-forming unit comprising at least one green-sensitive silver halide emulsion layer having associated therewith at least one magenta dye-forming coupler at least one cyan dye image-forming unit comprising at least one red-sensitive silver halide emulsion layer having associated therewith at least one cyan dye-forming coupler in which the magenta and/or yellow coupler is a coupler as defined in claim 1.

17. The element of claim 1 wherein R and X together complete a heterocyclic ring.

* * * * *